United States Patent
Banerjee et al.

(10) Patent No.: US 12,152,251 B2
(45) Date of Patent: Nov. 26, 2024

(54) T CELLS WITH IMPROVED FUNCTIONALITY

(71) Applicant: Kite Pharma, Inc., Santa Monica, CA (US)

(72) Inventors: Saikat Banerjee, Oakland, CA (US); Christopher Ecker, San Diego, CA (US); Yoonjung Shin, Los Angeles, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 210 days.

(21) Appl. No.: 17/410,594

(22) Filed: Aug. 24, 2021

(65) Prior Publication Data

US 2022/0064596 A1    Mar. 3, 2022

Related U.S. Application Data

(60) Provisional application No. 63/070,174, filed on Aug. 25, 2020.

(51) Int. Cl.
| | |
|---|---|
| *C12N 5/0783* | (2010.01) |
| *A61K 35/17* | (2015.01) |
| *A61K 39/00* | (2006.01) |
| *C07K 14/725* | (2006.01) |
| *C12N 9/22* | (2006.01) |
| *C12N 15/11* | (2006.01) |
| *C12N 15/113* | (2010.01) |
| *C12N 15/90* | (2006.01) |

(52) U.S. Cl.
CPC ........ *C12N 5/0636* (2013.01); *A61K 39/4611* (2023.05); *A61K 39/4631* (2023.05); *A61K 39/464412* (2023.05); *C07K 14/7051* (2013.01); *C12N 9/22* (2013.01); *C12N 15/111* (2013.01); *C12N 15/113* (2013.01); *C12N 15/902* (2013.01); *A61K 2239/31* (2023.05); *A61K 2239/38* (2023.05); *A61K 2239/48* (2023.05); *C12N 2310/141* (2013.01); *C12N 2310/20* (2017.05); *C12N 2320/30* (2013.01)

(58) Field of Classification Search
CPC ...... C12N 5/0636; C12N 9/22; C12N 15/111; C12N 15/113; C12N 15/902; C12N 2310/141; C12N 2310/20; C12N 2320/30; C12N 2510/00; C12N 5/10; C12N 15/63; A61K 35/17; C07K 14/7051; C07K 14/4702
See application file for complete search history.

(56) References Cited

U.S. PATENT DOCUMENTS

2019/0185860 A1*  6/2019  Kim ................ C07K 14/70564

FOREIGN PATENT DOCUMENTS

| WO | WO-2017/069958 A2 | 4/2017 |
|---|---|---|
| WO | WO-2018/071873 A2 | 4/2018 |
| WO | WO-2018/175733 A1 | 9/2018 |
| WO | WO-2019/191114 A1 | 10/2019 |
| WO | WO-2019/217423 A1 | 11/2019 |

OTHER PUBLICATIONS

"NCBI Supplement" is a combination of the supplementary table from Utzschneider et al Nat Immunol 21, 1256-1266 (2020)., and the referenced NCBI gene ID 12014 (https://www.ncbi.nlm.nih.gov/gene/12014) (Year: 2020).*
Intl. Search Report-Written Opinion dated Mar. 21, 2022 for Intl. Appl. No. PCT/US2021/047337.
Chihara, N. et al. (2018) "Induction and transcription regulation of the co-inhibitory gene module in T cells" Nature 558(7710):454-459.
Hwang, S. et al. (2016) "Blimp-1-mediated CD4 T cell exhaustion causes CD8 T cell dysfunction during chronic toxoplasmosis" Journal of Experimental Medicine 213(9):1799-1818.
Jameson, S.C. "T cells climb on board Blimp-1" Trends in Immunology 27(8):349-351.
Rutishauser, R.L. et al. (2009) "Transcriptional Repressor Blimp-1 Promotes CD8+ T Cell Terminal Differentiation and Represses the Acquisition of Central Memory T Cell Properties" Immunity 31(2):296-308.
Shin, H.M. et al. (2017) "Transient expression of ZBTB32 in anti-viral CD8+ T cells limits the magnitude of the effector response and the generation of memory" PLoS Pathog 13(8):e1006544.
Utzschneider, D.T. et al. (2020) "Early precursor T cells establish and propagate T cell exhaustion in chronic infection" Nature Immunology 21(10):1256-1266.

* cited by examiner

*Primary Examiner* — Jeremy C Flinders
*Assistant Examiner* — Thomas R. Amick

(57) ABSTRACT

Immune cell engineered to inhibit the endogenous expression of one or more of Blimp-1 and A20 and/or overexpress one or more of exogenous TCF7 and Bach2. Method of treating cancer, comprising administering the cells described herein. Method of increasing one or more of a peak fold proliferation rate, a killing efficiency, or inducing the cellular characteristics associated with naïve phenotype of an immune cell, comprising introducing an exogenous construct encoding a CAR or a TCR, and inhibiting the endogenous expression of one or more of Blimp-1 and A20, and/or introducing an exogenous construct encoding one or more of TCF7 and Bach2. Method of generating a modified immune cell, comprising introducing an exogenous construct encoding a CAR or a TCR, and inhibiting the endogenous expression of one or more of Blimp-1 and A20, and/or introducing an exogenous construct encoding one or more of TCF7 and Bach2.

17 Claims, No Drawings
Specification includes a Sequence Listing.

```
                              SEQUENCE LISTING

<160> NUMBER OF SEQ ID NOS: 15

<210> SEQ ID NO 1

<400> SEQUENCE: 1

000

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 2

Asp Xaa Glu Xaa Asn Pro Gly Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Ala Gly Leu Ile Asp Ala Asp Gly
1               5

<210> SEQ ID NO 4
<211> LENGTH: 389
<212> TYPE: PRT
<213> ORGANISM: Homo sapiens

<400> SEQUENCE: 4

Met Pro Gln Leu Asp Ser Gly Gly Gly Ala Gly Gly Gly Asp Asp
1               5                   10                  15

Leu Gly Ala Pro Asp Glu Leu Leu Ala Phe Gln Asp Glu Gly Glu Glu
                20                  25                  30

Gln Asp Asp Lys Ser Arg Asp Ser Ala Ala Gly Pro Glu Arg Asp Leu
            35                  40                  45

Ala Glu Leu Lys Ser Ser Leu Val Asn Glu Ser Glu Gly Ala Ala Gly
        50                  55                  60

Gly Ala Gly Ile Pro Gly Val Pro Gly Ala Gly Ala Gly Ala Arg Gly
65                  70                  75                  80

Glu Ala Glu Ala Leu Gly Arg Glu His Ala Ala Gln Arg Leu Phe Pro
                85                  90                  95

Asp Lys Leu Pro Glu Pro Leu Glu Asp Gly Leu Lys Ala Pro Glu Cys
                100                 105                 110
```

Thr Ser Gly Met Tyr Lys Glu Thr Val Tyr Ser Ala Phe Asn Leu Leu
        115                 120                 125

Met His Tyr Pro Pro Ser Gly Ala Gly Gln His Pro Gln Pro Gln
    130                 135                 140

Pro Pro Leu His Lys Ala Asn Gln Pro Pro His Gly Val Pro Gln Leu
145                 150                 155                 160

Ser Leu Tyr Glu His Phe Asn Ser Pro His Pro Thr Pro Ala Pro Ala
                165                 170                 175

Asp Ile Ser Gln Lys Gln Val His Arg Pro Leu Gln Thr Pro Asp Leu
            180                 185                 190

Ser Gly Phe Tyr Ser Leu Thr Ser Gly Ser Met Gly Gln Leu Pro His
        195                 200                 205

Thr Val Ser Trp Phe Thr His Pro Ser Leu Met Leu Gly Ser Gly Val
    210                 215                 220

Pro Gly His Pro Ala Ala Ile Pro His Pro Ala Ile Val Pro Pro Ser
225                 230                 235                 240

Gly Lys Gln Glu Leu Gln Pro Phe Asp Arg Asn Leu Lys Thr Gln Ala
                245                 250                 255

Glu Ser Lys Ala Glu Lys Glu Ala Lys Lys Pro Thr Ile Lys Lys Pro
            260                 265                 270

Leu Asn Ala Phe Met Leu Tyr Met Lys Glu Met Arg Ala Lys Val Ile
        275                 280                 285

Ala Glu Cys Thr Leu Lys Glu Ser Ala Ala Ile Asn Gln Ile Leu Gly
    290                 295                 300

Arg Arg Trp His Ala Leu Ser Arg Glu Glu Gln Ala Lys Tyr Tyr Glu
305                 310                 315                 320

Leu Ala Arg Lys Glu Arg Gln Leu His Met Gln Leu Tyr Pro Gly Trp
                325                 330                 335

Ser Ala Arg Asp Asn Tyr Gly Lys Lys Lys Arg Arg Ser Arg Glu Lys
            340                 345                 350

His Gln Glu Ser Thr Thr Gly Gly Lys Arg Asn Ala Phe Gly Thr Tyr
        355                 360                 365

Pro Glu Lys Ala Ala Ala Pro Ala Pro Phe Leu Pro Met Thr Val Leu
    370                 375                 380

Arg Ala Lys Arg Ser
385

<210> SEQ ID NO 5
<211> LENGTH: 1167
<212> TYPE: DNA
<213> ORGANISM: Homo sapiens

<400> SEQUENCE: 5
atgcctcagc tggattctgg cggaggcgga gctggtggcg agatgatct tggagcacct      60 gatgagctgc tggcattcca ggacgagggc aagaacagg acgacaagag cagagattct    120
gccgccggac ctgagagaga tctggccgag ctgaagtcca gcctggtcaa tgaatctgaa    180
ggcgccgctg gcggcgctgg aattcctggt gttcctggcg ctggtgctgg tgcaagaggc    240
gaagctgaag ccctgggaag agaacacgct gcccagagac tgttccccga caagctgcct    300
gagcctctgg aagatggact gaaggcccct gagtgtacca gcggcatgta caagaaacc    360 gtgtacagcg ccttcaacct gctgatgcac taccctccac ctagcggagc aggacagcat    420
cctcaacctc agcctccact gcacaaggcc aatcagccac tcatggcgt gccacagctg    480

-continued

```
agcctgtacg agcacttcaa cagccctcat cctactccag ctccagccga catcagccag    540
aaacaggtgc acagacctct gcagacccct gacctgagcg gcttttacag cctgacaagc    600
ggcagcatgg gacagctgcc tcataccgtg tcctggttca cacacccag cctgatgctt     660 ggaagcggag tgcctggaca ccctgccgct attcctcatc ctgccatcgt gcctccaagc    720
ggcaagcaag agctgcagcc cttcgaccgg aacctgaaaa cacaggccga gagcaaggcc    780
gagaaagagg ccaagaagcc caccatcaag aagcctctga acgccttcat gctgtacatg    840
aaagaaatgc gggccaaagt gatcgccgag tgcaccctga agagtccgc cgccatcaac    900 cagatcctgg gcagaagatg gcacgccctg tccagagagg aacaggccaa gtactacgag    960
ctggcccgga agaacggca gctgcacatg caactgtacc ctggctggag cgccagagac    1020
aactacggca agaagaagcg gcggagcaga gagaagcacc aagagtctac aaccggcggc    1080
aagagaaacg ccttcggcac atatcccgag aaagccgctg ctcccgctcc tttcctgcct    1140
atgactgtgc tgagggccaa gagaagc                                       1167
```

<210> SEQ ID NO 6
<211> LENGTH: 684
<212> TYPE: PRT
<213> ORGANISM: Homo sapiens

<400> SEQUENCE: 6

```
Met Pro Gln Leu Asp Ser Gly Gly Gly Ala Gly Gly Gly Asp Asp
1               5                   10                  15

Leu Gly Ala Pro Asp Glu Leu Leu Ala Phe Gln Asp Glu Gly Glu Glu
                20                  25                  30

Gln Asp Asp Lys Ser Arg Asp Ser Ala Ala Gly Pro Glu Arg Asp Leu
            35                  40                  45

Ala Glu Leu Lys Ser Ser Leu Val Asn Glu Ser Glu Gly Ala Ala Gly
        50                  55                  60

Gly Ala Gly Ile Pro Gly Val Pro Gly Ala Gly Ala Arg Gly
65                  70                  75                  80

Glu Ala Glu Ala Leu Gly Arg Glu His Ala Ala Gln Arg Leu Phe Pro
                85                  90                  95

Asp Lys Leu Pro Glu Pro Leu Glu Asp Gly Leu Lys Ala Pro Glu Cys
                100                 105                 110

Thr Ser Gly Met Tyr Lys Glu Thr Val Tyr Ser Ala Phe Asn Leu Leu
            115                 120                 125

Met His Tyr Pro Pro Pro Ser Gly Ala Gly Gln His Pro Gln Pro Gln
        130                 135                 140

Pro Pro Leu His Lys Ala Asn Gln Pro Pro His Gly Val Pro Gln Leu
145                 150                 155                 160

Ser Leu Tyr Glu His Phe Asn Ser Pro His Pro Thr Pro Ala Pro Ala
                165                 170                 175

Asp Ile Ser Gln Lys Gln Val His Arg Pro Leu Gln Thr Pro Asp Leu
            180                 185                 190

Ser Gly Phe Tyr Ser Leu Thr Ser Gly Ser Met Gly Gln Leu Pro His
        195                 200                 205

Thr Val Ser Trp Phe Thr His Pro Ser Leu Met Leu Gly Ser Gly Val
    210                 215                 220

Pro Gly His Pro Ala Ala Ile Pro His Pro Ala Ile Val Pro Ser
225                 230                 235                 240

Gly Lys Gln Glu Leu Gln Pro Phe Asp Arg Asn Leu Lys Thr Gln Ala
                245                 250                 255
```

-continued

Glu Ser Lys Ala Glu Lys Ala Lys Lys Pro Thr Ile Lys Lys Pro
              260                 265                 270

Leu Asn Ala Phe Met Leu Tyr Met Lys Glu Met Arg Ala Lys Val Ile
              275                 280                 285

Ala Glu Cys Thr Leu Lys Glu Ser Ala Ala Ile Asn Gln Ile Leu Gly
          290                 295                 300

Arg Arg Trp His Ala Leu Ser Arg Glu Glu Ala Lys Tyr Tyr Glu
305                 310                 315                 320

Leu Ala Arg Lys Glu Arg Gln Leu His Met Gln Leu Tyr Pro Gly Trp
              325                 330                 335

Ser Ala Arg Asp Asn Tyr Gly Lys Lys Arg Arg Ser Arg Glu Lys
              340                 345                 350

His Gln Glu Ser Thr Thr Gly Gly Lys Arg Asn Ala Phe Gly Thr Tyr
              355                 360                 365

Pro Glu Lys Ala Ala Ala Pro Ala Pro Phe Leu Pro Met Thr Val Leu
    370                 375                 380

Arg Ala Lys Arg Ser Gly Ser Gly Glu Gly Arg Gly Ser Leu Leu Thr
385                 390                 395                 400

Cys Gly Asp Val Glu Glu Asn Pro Gly Pro Met Gly Ala Gly Ala Thr
              405                 410                 415

Gly Arg Ala Met Asp Gly Pro Arg Leu Leu Leu Leu Leu Leu Leu Gly
              420                 425                 430

Val Ser Leu Gly Gly Ala Lys Glu Ala Cys Pro Thr Gly Leu Tyr Thr
          435                 440                 445

His Ser Gly Glu Cys Cys Lys Ala Cys Asn Leu Gly Glu Gly Val Ala
    450                 455                 460

Gln Pro Cys Gly Ala Asn Gln Thr Val Cys Glu Pro Cys Leu Asp Ser
465                 470                 475                 480

Val Thr Phe Ser Asp Val Val Ser Ala Thr Glu Pro Cys Lys Pro Cys
              485                 490                 495

Thr Glu Cys Val Gly Leu Gln Ser Met Ser Ala Pro Cys Val Glu Ala
              500                 505                 510

Asp Asp Ala Val Cys Arg Cys Ala Tyr Gly Tyr Tyr Gln Asp Glu Thr
    515                 520                 525

Thr Gly Arg Cys Glu Ala Cys Arg Val Cys Glu Ala Gly Ser Gly Leu
    530                 535                 540

Val Phe Ser Cys Gln Asp Lys Gln Asn Thr Val Cys Glu Glu Cys Pro
545                 550                 555                 560

Asp Gly Thr Tyr Ser Asp Glu Ala Asn His Val Asp Pro Cys Leu Pro
              565                 570                 575

Cys Thr Val Cys Glu Asp Thr Glu Arg Gln Leu Arg Glu Cys Thr Arg
              580                 585                 590

Trp Ala Asp Ala Glu Cys Glu Glu Ile Pro Gly Arg Trp Ile Thr Arg
              595                 600                 605

Ser Thr Pro Pro Glu Gly Ser Asp Ser Thr Ala Pro Ser Thr Gln Glu
    610                 615                 620

Pro Glu Ala Pro Pro Glu Gln Asp Leu Ile Ala Ser Thr Val Ala Gly
625                 630                 635                 640

Val Val Thr Thr Val Met Gly Ser Ser Gln Pro Val Val Thr Arg Gly
              645                 650                 655

Thr Thr Asp Asn Leu Ile Pro Val Tyr Cys Ser Ile Leu Ala Ala Val
              660                 665                 670

-continued

Val Val Gly Leu Val Ala Tyr Ile Ala Phe Lys Arg
    675                    680

<210> SEQ ID NO 7
<211> LENGTH: 2061
<212> TYPE: DNA
<213> ORGANISM: Homo sapiens

<400> SEQUENCE: 7

| | | | | | |
|---|---|---|---|---|---|
| atgcctcagc | tggattctgg | cggaggcgga | gctggtggcg | gagatgatct | tggagcacct | 60 |
| gatgagctgc | tggcattcca | ggacgagggc | gaagaacagg | acgacaagag | cagagattct | 120 |
| gccgccggac | ctgagagaga | tctggccgag | ctgaagtcca | gcctggtcaa | tgaatctgaa | 180 |
| ggcgccgctg | gcggcgctgg | aattcctggt | gttcctggcg | ctggtgctgg | tgcaagaggc | 240 |
| gaagctgaag | ccctgggaag | agaacacgct | gcccagagac | tgttccccga | caagctgcct | 300 |
| gagcctctgg | aagatggact | gaaggcccct | gagtgtacca | gcggcatgta | caaagaaacc | 360 |
| gtgtacagcg | ccttcaacct | gctgatgcac | taccctccac | ctagcggagc | aggacagcat | 420 |
| cctcaacctc | agcctccact | gcacaaggcc | aatcagccac | tcatggcgt | gccacagctg | 480 |
| agcctgtacg | agcacttcaa | cagccctcat | cctactccag | ctccagccga | catcagccag | 540 |
| aaacaggtgc | acagacctct | gcagacccct | gacctgagcg | cttttacag | cctgacaagc | 600 |
| ggcagcatgg | acagctgcc | tcataccgtg | tcctggttca | cacccccag | cctgatgctt | 660 |
| ggaagcggag | tgcctggaca | ccctgccgct | attcctcatc | ctgccatcgt | gcctccaagc | 720 |
| ggcaagcaag | agctgcagcc | cttcgaccgg | aacctgaaaa | cacaggccga | gagcaaggcc | 780 |
| gagaaagagg | ccaagaagcc | caccatcaag | aagcctctga | cgccttcat | gctgtacatg | 840 |
| aaagaaatgc | gggccaaagt | gatcgccgag | tgcacccctga | aagagtccgc | cgccatcaac | 900 |
| cagatcctgg | gcagaagatg | gcacgccctg | tccagagagg | aacaggccaa | gtactacgag | 960 |
| ctggcccgga | agaacggca | gctgcacatg | caactgtacc | ctggctggag | cgccagagac | 1020 |
| aactacggca | agaagaagcg | gcggagcaga | gagaagcacc | aagagtctac | aaccggcggc | 1080 |
| aagagaaacg | ccttcggcac | atatcccgag | aaagccgctg | ctcccgctcc | tttcctgcct | 1140 |
| atgactgtgc | tgagggccaa | gagaagcgga | agtggagagg | gaagaggctc | ccttctgaca | 1200 |
| tgcggcgacg | tggaggagaa | ccctggacct | atgggagctg | gagctaccgg | aagagctatg | 1260 |
| gacggaccaa | gacttctcct | gctcctcctg | ctgggtgtga | gctgggagg | agctaaggag | 1320 |
| gcttgcccta | ccggactgta | cacccactct | ggcgagtgct | gcaaggcttg | caacctggga | 1380 |
| gagggagtgg | ctcaaccctg | cggagctaac | caaactgtct | gcgagccttg | cctggactct | 1440 |
| gtgacattct | ccgacgtggt | gtctgccacc | gagccttgca | agccttgcac | cgaatgcgtg | 1500 |
| ggcctgcaaa | gcatgagcgc | tccttgcgtg | gaggctgacg | acgctgtgtg | ccgatgcgct | 1560 |
| tacggatact | accaagacga | gaccaccgga | agatgcgagg | cttgccgagt | gtgcgaggct | 1620 |
| ggaagcggac | tcgtgttctc | ctgccaagac | aagcaaaaca | ccgtgtgtga | ggaatgccct | 1680 |
| gacggaacct | actccgacga | ggctaaccac | gtggaccctt | gcctgccttg | caccgtgtgt | 1740 |
| gaggacaccg | agagacaact | gagggagtgc | acaagatggg | ctgacgctga | gtgtgaggag | 1800 |
| atccctggaa | gatggatcac | aagatctacc | cctcctgagg | gaagcgactc | caccgctcct | 1860 |
| tccacccaag | agcccgaggc | tcctcctgag | caagacctga | tcgcaagcac | cgtggctgga | 1920 |
| gtggttacaa | ccgtgatggg | aagctcccaa | cccgtggtta | caaggggaac | caccgacaac | 1980 |
| ctgatccctg | tgtactgctc | catcctggct | gctgtggtgg | tgggattggt | ggcctacatc | 2040 |

-continued

```
gctttcaaga gatgaatcga t                                              2061
```

<210> SEQ ID NO 8
<211> LENGTH: 846
<212> TYPE: PRT
<213> ORGANISM: Homo sapiens

<400> SEQUENCE: 8

```
Met Ser Val Asp Glu Lys Pro Asp Ser Pro Met Tyr Val Tyr Glu Ser
1               5                   10                  15

Thr Val His Cys Thr Asn Ile Leu Leu Gly Leu Asn Asp Gln Arg Lys
            20                  25                  30

Lys Asp Ile Leu Cys Asp Val Thr Leu Ile Val Glu Arg Lys Glu Phe
        35                  40                  45

Arg Ala His Arg Ala Val Leu Ala Ala Cys Ser Glu Tyr Phe Trp Gln
    50                  55                  60

Ala Leu Val Gly Gln Thr Lys Asn Asp Leu Val Val Ser Leu Pro Glu
65                  70                  75                  80

Glu Val Thr Ala Arg Gly Phe Gly Pro Leu Leu Gln Phe Ala Tyr Thr
                85                  90                  95

Ala Lys Leu Leu Leu Ser Arg Glu Asn Ile Arg Glu Val Ile Arg Cys
            100                 105                 110

Ala Glu Phe Leu Arg Met His Asn Leu Glu Asp Ser Cys Phe Ser Phe
        115                 120                 125

Leu Gln Thr Gln Leu Leu Asn Ser Glu Asp Gly Leu Phe Val Cys Arg
    130                 135                 140

Lys Asp Ala Ala Cys Gln Arg Pro His Glu Asp Cys Glu Asn Ser Ala
145                 150                 155                 160

Gly Glu Glu Glu Asp Glu Glu Glu Thr Met Asp Ser Glu Thr Ala
                165                 170                 175

Lys Met Ala Cys Pro Arg Asp Gln Met Leu Pro Glu Pro Ile Ser Phe
            180                 185                 190

Glu Ala Ala Ile Pro Val Ala Glu Lys Glu Ala Leu Leu Pro
        195                 200                 205

Glu Pro Asp Val Pro Thr Asp Thr Lys Glu Ser Ser Glu Lys Asp Ala
    210                 215                 220

Leu Thr Gln Tyr Pro Arg Tyr Lys Lys Tyr Gln Leu Ala Cys Thr Lys
225                 230                 235                 240

Asn Val Tyr Asn Ala Ser Ser His Ser Thr Ser Gly Phe Ala Ser Thr
                245                 250                 255

Phe Arg Glu Asp Asn Ser Ser Asn Ser Leu Lys Pro Gly Leu Ala Arg
            260                 265                 270

Gly Gln Ile Lys Ser Glu Pro Pro Ser Glu Glu Asn Glu Glu Glu Ser
        275                 280                 285

Ile Thr Leu Cys Leu Ser Gly Asp Glu Pro Asp Ala Lys Asp Arg Ala
    290                 295                 300

Gly Asp Val Glu Met Asp Arg Lys Gln Pro Ser Pro Ala Pro Thr Pro
305                 310                 315                 320

Thr Ala Pro Ala Gly Ala Ala Cys Leu Glu Arg Ser Arg Ser Val Ala
                325                 330                 335

Ser Pro Ser Cys Leu Arg Ser Leu Phe Ser Ile Thr Lys Ser Val Glu
            340                 345                 350

Leu Ser Gly Leu Pro Ser Thr Ser Gln Gln His Phe Ala Arg Ser Pro
        355                 360                 365
```

```
Ala Cys Pro Phe Asp Lys Gly Ile Thr Gln Gly Asp Leu Lys Thr Asp
    370             375             380
Tyr Thr Pro Phe Thr Gly Asn Tyr Gly Gln Pro His Val Gly Gln Lys
385             390             395             400
Glu Val Ser Asn Phe Thr Met Gly Ser Pro Leu Arg Gly Pro Gly Leu
            405             410             415
Glu Ala Leu Cys Lys Gln Gly Glu Leu Asp Arg Arg Ser Val Ile
        420             425             430
Phe Ser Ser Ser Ala Cys Asp Gln Val Ser Thr Ser Val His Ser Tyr
        435             440             445
Ser Gly Val Ser Ser Leu Asp Lys Asp Leu Ser Glu Pro Val Pro Lys
    450             455             460
Gly Leu Trp Val Gly Ala Gly Gln Ser Leu Pro Ser Ser Gln Ala Tyr
465             470             475             480
Ser His Gly Gly Leu Met Ala Asp His Leu Pro Gly Arg Met Arg Pro
            485             490             495
Asn Thr Ser Cys Pro Val Pro Ile Lys Val Cys Pro Arg Ser Pro Pro
            500             505             510
Leu Glu Thr Arg Thr Arg Thr Ser Ser Ser Cys Ser Ser Tyr Ser Tyr
            515             520             525
Ala Glu Asp Gly Ser Gly Gly Ser Pro Cys Ser Leu Pro Leu Cys Glu
    530             535             540
Phe Ser Ser Ser Pro Cys Ser Gln Gly Ala Arg Phe Leu Ala Thr Glu
545             550             555             560
His Gln Glu Pro Gly Leu Met Gly Asp Gly Met Tyr Asn Gln Val Arg
            565             570             575
Pro Gln Ile Lys Cys Glu Gln Ser Tyr Gly Thr Asn Ser Ser Asp Glu
            580             585             590
Ser Gly Ser Phe Ser Glu Ala Asp Ser Glu Ser Cys Pro Val Gln Asp
    595             600             605
Arg Gly Gln Glu Val Lys Leu Pro Phe Pro Val Asp Gln Ile Thr Asp
    610             615             620
Leu Pro Arg Asn Asp Phe Gln Met Met Ile Lys Met His Lys Leu Thr
625             630             635             640
Ser Glu Gln Leu Glu Phe Ile His Asp Val Arg Arg Arg Ser Lys Asn
            645             650             655
Arg Ile Ala Ala Gln Arg Cys Arg Lys Arg Lys Leu Asp Cys Ile Gln
            660             665             670
Asn Leu Glu Cys Glu Ile Arg Lys Leu Val Cys Glu Lys Glu Lys Leu
            675             680             685
Leu Ser Glu Arg Asn Gln Leu Lys Ala Cys Met Gly Glu Leu Leu Asp
    690             695             700
Asn Phe Ser Cys Leu Ser Gln Glu Val Cys Arg Asp Ile Gln Ser Pro
705             710             715             720
Glu Gln Ile Gln Ala Leu His Arg Tyr Cys Pro Val Leu Arg Pro Met
            725             730             735
Asp Leu Pro Thr Ala Ser Ser Ile Asn Pro Ala Pro Leu Gly Ala Glu
            740             745             750
Gln Asn Ile Ala Ala Ser Gln Cys Ala Val Gly Glu Asn Val Pro Cys
        755             760             765
Cys Leu Glu Pro Gly Ala Ala Pro Pro Gly Pro Pro Trp Ala Pro Ser
    770             775             780
Asn Thr Ser Glu Asn Cys Thr Ser Gly Arg Arg Leu Glu Gly Thr Asp
```

```
                    785                 790                 795                 800
Pro Gly Thr Phe Ser Glu Arg Gly Pro Pro Leu Glu Pro Arg Ser Gln
                805                 810                 815

Thr Val Thr Val Asp Phe Cys Gln Glu Met Thr Asp Lys Cys Thr Thr
                820                 825                 830

Asp Glu Gln Pro Arg Lys Asp Tyr Thr Arg Ala Lys Arg Ser
                835                 840                 845
```

<210> SEQ ID NO 9
<211> LENGTH: 2538
<212> TYPE: DNA
<213> ORGANISM: Homo sapiens

<400> SEQUENCE: 9

```
atgagcgtgg acgagaagcc tgacagccct atgtacgtgt acgagagcac cgtgcactgc     60
accaacatcc tgctgggcct gaacgaccag cggaagaaag acatcctgtg cgacgtgacc    120
ctgatcgtgg aacggaaaga gttcagagcc cacagagccg tgctggccgc ctgtagcgag    180
tatttttggc aggccctcgt gggccagacc aagaacgatc tggtggtgtc cctgcctgag    240
gaagtgaccg ccagaggatt tggacccctg ctgcagtttg cctacaccgc caaactgctg    300
ctgagccgcg agaacatccg ggaagtgatc agatgcgccg agttcctgcg gatgcacaac    360
ctggaagata gctgcttcag cttcctgcag acccagctgc tgaacagcga ggatggcctg    420
ttcgtgtgca gaaaggatgc cgcctgtcag aggcctcacg aggactgcga aaattctgcc    480
ggcgaggaag aggacgaaga ggaagaaacc atggacagcg agacagccaa gatggcttgc    540
cccagggacc agatgctgcc tgagcctatc tctttcgagg ccgctgccat tcctgtggcc    600
gagaaagaag aagcccctgct gccagagcca gacgtgccca ccgatacaaa agagagcagc    660
gagaaggacg ccctgacaca gtacccaga tacaagaagt accagctggc ctgcaccaag    720
aatgtgtaca cgccagcag ccacagcacc agcggctttg cctctacctt cagagaggac    780
aacagcagca acagcctgaa gcctggactg gccagaggcc agatcaagtc tgagcctcct    840
agcgaggaaa atgaagagga atctatcacc ctgtgcctga gcggcgacga gcctgatgcc    900
aaagatagag ctggcgacgt ggaaatggac cggaagcagc cttctccagc tcctacacct    960
acagctccag ctggcgcagc ctgcctggaa agatcaagat ctgtggctag ccccagctgc   1020
ctgcggagcc tgtttagcat caccaagagc gtggaactga cggcctgcc tagcacatcc   1080
cagcagcact tgccagatc tcccgcctgt cctttcgaca agggaatcac ccagggcgac   1140
ctgaaaaccg actacacccc tttcaccggc aactacggac agcctcacgt gggacagaaa   1200
gaggtgtcca cttaccat gggcagccct ctgagaggcc caggacttga ggccctgtgt   1260
aaacaagagg gcgagctgga tcggcggagc gtgatctttt ctagcagcgc ctgtgaccag   1320
gtgtccacca gcgtgcactc ttacagcgga gtgtccagcc tggataagga cctgtctgag   1380
cccgtgccta aaggcctgtg ggttggagct ggacagagcc tgccaagcag ccaggcttat   1440
tctcacggcg gactgatggc cgatcatctg cctggtagaa tgcggcccaa caccagctgt   1500
cccgtgccaa tcaaagtgtg ccctagaagc cctcctctgg aaacccggac cagaaccagc   1560
agcagctgtt ccagctacag ctatgccgag atggaagcg cggcagccc ttgttcactg   1620
cctctgtgcg agtttagcag cagccctgt tctcagggcg ccagatttct ggccaccgag   1680
catcaagaac ctggcctgat gggcgacggc atgtacaatc aagtgcggcc ccagattaag   1740
tgcgagcaga gctacggcac caacagctct gatgagagcg gcagctttag cgaggccgat   1800
```

-continued

```
agcgaaagct gccccgtgca ggatagaggc caagaagtga agctgcccct tccagtggat    1860
cagatcaccg acctgcctcg gaacgacttc cagatgatga tcaagatgca caagctgacc    1920
tccgagcagc tggaattcat ccacgacgtg cggcggagaa gcaagaacag aatcgctgcc    1980
cagcggtgcc ggaagagaaa gctggactgc atccagaatc tggaatgcga gatccggaag    2040
ctcgtgtgcg aaaaagagaa gctgctgtcc gagcggaacc agctgaaggc ctgtatggga    2100
gagctgctgg acaacttcag ctgtctgtct caagaagtgt gccggacaca tccagtctcca    2160 gagcagattc aggccctgca cagatactgc cctgtgctga ggcctatgga tctgcctaca    2220
gccagcagca tcaaccctgc tcctctggga gccgagcaga atattgccgc ctctcagtgt    2280
gccgtgggcg agaatgtgcc ttgctgtctt gaacctggcg ccgctcctcc tggacctcct    2340
tgggctcctt ctaacaccag cgagaactgc acctccggca aaggctgga aggcacagat    2400 cctggcacct tcagcgaaag aggcccacca ctggaaccca gatctcagac cgtgaccgtg    2460
gacttctgcc aagagatgac cgacaagtgc accaccgacg agcagcccag aaaggactac    2520
accagggcca agagaagc                                                  2538
```

<210> SEQ ID NO 10
<211> LENGTH: 1141
<212> TYPE: PRT
<213> ORGANISM: Homo sapiens

<400> SEQUENCE: 10

```
Met Ser Val Asp Glu Lys Pro Asp Ser Pro Met Tyr Val Tyr Glu Ser
1               5                   10                  15

Thr Val His Cys Thr Asn Ile Leu Leu Gly Leu Asn Asp Gln Arg Lys
            20                  25                  30

Lys Asp Ile Leu Cys Asp Val Thr Leu Ile Val Glu Arg Lys Glu Phe
        35                  40                  45

Arg Ala His Arg Ala Val Leu Ala Ala Cys Ser Glu Tyr Phe Trp Gln
    50                  55                  60

Ala Leu Val Gly Gln Thr Lys Asn Asp Leu Val Val Ser Leu Pro Glu
65                  70                  75                  80

Glu Val Thr Ala Arg Gly Phe Gly Pro Leu Leu Gln Phe Ala Tyr Thr
                85                  90                  95

Ala Lys Leu Leu Leu Ser Arg Glu Asn Ile Arg Glu Val Ile Arg Cys
            100                 105                 110

Ala Glu Phe Leu Arg Met His Asn Leu Glu Asp Ser Cys Phe Ser Phe
        115                 120                 125

Leu Gln Thr Gln Leu Leu Asn Ser Glu Asp Gly Leu Phe Val Cys Arg
    130                 135                 140

Lys Asp Ala Ala Cys Gln Arg Pro His Glu Asp Cys Glu Asn Ser Ala
145                 150                 155                 160

Gly Glu Glu Glu Asp Glu Glu Glu Thr Met Asp Ser Glu Thr Ala
                165                 170                 175

Lys Met Ala Cys Pro Arg Asp Gln Met Leu Pro Glu Pro Ile Ser Phe
            180                 185                 190

Glu Ala Ala Ile Pro Val Ala Glu Lys Glu Ala Leu Leu Pro
        195                 200                 205

Glu Pro Asp Val Pro Thr Asp Thr Lys Glu Ser Ser Glu Lys Asp Ala
    210                 215                 220

Leu Thr Gln Tyr Pro Arg Tyr Lys Lys Tyr Gln Leu Ala Cys Thr Lys
225                 230                 235                 240
```

```
Asn Val Tyr Asn Ala Ser Ser His Ser Thr Ser Gly Phe Ala Ser Thr
                245                 250                 255
Phe Arg Glu Asp Asn Ser Ser Asn Ser Leu Lys Pro Gly Leu Ala Arg
            260                 265                 270
Gly Gln Ile Lys Ser Glu Pro Pro Ser Glu Glu Asn Glu Glu Glu Ser
        275                 280                 285
Ile Thr Leu Cys Leu Ser Gly Asp Glu Pro Asp Ala Lys Asp Arg Ala
    290                 295                 300
Gly Asp Val Glu Met Asp Arg Lys Gln Pro Ser Pro Ala Pro Thr Pro
305                 310                 315                 320
Thr Ala Pro Ala Gly Ala Ala Cys Leu Glu Arg Ser Arg Ser Val Ala
                325                 330                 335
Ser Pro Ser Cys Leu Arg Ser Leu Phe Ser Ile Thr Lys Ser Val Glu
            340                 345                 350
Leu Ser Gly Leu Pro Ser Thr Ser Gln Gln His Phe Ala Arg Ser Pro
        355                 360                 365
Ala Cys Pro Phe Asp Lys Gly Ile Thr Gln Gly Asp Leu Lys Thr Asp
    370                 375                 380
Tyr Thr Pro Phe Thr Gly Asn Tyr Gly Gln Pro His Val Gly Gln Lys
385                 390                 395                 400
Glu Val Ser Asn Phe Thr Met Gly Ser Pro Leu Arg Gly Pro Gly Leu
                405                 410                 415
Glu Ala Leu Cys Lys Gln Glu Gly Glu Leu Asp Arg Arg Ser Val Ile
            420                 425                 430
Phe Ser Ser Ser Ala Cys Asp Gln Val Ser Thr Ser Val His Ser Tyr
        435                 440                 445
Ser Gly Val Ser Ser Leu Asp Lys Asp Leu Ser Glu Pro Val Pro Lys
    450                 455                 460
Gly Leu Trp Val Gly Ala Gly Gln Ser Leu Pro Ser Ser Gln Ala Tyr
465                 470                 475                 480
Ser His Gly Gly Leu Met Ala Asp His Leu Pro Gly Arg Met Arg Pro
                485                 490                 495
Asn Thr Ser Cys Pro Val Pro Ile Lys Val Cys Pro Arg Ser Pro Pro
            500                 505                 510
Leu Glu Thr Arg Thr Arg Thr Ser Ser Ser Cys Ser Ser Tyr Ser Tyr
        515                 520                 525
Ala Glu Asp Gly Ser Gly Gly Ser Pro Cys Ser Leu Pro Leu Cys Glu
    530                 535                 540
Phe Ser Ser Ser Pro Cys Ser Gln Gly Ala Arg Phe Leu Ala Thr Glu
545                 550                 555                 560
His Gln Glu Pro Gly Leu Met Gly Asp Gly Met Tyr Asn Gln Val Arg
                565                 570                 575
Pro Gln Ile Lys Cys Glu Gln Ser Tyr Gly Thr Asn Ser Ser Asp Glu
            580                 585                 590
Ser Gly Ser Phe Ser Glu Ala Asp Ser Glu Ser Cys Pro Val Gln Asp
        595                 600                 605
Arg Gly Gln Glu Val Lys Leu Pro Phe Pro Val Asp Gln Ile Thr Asp
    610                 615                 620
Leu Pro Arg Asn Asp Phe Gln Met Met Ile Lys Met His Lys Leu Thr
625                 630                 635                 640
Ser Glu Gln Leu Glu Phe Ile His Asp Val Arg Arg Arg Ser Lys Asn
                645                 650                 655
Arg Ile Ala Ala Gln Arg Cys Arg Lys Arg Lys Leu Asp Cys Ile Gln
```

```
                660             665             670
Asn Leu Glu Cys Glu Ile Arg Lys Leu Val Cys Glu Lys Glu Lys Leu
        675                 680                 685
Leu Ser Glu Arg Asn Gln Leu Lys Ala Cys Met Gly Glu Leu Leu Asp
        690                 695                 700
Asn Phe Ser Cys Leu Ser Gln Glu Val Cys Arg Asp Ile Gln Ser Pro
705                 710                 715                 720
Glu Gln Ile Gln Ala Leu His Arg Tyr Cys Pro Val Leu Arg Pro Met
            725                 730                 735
Asp Leu Pro Thr Ala Ser Ser Ile Asn Pro Ala Pro Leu Gly Ala Glu
            740                 745                 750
Gln Asn Ile Ala Ala Ser Gln Cys Ala Val Gly Glu Asn Val Pro Cys
        755                 760                 765
Cys Leu Glu Pro Gly Ala Ala Pro Pro Gly Pro Trp Ala Pro Ser
    770                 775                 780
Asn Thr Ser Glu Asn Cys Thr Ser Gly Arg Arg Leu Glu Gly Thr Asp
785                 790                 795                 800
Pro Gly Thr Phe Ser Glu Arg Gly Pro Pro Leu Glu Pro Arg Ser Gln
                805                 810                 815
Thr Val Thr Val Asp Phe Cys Gln Glu Met Thr Asp Lys Cys Thr Thr
            820                 825                 830
Asp Glu Gln Pro Arg Lys Asp Tyr Thr Arg Ala Lys Ser Gly Ser
        835                 840                 845
Gly Glu Gly Arg Gly Ser Leu Leu Thr Cys Gly Asp Val Glu Glu Asn
    850                 855                 860
Pro Gly Pro Met Gly Ala Gly Ala Thr Gly Arg Ala Met Asp Gly Pro
865                 870                 875                 880
Arg Leu Leu Leu Leu Leu Leu Gly Val Ser Leu Gly Gly Ala Lys
                885                 890                 895
Glu Ala Cys Pro Thr Gly Leu Tyr Thr His Ser Gly Glu Cys Cys Lys
            900                 905                 910
Ala Cys Asn Leu Gly Glu Gly Val Ala Gln Pro Cys Gly Ala Asn Gln
        915                 920                 925
Thr Val Cys Glu Pro Cys Leu Asp Ser Val Thr Phe Ser Asp Val Val
    930                 935                 940
Ser Ala Thr Glu Pro Cys Lys Pro Cys Thr Glu Cys Val Gly Leu Gln
945                 950                 955                 960
Ser Met Ser Ala Pro Cys Val Glu Ala Asp Asp Ala Val Cys Arg Cys
                965                 970                 975
Ala Tyr Gly Tyr Tyr Gln Asp Glu Thr Thr Gly Arg Cys Glu Ala Cys
            980                 985                 990
Arg Val Cys Glu Ala Gly Ser Gly  Leu Val Phe Ser Cys  Gln Asp Lys
        995                 1000                1005
Gln Asn  Thr Val Cys Glu Glu  Cys Pro Asp Gly Thr  Tyr Ser Asp
    1010                1015                1020
Glu Ala  Asn His Val Asp Pro  Cys Leu Pro Cys Thr  Val Cys Glu
    1025                1030                1035
Asp Thr  Glu Arg Gln Leu Arg  Glu Cys Thr Arg Trp  Ala Asp Ala
    1040                1045                1050
Glu Cys  Glu Glu Ile Pro Gly  Arg Trp Ile Thr Arg  Ser Thr Pro
    1055                1060                1065
Pro Glu  Gly Ser Asp Ser Thr  Ala Pro Ser Thr Gln  Glu Pro Glu
    1070                1075                1080
```

```
Ala Pro  Pro Glu Gln Asp  Leu Ile Ala Ser  Thr Val Ala Gly Val
    1085         1090             1095

Val Thr  Thr Val Met Gly  Ser Ser Gln Pro  Val Val Thr Arg Gly
    1100         1105             1110

Thr Thr  Asp Asn Leu Ile  Pro Val Tyr Cys  Ser Ile Leu Ala Ala
    1115         1120             1125

Val Val  Val Gly Leu Val  Ala Tyr Ile Ala  Phe Lys Arg
    1130         1135             1140

<210> SEQ ID NO 11
<211> LENGTH: 3432
<212> TYPE: DNA
<213> ORGANISM: Homo sapiens

<400> SEQUENCE: 11
```

| | | | | | |
|---|---|---|---|---|---|
| atgagcgtgg | acgagaagcc | tgacagccct | atgtacgtgt | acgagagcac | cgtgcactgc | 60 |
| accaacatcc | tgctgggcct | gaacgaccag | cggaagaaag | acatcctgtg | cgacgtgacc | 120 |
| ctgatcgtgg | aacggaaaga | gttcagagcc | cacagagccg | tgctggccgc | ctgtagcgag | 180 |
| tatttttggc | aggccctcgt | gggccagacc | aagaacgatc | tggtggtgtc | cctgcctgag | 240 |
| gaagtgaccg | ccagaggatt | tggacccctg | ctgcagtttg | cctacaccgc | caaactgctg | 300 |
| ctgagccgcg | agaacatccg | gaagtgatc | agatgcgccg | agttcctgcg | gatgcacaac | 360 |
| ctggaagata | gctgcttcag | cttcctgcag | acccagctgc | tgaacagcga | ggatggcctg | 420 |
| ttcgtgtgca | gaaaggatgc | cgcctgtcag | aggcctcacg | aggactgcga | aaattctgcc | 480 |
| ggcgaggaag | aggacgaaga | ggaagaaacc | atggacagcg | agacagccaa | gatggcttgc | 540 |
| cccagggacc | agatgctgcc | tgagcctatc | tctttcgagg | ccgctgccat | tcctgtggcc | 600 |
| gagaaagaag | aagccctgct | gccagagcca | gacgtgccca | ccgatacaaa | agagagcagc | 660 |
| gagaaggacg | ccctgacaca | gtaccccaga | tacaagaagt | accagctggc | ctgcaccaag | 720 |
| aatgtgtaca | cgccagcag | ccacagcacc | agcggctttg | cctctaccct | cagagaggac | 780 |
| aacagcagca | acagcctgaa | gcctggactg | ccagaggcc | agatcaagtc | tgagcctcct | 840 |
| agcgaggaaa | atgaagagga | atctatcacc | ctgtgcctga | gcggcgacga | gcctgatgcc | 900 |
| aaagatagag | ctggcgacgt | ggaaatggac | cggaagcagc | cttctccagc | tcctacacct | 960 |
| acagctccag | ctggcgcagc | ctgcctggaa | agatcaagat | ctgtggctag | ccccagctgc | 1020 |
| ctgcggagcc | tgtttagcat | caccaagagc | gtggaactga | gcggcctgcc | tagcacatcc | 1080 |
| cagcagcact | tgccagatc | tcccgcctgt | cctttcgaca | aggaatcac | ccagggcgac | 1140 |
| ctgaaaaccg | actacacccc | tttcaccggc | aactacggac | agcctcacgt | gggacagaaa | 1200 |
| gaggtgtcca | actttaccat | gggcagccct | ctgagaggcc | caggacttga | ggccctgtgt | 1260 |
| aaacaagagg | gcgagctgga | tcggcggagc | gtgatctttt | ctagcagcgc | ctgtgaccag | 1320 |
| gtgtccacca | gcgtgcactc | ttacagcgga | gtgtccagcc | tggataagga | cctgtctgag | 1380 |
| cccgtgccta | aaggcctgtg | ggttggagct | ggacagagcc | tgccaagcag | ccaggcttat | 1440 |
| tctcacggcg | gactgatggc | cgatcatctg | cctggtagaa | tgcggcccaa | caccagctgt | 1500 |
| cccgtgccaa | tcaaagtgtg | ccctagaagc | cctcctctgg | aaacccggac | agaaccagc | 1560 |
| agcagctgtt | ccagctacag | ctatgccgag | gatggaagcg | gcggcagccc | ttgttcactg | 1620 |
| cctctgtgcg | agtttagcag | cagccccgt | tctcagggcg | ccagatttct | ggccaccgag | 1680 |
| catcaagaac | ctggcctgat | gggcgacggc | atgtacaatc | aagtgcggcc | ccagattaag | 1740 |

-continued

```
tgcgagcaga gctacggcac caacagctct gatgagagcg gcagctttag cgaggccgat    1800
agcgaaagct gccccgtgca ggatagaggc caagaagtga agctgccctt tccagtggat    1860
cagatcaccg acctgcctcg gaacgacttc cagatgatga tcaagatgca caagctgacc    1920
tccgagcagc tggaattcat ccacgacgtg cggcggagaa gcaagaacag aatcgctgcc    1980
cagcggtgcc ggaagagaaa gctggactgc atccagaatc tggaatgcga gatccggaag    2040
ctcgtgtgcg aaaaagagaa gctgctgtcc gagcggaacc agctgaaggc ctgtatggga    2100
gagctgctgg acaacttcag ctgtctgtct caagaagtgt gccgggacat ccagtctcca    2160
gagcagattc aggccctgca cagatactgc cctgtgctga ggcctatgga tctgcctaca    2220
gccagcagca tcaaccctgc tcctctggga gccgagcaga atattgccgc ctctcagtgt    2280
gccgtgggcg agaatgtgcc ttgctgtctt gaacctggcg ccgctcctcc tggacctcct    2340
tgggctcctt ctaacaccag cgagaactgc acctccggca aaggctggaa aggcacagat    2400
cctggcacct tcagcgaaag aggcccacca ctggaaccca gatctcagac cgtgaccgtg    2460
gacttctgcc aagagatgac cgacaagtgc accaccgacg agcagcccag aaaggactac    2520
accagggcca agagaagcgg aagtggagag ggaagaggct cccttctgac atgcggcgac    2580
gtggaggaga cccctggacc tatgggagct ggagctaccg aagagctat ggacggacca    2640
agacttctcc tgctcctcct gctgggtgtg agcctgggag gagctaagga ggcttgccct    2700
accggactgt acacccactc tggcgagtgc tgcaaggctt gcaacctggg agaggggagtg    2760
gctcaaccct gcggagctaa ccaaactgtc tgcgagcctt gcctggactc tgtgacattc    2820
tccgacgtgg tgtctgccac cgagccttgc aagccttgca ccgaatgcgt gggcctgcaa    2880
agcatgagcg ctccttgcgt ggaggctgac gacgctgtgt gccgatgcgc ttacggatac    2940
taccaagaca gaccaccgg aagatgcgag gcttgccgag tgtgcgaggc tggaagcgga    3000
ctcgtgttct cctgccaaga caagcaaaac accgtgtgtg aggaatgccc tgacggaacc    3060
tactccgacg aggctaacca cgtggaccct tgcctgcctt gcaccgtgtg tgaggacacc    3120
gagagacaac tgagggagtg cacaagatgg gctgacgctg agtgtgagga gatccctgga    3180
agatggatca caagatctac ccctcctgag ggaagcgact ccaccgctcc ttccacccaa    3240
gagcccgagg ctcctcctga gcaagacctg atcgcaagca ccgtggctgg agtggttaca    3300
accgtgatgg gaagctccca acccgtggtt acaagggga accaccgacaa cctgatccct    3360
gtgtactgct ccatcctggc tgctgtggtg gtgggattgg tggcctacat cgctttcaag    3420
agatgaatcg at                                                        3432
```

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12 gaaguggguga agcuccccuc                                                  20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cucuccccgg gagcaaaacc                                          20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
guuggcaggg augggcuuaa                                          20

<210> SEQ ID NO 15
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(5)
<223> OTHER INFORMATION: This region may encompass 1-5 residues
<220> FEATURE:
<221> NAME/KEY: SITE
<222> LOCATION: (1)..(50)
<223> OTHER INFORMATION: This sequence may encompass 1-5
      "(Gly)1-5(Ser)1-5" repeating units
<220> FEATURE:
<221> NAME/KEY: SITE
<222> LOCATION: (6)..(10)
<223> OTHER INFORMATION: This region may encompass 1-5 residues
<220> FEATURE:
<221> NAME/KEY: SITE
<222> LOCATION: (11)..(15)
<223> OTHER INFORMATION: This region may encompass 1-5 residues
<220> FEATURE:
<221> NAME/KEY: SITE
<222> LOCATION: (16)..(20)
<223> OTHER INFORMATION: This region may encompass 1-5 residues
<220> FEATURE:
<221> NAME/KEY: SITE
<222> LOCATION: (21)..(25)
<223> OTHER INFORMATION: This region may encompass 1-5 residues
<220> FEATURE:
<221> NAME/KEY: SITE
<222> LOCATION: (26)..(30)
<223> OTHER INFORMATION: This region may encompass 1-5 residues
<220> FEATURE:
<221> NAME/KEY: SITE
<222> LOCATION: (31)..(35)
<223> OTHER INFORMATION: This region may encompass 1-5 residues
<220> FEATURE:
<221> NAME/KEY: SITE
<222> LOCATION: (36)..(40)
<223> OTHER INFORMATION: This region may encompass 1-5 residues
<220> FEATURE:
<221> NAME/KEY: SITE
<222> LOCATION: (41)..(45)
<223> OTHER INFORMATION: This region may encompass 1-5 residues
<220> FEATURE:
<221> NAME/KEY: SITE
<222> LOCATION: (46)..(50)
<223> OTHER INFORMATION: This region may encompass 1-5 residues

<400> SEQUENCE: 15

Gly Gly Gly Gly Gly Ser Ser Ser Ser Ser Gly Gly Gly Gly Ser
1               5                   10                  15

Ser Ser Ser Ser Gly Gly Gly Gly Gly Ser Ser Ser Ser Ser Gly Gly
            20                  25                  30

```
Gly Gly Gly Ser Ser Ser Ser Ser Gly Gly Gly Gly Ser Ser Ser
            35                  40                  45
Ser Ser
    50
```

T CELLS WITH IMPROVED FUNCTIONALITY

CROSS-REFERENCES TO RELATED APPLICATIONS

This application claims the benefit of priority to U.S. Provisional Patent Application No. 63/070,174, filed 25 Aug. 2020 and titled "T CELLS WITH IMPROVED FUNCTIONALITY," the entirety of which is incorporated by reference herein.

TECHNICAL FIELD

The present disclosure relates to the field of cell therapy, and more specifically, to improving CAR and/or TCR T cell function by selected modulation of the expression of certain genes to increase T cell functionality.

SEQUENCE LISTING

This application incorporates by reference the Sequence Listing submitted in Computer Readable Form as file K-1090-US-NP SL.txt, created on Nov. 3, 2021 and containing 41,878 bytes.

BACKGROUND OF THE DISCLOSURE

Human cancers are comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Current therapies T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen.

Increasing the potencies of CAR-T cells could lead to improved therapeutic outcomes. It has been shown that less differentiated T cell are more potent in vivo due to their enhanced proliferative capacity (see e.g. Gattinoni et al., Nat. Medicine, 2011). By extension, the efficacy of CAR-T cells could be improved by providing CAR-T cells that are less differentiated. A need exists for increasing the efficacy of cells carrying chimeric antigen receptors (CARs) and engineered T cell receptors (TCRs).

SUMMARY

Disclosed is a modified immune cell (or a collected of such cells) engineered to inhibit the endogenous expression of one or more of Blimp-1 and A20, and/or express one or more of exogenous TCF7 and exogenous Bach2.

In certain embodiments, the modified immune cell comprises a deficient Blimp-1 gene and/or a deficient A20 gene. In certain embodiments, the deficient Blimp-1 gene and/or the deficient A20 gene is created by knockout. In certain embodiments, the deficient Blimp-1 gene and/or the deficient A20 is edited using CRISPR/Cas9, a zinc finger nuclease (ZFN), a TALEN, a MegaTAL, a meganuclease, Cpf1, homologous recombination, or a single stranded oligodeoxynucleotide (ssODN). In certain embodiments, the endogenous expression of one or more of Blimp-1 and A20 is inhibited by an exogenously introduced miRNA or an exogenously introduced siRNA.

In certain embodiments, the exogenous TCF7 comprises an amino acid sequence at least 75% identical to the amino acid sequence set forth as SEQ ID NO: 4.

In certain embodiments, the exogenous Bach2 comprises an amino acid sequence at least 75% identical to the amino acid sequence set forth as SEQ ID NO: 8.

In certain embodiments, the modified immune cell may further comprise a chimeric antigen receptor (CAR) or a T Cell receptor (TCR). In certain embodiments, the CAR binds to a tumor antigen comprising CD19, CD20, PSMA, PSMA, BCMA, TACI, CLL-1, CS1, or GPC3. In embodiments, the modified immune cell is a T cell.

In certain embodiments the modified immune cell is characterized by one or more of increased peak fold proliferation rate, increased CAR-mediated killing, increased cytokine production, or increased cellular characteristics associated with naïve phenotype. In certain embodiments, the cellular characteristics associated with naïve phenotype include the surface expression of one or more of, CD62L, CD127, CCR7, CD27, and CD45RA.

Disclosed is method of treating cancer, comprising administering to a subject in need thereof a therapeutically effective amount of a cell described herein.

Disclosed is method of increasing a peak fold proliferation rate of an immune cell, comprising: introducing an exogenous construct encoding a CAR or a TCR into the cell, and inhibiting the endogenous expression of one or more of Blimp-1 and A20 in the cell, and/or introducing an exogenous construct encoding one or more of TCF7 and Bach2 into the cell.

Disclosed is method of increasing a killing efficiency of an immune cell comprising: introducing an exogenous construct encoding a CAR or a TCR into the cell, and inhibiting the endogenous expression of one or more of Blimp-1 and A20 in the cell, and/or introducing an exogenous construct encoding one or more of TCF7 and Bach2 into the cell.

Disclosed is method of inducing cellular characteristics associated with naïve phenotype an immune cell, comprising: introducing an exogenous construct encoding a CAR or a TCR into the cell, and inhibiting the endogenous expression of one or more of Blimp-1 and A20 in the cell, and/or introducing an exogenous construct encoding one or more of TCF7 and Bach2 into the cell.

Disclosed is method of generating a modified immune cell, comprising: introducing an exogenous construct encoding a CAR or a TCR into the cell, and inhibiting the endogenous expression of one or more of Blimp-1 and A20 in the cell, and/or introducing an exogenous construct encoding one or more of TCF7 and Bach2 into the cell.

In embodiments, inhibiting the endogenous expression one or more of Blimp-1 and A20 comprises editing a gene locus to eliminate expression of endogenous Blimp-1 and/or A20.

In embodiments, editing a gene locus comprises using a CRISPR/Cas9, a zinc finger nuclease (ZFN), a TALEN, a MegaTAL, a meganuclease, Cpf1, homologous recombination, or a single stranded oligodeoxynucleotide (ssODN).

In embodiments, inhibiting the endogenous expression of one or more of Blimp-1 and A20 and comprises expression of an exogenous miRNA or an exogenous siRNA that specifically targets Blimp-1 and/or expression of an exogenous miRNA or an exogenous siRNA that specifically targets A20.

In embodiments, the exogenous TCF7 comprises an amino acid sequence at least 75% identical to the amino acid sequence set forth as SEQ ID NO: 4.

In embodiments, the exogenous Bach2 comprises an amino acid sequence at least 75% identical to the amino acid sequence set forth as SEQ ID NO: 8.

In embodiments, the cell is a T cell.

DETAILED DESCRIPTION OF THE DISCLOSURE

The present disclosure relates to methods of modulating the expression of transcription factors and other cellular proteins, for example decreasing expression of some genes, and increasing the expression of other genes. The modulation of expression of certain genes upon stimulation and activation increases the cellular characteristics associated with naïve phenotype, proliferation, and/or functional properties in CAR-mediated killing and/or cytokine production. These cellular enhancements may further increase the peak expansion of CAR T cells. While not being bound by theory, increasing the peak expansion of CAR T cells may increase the efficacy of CAR T cells in the treatment of cancer, for example by increasing the killing efficiency of the CART calls. Some aspects of the disclosure relate increasing the expression of one or more of Bach2 and TCF7, for example from an exogenously introduced source. The present disclosure also provides vectors (e.g., viral vectors) comprising nucleic acids that encode Bach2 and/or TCF7 (or a functional fragment thereof) and compositions comprising such vectors. Some aspects of the disclosure relate to agents that inhibit the expression of one or more of Blimp-1, and A20. The present disclosure also relates to nucleic acids encoding such agents, for example agents that inhibit the expression of one or more of Blimp-1, and A20 when introduced into an immune cell. The present disclosure also provides vectors (e.g., viral vectors) comprising such nucleic acids and compositions comprising such vectors.

The present disclosure additionally provides engineered cells (e.g., T cells) comprising such nucleic acids (for example nucleic acids that encode Bach2 and/or TCF7 and/or nucleic acids encoding agents that inhibit the expression of one or more of Blimp-1, and A20) and/or transduced with such viral vectors and compositions comprising such engineered cells, which in certain cases include one or more expressed CARs or T cell receptors (TCRs). The present disclosure provides compositions (e.g., pharmaceutical compositions) including a plurality of engineered cells (e.g., engineered T cells). Other aspects of the disclosure relate to cells in which the expression of Blimp-1, and A20, is reduced and/or inhibited and/or the expression Bach2 and TCF7 is increased, and their use in a T cell therapy, such as CAR T cell therapy for the treatment of a patient suffering from a cancer. The present disclosure provides methods for manufacturing such engineered cells and compositions and uses (e.g., in treating a cancer) of such engineered cells and compositions. And, the present disclosure provides a method of inducing an immunity against a tumor comprising administering to a subject an effective amount of a cell comprising a polynucleotide, a vector, or a polypeptide of the present disclosure.

Any aspect or embodiment described herein may be combined with any other aspect or embodiment as disclosed herein. While the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims. The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, dictionaries, documents, manuscripts and scientific literature cited herein are hereby incorporated by reference. Other features and advantages of the disclosure will be apparent from the following Detailed Description, comprising the Examples, and the claims.

TERMS

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "e.g.," as used herein, is used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Systeme International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", $2^{nd}$ ed., (2001), CRC Press; "The Dictionary of Cell & Molecular Biology", $5^{th}$ ed., (2013), Academic Press; and "The Oxford Dictionary Of Biochemistry And Molecular Biology", Cammack et al. eds., $2^{nd}$ ed, (2006), Oxford University Press, provide those of skill in the art with a general dictionary for many of the terms used in this disclosure.

"A20" Tumor necrosis factor, alpha-induced protein 3 or A20 is a protein is encoded by the TNFAIP3 gene. This gene was identified as a gene whose expression is rapidly induced by the tumor necrosis factor (TNF). A20 is a zinc finger protein and a deubiquitinating enzyme, and has been shown to inhibit NF-kappa B activation as well as TNF-mediated apoptosis. Details of A20 including the nucleic acid and amino acid sequences can be found on the NCBI website; Gene ID: 7128, updated on 22 Jul. 2020, which is specifically incorporated herein by reference.

"Administering" refers to the physical introduction of an agent to a subject, such as a modified T cell disclosed herein, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The terms, "activated" and "activation" refer to the state of a T cell that has been sufficiently stimulated to induce detectable cellular proliferation. In one embodiment, activation may also be associated with induced cytokine production, and detectable effector functions. The term "activated T cells" refers to, among other things, T cells that are proliferating. Signals generated through the TCR alone may be insufficient for full activation of the T cell and one or more secondary or costimulatory signals may also be required. Thus, T cell activation comprises a primary stimulation signal through the TCR/CD3 complex and one or more secondary costimulatory signals. Costimulation may be evidenced by proliferation and/or cytokine production by T cells that have received a primary activation signal, such as stimulation through the TCR/CD3 complex.

The term "agent" may refer to a molecule or entity of any class comprising, or a plurality of molecules or entities, any of which may be, for example, a polypeptide, nucleic acid, saccharide, lipid, small molecule, metal, cell (such as a T cell), or organism (for example, a fraction or extract thereof) or component thereof. In some embodiments, an agent may be utilized in isolated or pure form. In some embodiments, an agent may be utilized in a crude or impure form. In some embodiments, an agent may be provided as a population, collection, or library, for example that may be screened to identify or characterize members present therein.

The term "allogeneic" refers to any material derived from one individual which is then introduced to another individual of the same species, e.g., allogeneic T cell transplantation.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (Clq) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the CH2 domain.

The term "human antibody" is intended to comprise antibodies having variable and constant domain sequences generated, assembled, or derived from human immunoglobulin sequences, or sequences indistinguishable therefrom. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof), camelid antibodies, single chain or Tandem diabodies (TandAb®), Anticalins®, Nanobodies® minibodies, BiTE®s, ankyrin repeat proteins or DARPINs®, Avimers®, DARTs, TCR-like antibodies, Adnectins®, Affilins®, Transbodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen binding fragment or an antigen-binding portion of any of the aforementioned immunoglobulins, and includes a monovalent and a divalent fragment or portion, and a single chain Ab.

An "antigen binding molecule," "antigen binding portion," "antigen binding fragment," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments an antigen binding molecule is a chimeric antigen receptor (CAR) or a engineered T cell receptor (TCR). In certain embodiments, the antigen binding molecule binds to 2B4 (CD244), 4-1BB, 5T4, A33 antigen, adenocarcinoma antigen, adrenoceptor beta 3 (ADRB3), A kinase anchor protein 4 (AKAP-4), alpha-fetoprotein (AFP), anaplastic lymphoma kinase (ALK), Androgen receptor, B7H3 (CD276), β2-integrins, BAFF, B-lymphoma cell, B cell maturation antigen (BCMA), bcr-abl (oncogene fusion protein consisting of breakpoint cluster region (BCR) and Abelson murine leukemia viral oncogene homolog 1 (Abl), BhCG, bone marrow stromal cell antigen 2 (BST2), CCCTC-Binding Factor (Zinc Finger Protein)-Like (BORIS or Brother of the Regulator of Imprinted Sites), BST2, C242 antigen, 9-0-acetyl-CA19-9 marker, CA-125, CAEX, calreticulin, carbonic anhydrase 9 (CAIX), C-MET, CCR4, CCR5, CCR8, CD2, CD3, CD4, CD5, CD8, CD7, CD10, CD16, CD19, CD20, CD22, CD23 (IgE receptor), CD24, CD25, CD27, CD28, CD30 (TNFRSF8), CD33, CD34, CD38, CD40, CD40L, CD41, CD44, CD44V6, CD49f, CD51, CD52, CD56, CD63, CD70, CD72, CD74, CD79a, CD79b, CD80, CD84, CD96, CD97, CD100, CD123, CD125, CD133, CD137, CD138, CD150, CD152 (CTLA-4), CD160, CD171, CD179a, CD200, CD221, CD229, CD244, CD272 (BTLA), CD274 (PDL-1, B7H1), CD279 (PD-1), CD352, CD358, CD300 molecule-like family member f (CD300LF), Carcinoembryonic antigen (CEA), claudin 6 (CLDN6), C-type lectin-like molecule-1 (CLL-1 or CLECL1), C-type lectin domain family 12 member A (CLEC12A), a cytomegalovirus (CMV) infected cell antigen, CNT0888, CRTAM (CD355), CS-1 (also referred to as CD2 subset 1, CRACC, CD319, and 19A24), CTLA-4, Cyclin B 1, chromosome X open reading frame 61 (CX-ORF61), Cytochrome P450 1B 1 (CYP1B1), DNAM-1 (CD226), desmoglein 4, DR3, DR5, E-cadherin neoepitope, epidermal growth factor receptor (EGFR), EGF1R, epidermal growth factor receptor variant III (EGFRvIII), epithelial glycoprotein-2 (EGP-2), epithelial glycoprotein-40 (EGP-40), EGF-like module-containing mucin-like hormone receptor-like 2 (EMR2), elongation factor 2 mutated (ELF2M), endosialin, Epithelial cell adhesion molecule (EPCAM), ephrin type-A receptor 2 (EphA2), Ephrin B2, receptor tyrosine-protein kinases erb-B2,3,4 (erb-B2,3,4), ERBB, ERBB2 (Her2/neu), ERG (transmembrane protease, serine 2 (TMPRSS2) ETS fusion gene), ETA, ETS translocation-variant gene 6, located on chromosome 12p (ETV6-AML), Fc fragment of IgA receptor (FCAR or CD89), fibroblast activation protein alpha (FAP), FBP, Fc receptor-like 5 (FCRL5), fetal acetylcholine receptor (AChR), fibronectin extra domain-B, Fms-Like Tyrosine Kinase 3 (FLT3), folate-binding protein (FBP), folate receptor 1, folate receptor a, Folate receptor (3, Fos-related antigen 1, Fucosyl, Fucosyl GM1; GM2, ganglioside G2 (GD2), ganglioside GD3 (aNeu5Ac(2-8)aNeu5Ac(2-3)bDGalp(1-4) bDG1cp(1-1)Cer), o-acetyl-GD2 ganglioside (OAcGD2), GITR (TNFRSF 18), GM1, ganglioside GM3 (aNeu5Ac(2-3)bDGalp(1-4)bDG1cp(1-1)Cer), GP 100, hexasaccharide portion of globoH glycoceramide (GloboH), glycoprotein 75, Glypican-3 (GPC3), glycoprotein 100 (gplOO), GPNMB, G protein-coupled receptor 20 (GPR20), G protein-coupled receptor class C group 5, member D (GPRC5D), Hepatitis A virus cellular receptor 1 (HAVCR1), human Epidermal Growth Factor Receptor 2 (HER-2), HER2/neu, HER3, HER4, HGF, high molecular weight-melanoma-associated antigen (HMWMAA), human papilloma virus E6 (HPV E6), human papilloma virus E7 (HPV E7), heat shock protein 70-2 mutated (mut hsp70-2), human scatter factor receptor kinase, human Telomerase reverse transcriptase (hTERT), HVEM, ICOS, insulin-like growth factor receptor 1 (IGF-1 receptor), IGF-I, IgG1, immunoglobulin lambda-like polypeptide 1 (IGLL1), IL-6, Interleukin 11 receptor alpha (IL-11Ra), IL-13, Interleukin-13 receptor subunit alpha-2 (IL-13Ra2 or CD213A2), insulin-like growth factor I receptor (IGF1-R), integrin α5β1, integrin αvβ3, intestinal carboxyl esterase, κ-light chain, KCS1, kinase insert domain receptor (KDR), KIR, KIR2DL1, KIR2DL2, KIR2DL3, KIR3DL2, KIR-L, KG2D ligands, KIT (CD117), KLRGI, LAGE-1a, LAG3, lymphocyte-specific protein tyrosine kinase (LCK), Leukocyte immunoglobulin-like receptor subfamily A member 2 (LILRA2), legumain, Leukocyte-associated immunoglobulin-like receptor 1 (LAIR1), Lewis(Y) antigen, LeY, LG, LI cell adhesion molecule (LI-CAM), LIGHT, LMP2, lymphocyte antigen 6 complex, LTBR, locus K 9 (LY6K), Ly-6, lymphocyte antigen 75 (LY75), melanoma cancer testis antigen-1 (MAD-CT-1); melanoma cancer testis antigen-2 (MAD-CT-2), MAGE, Melanoma-associated antigen 1 (MAGE-A1), MAGE-A3 melanoma antigen recognized by T cells 1 (MelanA or MARTI), MelanA/MART1, Mesothelin, MAGE A3, melanoma inhibitor of apoptosis (ML-IAP), melanoma-specific chondroitin-sulfate proteoglycan (MCSCP), MORAb-009, MS4A1, Mucin 1 (MUC1), MUC2, MUC3, MUC4, MUCSAC, MUC5b, MUC7, MUC16, mucin CanAg, Mullerian inhibitory substance (MIS) receptor type II, v-myc avian myelocytomatosis viral oncogene neuroblastoma derived homolog (MYCN), N-glycolylneuraminic acid, N-Acetyl glucosaminyl-transferase V (NA17), neural cell adhesion molecule (NCAM), NKG2A, NKG2C, NKG2D, NKG2E ligands, NKR-P IA, NPC-1C, NTB-A, mammary gland differentiation antigen (NY-BR-1), NY-ESO-1, oncofetal antigen (h5T4), Olfactory receptor 51E2 (OR51E2), OX40, plasma cell antigen, poly SA, proacrosin binding protein sp32 (OY-TES 1), p53, p53 mutant, pannexin 3 (PANX3), prostatic acid phosphatase (PAP), paired box protein Pax-3 (PAX3), Paired box protein Pax-5 (PAX5), prostate carcinoma tumor antigen-1 (PCTA-1 or Galectin 8), PD-1H, Platelet-derived growth factor receptor alpha (PDGFR-alpha), PDGFR-beta, PDL192, PEN-5, phosphatidylserine, placenta-specific 1 (PLAC1), Polysialic acid, Prostase, prostatic carcinoma cells, prostein, Protease Serine 21 (Testisin or PRSS21), Proteinase3 (PR1), prostate stem cell antigen (PSCA), prostate-specific membrane antigen (PSMA), Proteasome (Prosome, Macropain) Subunit, Beta Type, Receptor for Advanced Glycation Endproducts (RAGE-1), RANKL, Ras mutant, Ras Homolog Family Member C (RhoC), RON, Receptor tyrosine kinase-like orphan receptor 1 (ROR1), renal ubiquitous 1 (RU1), renal ubiquitous 2 (RU2), sarcoma translocation breakpoints, Squamous Cell Carcinoma Antigen Recognized By T Cells 3 (SART3), SAS, SDC1, SLAMF7, sialyl Lewis adhesion molecule (sLe), Siglec-3, Siglec-7, Siglec-9, sonic hedgehog (SHH), sperm protein 17 (SPA17), Stage-specific embryonic antigen-4 (SSEA-4), STEAP, sTn antigen, synovial sarcoma, X breakpoint 2 (SSX2), Survivin, Tumor-associated glycoprotein 72 (TAG72), TCR5y, TCRa, TCRB, TCR Gamma Alternate Reading Frame Protein (TARP), telomerase, TIGIT TNF-α precursor, tumor endothelial marker 1 (TEM1/CD248), tumor endothelial marker 7-related (TEM7R), tenascin C, TGF beta 2, TGF-β, transglutaminase 5 (TGS5), angiopoietin-binding cell surface receptor 2 (Tie 2), TIM1, TIM2, TIM3, Tn Ag, TRAIL-R1, TRAIL-R2, Tyrosinase-related protein 2 (TRP-2), thyroid stimulating hormone receptor (TSHR), tumor antigen CTAA16.88, Tyrosinase, ROR1, TAG-72, uroplakin 2 (UPK2), VEGF-A, VEGFR-1, vascular endothelial growth factor receptor 2 (VEGFR2), and vimentin, Wilms tumor protein (WT1), or X Antigen Family, Member 1A (XAGE1). Amino acid sequences that specifically bind to said antigens are known in the art or may be prepared using methods known in the art; examples include immunoglobulins, variable regions of immunoglobulins (e.g. variable fragment ("Fv") or bivalent variable fragment ("Fab")), single chain antibodies, etc. In certain embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

In some instances, a CDR is substantially identical to one found in a reference antibody (e.g., an antibody of the present disclosure) and/or the sequence of a CDR provided in the present disclosure. In some embodiments, a CDR is substantially identical to a reference CDR (e.g., a CDR provided in the present disclosure) in that it is either identical in sequence or contains between 1, 2, 3, 4, or 5 (e.g., 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g., 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody. In various embodiments, an antigen binding fragment cross-competes with the reference antibody, for example, binding to substantially the same or identical epitope as the reference antibody An antigen binding fragment may be produced by any means. For example, in some embodiments, an antigen binding fragment may be enzymatically or chemically produced by fragmentation of an intact antibody. In some embodiments, an antigen binding fragment may be recombinantly produced (such as by expression of an engineered nucleic acid sequence). In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term "variable region" or "variable domain" is used interchangeably. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

| CDR Numbering | | | | |
|---|---|---|---|---|
| Loop | Kabat | AbM | Chothia | Contact |
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B (Kabat Numbering) | H26-H35B | H26-H32 . . . 34 | H30-H35B |
| H1 | H31-H35 (Chothia Numbering) | H26-H35 | H26-H32 | H30-H35 |
| H2 | H50-H65 | H50-H58 | H52-H56 | H47-H58 |
| H3 | H95-H102 | H95-H102 | H95-H102 | H93-H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat EA & Wu TT (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG$_1$, IgG$_2$, IgG$_3$ and IgG$_4$.

The term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

An "antigen" refers to a compound, composition, or substance that may stimulate the production of antibodies or a T cell response in a human or animal, including compositions (such as one that includes a tumor-specific protein) that are injected or absorbed into a human or animal. An antigen reacts with the products of specific humoral or cellular immunity, including those induced by heterologous antigens, such as the disclosed antigens. A "target antigen" or "target antigen of interest" is an antigen that is not substantially found on the surface of other normal (desired) cells and to which a binding domain of a TCR or CAR contemplated herein, is designed to bind. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is all or a fragment of 2B4 (CD244), 4-1BB, 5T4, A33 antigen, adenocarcinoma antigen, adrenoceptor beta 3 (ADRB3), A kinase anchor protein 4 (AKAP-4), alpha-fetoprotein (AFP), anaplastic lymphoma kinase (ALK), Androgen receptor, B7H3 (CD276), β2-integrins, BAFF, B-lymphoma cell, B cell maturation antigen (BCMA), bcr-abl (oncogene fusion protein consisting of breakpoint cluster region (BCR) and Abelson murine leukemia viral oncogene homolog 1 (Abl), BhCG, bone marrow stromal cell antigen 2 (BST2), CCCTC-Binding Factor (Zinc Finger Protein)-Like (BORIS or Brother of the Regulator of Imprinted Sites), BST2, C242 antigen, 9-0-acetyl-CA19-9 marker, CA-125, CAEX, calreticulin, carbonic anhydrase 9 (CAIX), C-MET, CCR4, CCR5, CCR8, CD2, CD3, CD4, CD5, CD8, CD7, CD10, CD16, CD19, CD20, CD22, CD23 (IgE receptor), CD24, CD25, CD27, CD28, CD30 (TNFRSF8), CD33, CD34, CD38, CD40, CD40L, CD41, CD44, CD44V6, CD49f, CD51, CD52, CD56, CD63, CD70, CD72, CD74, CD79a, CD79b, CD80, CD84, CD96, CD97, CD100, CD123, CD125, CD133, CD137, CD138, CD150, CD152 (CTLA-4), CD160, CD171, CD179a, CD200, CD221, CD229, CD244, CD272 (BTLA), CD274 (PDL-1, B7H1), CD279 (PD-1), CD352, CD358, CD300 molecule-like family member f (CD300LF), Carcinoembryonic antigen (CEA), claudin 6 (CLDN6), C-type lectin-like molecule-1 (CLL-1 or CLECL1), C-type lectin domain family 12 member A (CLEC12A), a cytomegalovirus (CMV) infected cell antigen, CNT0888, CRTAM (CD355), CS-1 (also referred to as CD2 subset 1, CRACC, CD319, and 19A24), CTLA-4, Cyclin B 1, chromosome X open reading frame 61 (CXORF61), Cytochrome P450 1B 1 (CYP1B1), DNAM-1 (CD226), desmoglein 4, DR3, DR5, E-cadherin neoepitope, epidermal growth factor receptor (EGFR), EGF1R, epidermal growth factor receptor variant III (EGFRvIII), epithelial glycoprotein-2 (EGP-2), epithelial glycoprotein-40 (EGP-40), EGF-like module-containing mucin-like hormone receptor-like 2 (EMR2), elongation factor 2 mutated (ELF2M), endosialin, Epithelial cell adhesion molecule (EPCAM), ephrin type-A receptor 2 (EphA2), Ephrin B2, receptor tyrosine-protein kinases erb-B2,3,4 (erb-B2,3,4), ERBB, ERBB2 (Her2/neu), ERG (transmembrane protease, serine 2 (TMPRSS2) ETS fusion gene), ETA, ETS translocation-variant gene 6, located on chromosome 12p (ETV6-AML), Fc fragment of IgA receptor (FCAR or CD89), fibroblast activation protein alpha (FAP), FBP, Fc receptor-like 5 (FCRL5), fetal acetylcholine receptor (AChR), fibronectin extra domain-B, Fms-Like Tyrosine Kinase 3 (FLT3), folate-binding protein (FBP), folate receptor 1, folate receptor a, Folate receptor (3, Fos-related antigen 1, Fucosyl, Fucosyl GM1; GM2, ganglioside G2 (GD2), ganglioside GD3 (aNeu5Ac(2-8)aNeu5Ac(2-3)bD-Galp(1-4)bDG1cp(1-1)Cer), o-acetyl-GD2 ganglioside (OAcGD2), GITR (TNFRSF 18), GM1, ganglioside GM3 (aNeu5Ac(2-3)bDGalp(1-4)bDG1cp(1-1)Cer), GP 100, hexasaccharide portion of globoH glycoceramide (GloboH), glycoprotein 75, Glypican-3 (GPC3), glycoprotein 100 (gplOO), GPNMB, G protein-coupled receptor 20 (GPR20), G protein-coupled receptor class C group 5, member D (GPRC5D), Hepatitis A virus cellular receptor 1 (HAVCR1), human Epidermal Growth Factor Receptor 2 (HER-2), HER2/neu, HER3, HER4, HGF, high molecular weight-melanoma-associated antigen (HMWMAA), human papilloma virus E6 (HPV E6), human papilloma virus E7 (HPV E7), heat shock protein 70-2 mutated (mut hsp70-2), human scatter factor receptor kinase, human Telomerase reverse transcriptase (hTERT), HVEM, ICOS, insulin-like growth factor receptor 1 (IGF-1 receptor), IGF-I, IgG1, immunoglobulin lambda-like polypeptide 1 (IGLL1), IL-6, Interleukin 11 receptor alpha (IL-11Ra), IL-13, Interleukin-13 receptor subunit alpha-2 (IL-13Ra2 or CD213A2), insulin-like growth factor I receptor (IGF1-R), integrin α5β1, integrin αvβ3, intestinal carboxyl esterase, κ-light chain, KCS1, kinase insert domain receptor (KDR), KIR, KIR2DL1, KIR2DL2, KIR2DL3, KIR3DL2, KIR-L, KG2D ligands, KIT (CD117), KLRGI, LAGE-1a, LAG3, lymphocyte-specific protein tyrosine kinase (LCK), Leukocyte immunoglobulin-like receptor subfamily A member 2 (LILRA2), legumain, Leukocyte-associated immunoglobulin-like receptor 1 (LAIRD, Lewis(Y) antigen, LeY, LG, LI cell adhesion molecule (LI-CAM), LIGHT, LMP2, lymphocyte antigen 6 complex, LTBR, locus K 9 (LY6K), Ly-6, lymphocyte antigen 75 (LY75), melanoma cancer testis antigen-1 (MAD-CT-1); melanoma cancer testis antigen-2 (MAD-CT-2), MAGE, Melanoma-associated antigen 1 (MAGE-A1), MAGE-A3 melanoma antigen recognized by T cells 1 (MelanA or MARTI), MelanA/MART1, Mesothelin, MAGE A3, melanoma inhibitor of apoptosis (ML-IAP), melanoma-specific chondroitin-sulfate proteoglycan (MCSCP), MORAb-009, MS4A1, Mucin 1 (MUC1), MUC2, MUC3, MUC4, MUCSAC, MUC5b, MUC7, MUC16, mucin CanAg, Mullerian inhibitory substance (MIS) receptor type II, v-myc avian myelocytomatosis viral oncogene neuroblastoma derived homolog (MYCN), N-glycolylneuraminic acid, N-Acetyl glucosaminyl-transferase V (NA17), neural cell adhesion molecule (NCAM), NKG2A, NKG2C, NKG2D, NKG2E ligands, NKR-P IA, NPC-1C, NTB-A, mammary gland differentiation antigen (NY-BR-1), NY-ESO-1, oncofetal antigen (h5T4), Olfactory receptor 51E2 (OR51E2), OX40, plasma cell antigen, poly SA, proacrosin binding protein sp32 (OY-TES 1), p53, p53 mutant, pannexin 3 (PANX3), prostatic acid phosphatase (PAP), paired box protein Pax-3 (PAX3), Paired box protein Pax-5 (PAX5), prostate carcinoma tumor antigen-1 (PCTA-1 or Galectin 8), PD-1H, Platelet-derived growth factor receptor alpha (PDGFR-alpha), PDGFR-beta, PDL192, PEN-5, phosphatidylserine, placenta-specific 1 (PLAC1), Polysialic acid, Prostase, prostatic carcinoma cells, prostein, Protease Serine 21 (Testisin or PRSS21), Proteinase3 (PR1), prostate stem cell antigen (PSCA), prostate-specific membrane antigen (PSMA), Proteasome (Prosome, Macropain) Subunit, Beta Type, Receptor for Advanced Glycation Endproducts (RAGE-1), RANKL, Ras mutant, Ras Homolog Family Member C (RhoC), RON, Receptor tyrosine kinase-like orphan receptor 1 (ROR1), renal ubiquitous 1 (RU1), renal ubiquitous 2 (RU2), sarcoma translocation breakpoints, Squamous Cell Carcinoma Antigen Recognized By T Cells 3 (SART3), SAS, SDC1, SLAMF7, sialyl Lewis adhesion molecule (sLe), Siglec-3, Siglec-7, Siglec-9, sonic hedgehog (SHH), sperm protein 17 (SPA17), Stage-specific embryonic antigen-4 (SSEA-4), STEAP, sTn antigen, synovial sarcoma, X breakpoint 2 (SSX2), Survivin, Tumor-associated glycoprotein 72 (TAG72), TCR5y, TCRa, TCRB, TCR Gamma Alternate Reading Frame Protein (TARP), telomerase, TIGIT TNF-α precursor, tumor endothelial marker 1 (TEM1/CD248), tumor endothelial marker 7-related (TEM7R), tenascin C, TGF beta 2, TGF-β, transglutaminase 5 (TGS5), angiopoietin-binding cell surface receptor 2 (Tie 2), TIM1, TIM2, TIM3, Tn Ag, TRAIL-R1, TRAIL-R2, Tyrosinase-related protein 2 (TRP-2), thyroid stimulating hormone receptor (TSHR), tumor antigen CTAA16.88, Tyrosinase, ROR1, TAG-72, uroplakin 2 (UPK2), VEGF-A, VEGFR-1, vascular endothelial growth factor receptor 2 (VEGFR2), and vimentin, Wilms tumor protein (WT1), or X Antigen Family, Member 1A (XAGE1). A "target" is any molecule bound by a binding motif, antigen binding system, CAR or antigen binding agent, e.g., an antibody.

"Antigen-specific targeting region" (ASTR) refers to the region of the CAR which targets specific antigens. The targeting regions on the CAR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of this disclosure. In fact, almost any molecule that binds a given antigen with high affinity can be used as an antigen-specific targeting region, as will be appreciated by those of skill in the art.

"Antigen presenting cell" or "APC" refers to cells that process and present antigens to T cells. Exemplary APCs comprise dendritic cells, macrophages, B cells, certain activated epithelial cells, and other cell types capable of TCR stimulation and appropriate T cell costimulation.

An "anti-tumor effect" refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

Two events or entities are "associated" with one another if the presence, level, and/or form of one is correlated with that of the other. For example, an entity (e.g., polypeptide, genetic signature, metabolite, microbe, etc.) is considered to be associated with a disease, disorder, or condition, if its presence, level, and/or form correlates with incidence of and/or susceptibility to the disease, disorder, or condition (e.g., across a relevant population). For example, two or more entities are physically "associated" with one another if they interact, directly or indirectly, so that they are and/or remain in physical proximity with one another (e.g., bind). In additional examples, two or more entities that are physically associated with one another are covalently linked or connected to one another, or non-covalently associated, for example by means of hydrogen bonds, van der Waals interaction, hydrophobic interactions, magnetism, and combinations thereof.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

"Bach2" (BTB Domain and CNC Homolog 2) is a transcription factor that is a regulator of adaptive immunity and the maintenance of regulatory T cell function and B-cell maturation. Bach2 is a basic leucine zipper (bZIP) transcription factors that are includes a conserved 43-amino acid region (called the CNC domain) located N-terminal to the bZIP DNA-binding domain. In addition, Bach2 contains a BTB domain (Broad complex-Tramtrack-Bric-a-brac domain, also known as the POZ [poxvirus and zinc finger] domain) that is absent in other CNC proteins. Dimerization of leucine zippers creates a pair of the adjacent basic regions that bind DNA and undergo conformational change. Details of Bach2 including nucleic acid and amino acid sequences can be found on the NCBI website; Gene ID: 60468, updated on 22 Jul. 2020, which is specifically incorporated herein by reference.

"Binding affinity" generally refers to the strength of the sum total of non-covalent interactions between a single binding site of a molecule (e.g., an antibody) and its binding partner (e.g., an antigen). Unless indicated otherwise "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIACORE® or KinExA.

The term "KD" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec −1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M−1×sec−1 or 1/M) refers to the association rate constant of a particular antibody-antigen interaction, or the association rate constant of an antibody or antibody-binding fragment.

The term "$K_A$" (M−1 or 1/M) refers to the association equilibrium constant of a particular antibody-antigen interaction, or the association equilibrium constant of an antibody or antibody binding fragment. The association equilibrium constant is obtained by dividing the $k_a$ by the $k_d$.

The term "binding" generally refers to a non-covalent association between or among two or more entities. Direct binding involves physical contact between entities or moieties. "Indirect" binding involves physical interaction by way of physical contact with one or more intermediate entities. Binding between two or more entities may be assessed in any of a variety of contexts, e.g., where interacting entities or moieties are studied in isolation or in the context of more complex systems (e.g., while covalently or otherwise associated with a carrier entity and/or in a biological system such as a cell).

The terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen. Binding may comprise preferential association of a binding motif, antibody, or antigen binding system with a target of the binding motif, antibody, or antigen binding system as compared to association of the binding motif, antibody, or antigen binding system with an entity that is not the target (i.e. non-target). In some embodiments, a binding motif, antibody, or antigen binding system selectively binds a target if binding between the binding motif, antibody, or antigen binding system and the target is greater than 2-fold, greater than 5-fold, greater than 10-fold, 20-fold, 30-fold, 40-fold, 50-fold, 60-fold, 70-fold, 80-fold, 90-fold, or greater than 100-fold as compared with binding of the binding motif, antibody, or antigen binding system and a non-target. In some embodiments, a binding motif, antibody, or antigen binding system selectively binds a target if the binding affinity is less than about $10^{-5}$ M, less than about $10^{-6}$ M, less than about 10 M, less than about $10^{-8}$ M, or less than about $10^{-9}$ M.

In another embodiment, molecules that specifically bind to an antigen bind with a dissociation constant ($K_d$) of about $1 \times 10^{-7}$ M. In some embodiments, the antigen binding molecule specifically binds an antigen with "high affinity" when the $K_d$ is about $1 \times 10^{-9}$ M to about $5 \times 10^{-9}$ M. In some embodiments, the antigen binding molecule specifically binds an antigen with "very high affinity" when the $K_d$ is $1 \times 10^{-10}$ M to about $5 \times 10^{-10}$ M. In one embodiment, the antigen binding molecule has a $K_d$ of $10^{-9}$ M. In one embodiment, the off-rate is less than about $1 \times 10^{-5}$. In embodiments, the antigen binding molecule binds 2B4 (CD244), 4-1BB, 5T4, A33 antigen, adenocarcinoma antigen, adrenoceptor beta 3 (ADRB3), A kinase anchor protein 4 (AKAP-4), alpha-fetoprotein (AFP), anaplastic lymphoma kinase (ALK), Androgen receptor, B7H3 (CD276), β2-integrins, BAFF, B-lymphoma cell, B cell maturation antigen (BCMA), bcr-abl (oncogene fusion protein consisting of breakpoint cluster region (BCR) and Abelson murine leukemia viral oncogene homolog 1 (Abl), BhCG, bone marrow stromal cell antigen 2 (BST2), CCCTC-Binding Factor (Zinc Finger Protein)-Like (BORIS or Brother of the Regulator of Imprinted Sites), BST2, C242 antigen, 9-0-acetyl-CA19-9 marker, CA-125, CAEX, calreticulin, carbonic anhydrase 9 (CAIX), C-MET, CCR4, CCR5, CCR8, CD2, CD3, CD4, CD5, CD8, CD7, CD10, CD16, CD19, CD20, CD22, CD23 (IgE receptor), CD24, CD25, CD27, CD28, CD30 (TNFRSF8), CD33, CD34, CD38, CD40, CD40L, CD41, CD44, CD44V6, CD49f, CD51, CD52, CD56, CD63, CD70, CD72, CD74, CD79a, CD79b, CD80, CD84, CD96, CD97, CD100, CD123, CD125, CD133, CD137, CD138, CD150, CD152 (CTLA-4), CD160, CD171, CD179a, CD200, CD221, CD229, CD244, CD272 (BTLA), CD274 (PDL-1, B7H1), CD279 (PD-1), CD352, CD358, CD300 molecule-like family member f (CD300LF), Carcinoembryonic antigen (CEA), claudin 6 (CLDN6), C-type lectin-like molecule-1 (CLL-1 or CLECL1), C-type lectin domain family 12 member A (CLEC12A), a cytomegalovirus (CMV) infected cell antigen, CNT0888, CRTAM (CD355), CS-1 (also referred to as CD2 subset 1, CRACC, CD319, and 19A24), CTLA-4, Cyclin B 1, chromosome X open reading frame 61 (CXORF61), Cytochrome P450 1B 1 (CYP1B1), DNAM-1 (CD226), desmoglein 4, DR3, DR5, E-cadherin neoepitope, epidermal growth factor receptor (EGFR), EGF 1R, epidermal growth factor receptor variant III (EGFRvIII), epithelial glycoprotein-2 (EGP-2), epithelial glycoprotein-40 (EGP-40), EGF-like module-containing mucin-like hormone receptor-like 2 (EMR2), elongation factor 2 mutated (ELF2M), endosialin, Epithelial cell adhesion molecule (EPCAM), ephrin type-A receptor 2 (EphA2), Ephrin B2, receptor tyrosine-protein kinases erb-B2,3,4 (erb-B2,3,4), ERBB, ERBB2 (Her2/neu), ERG (transmembrane protease, serine 2 (TMPRSS2) ETS fusion gene), ETA, ETS translocation-variant gene 6, located on chromosome 12p (ETV6-AML), Fc fragment of IgA receptor (FCAR or CD89), fibroblast activation protein alpha (FAP), FBP, Fc receptor-like 5 (FCRL5), fetal acetylcholine receptor (AChR), fibronectin extra domain-B, Fms-Like Tyrosine Kinase 3 (FLT3), folate-binding protein (FBP), folate receptor 1, folate receptor a, Folate receptor (3, Fos-related antigen 1, Fucosyl, Fucosyl GM1; GM2, ganglioside G2 (GD2), ganglioside GD3 (aNeu5Ac(2-8)aNeu5Ac(2-3)bD-Galp(1-4)bDG1cp(1-1)Cer), o-acetyl-GD2 ganglioside (OAcGD2), GITR (TNFRSF 18), GM1, ganglioside GM3 (aNeu5Ac(2-3)bDGalp(1-4)bDG1cp(1-1)Cer), GP 100, hexasaccharide portion of globoH glycoceramide (GloboH), glycoprotein 75, Glypican-3 (GPC3), glycoprotein 100 (gplOO), GPNMB, G protein-coupled receptor 20 (GPR20), G protein-coupled receptor class C group 5, member D (GPRC5D), Hepatitis A virus cellular receptor 1 (HAVCR1), human Epidermal Growth Factor Receptor 2 (HER-2), HER2/neu, HER3, HER4, HGF, high molecular weight-melanoma-associated antigen (HMWMAA), human papilloma virus E6 (HPV E6), human papillomavirus E7 (HPV E7), heat shock protein 70-2 mutated (mut hsp70-2), human scatter factor receptor kinase, human Telomerase reverse transcriptase (hTERT), HVEM, ICOS, insulin-like growth factor receptor 1 (IGF-1 receptor), IGF-I, IgG1, immunoglobulin lambda-like polypeptide 1 (IGLL1), IL-6, Interleukin 11 receptor alpha (IL-11Ra), IL-13, Interleukin-13 receptor subunit alpha-2 (IL-13Ra2 or CD213A2), insulin-like growth factor I receptor (IGF1-R), integrin α5β1, integrin αvβ3, intestinal carboxyl esterase, κ-light chain, KCS1, kinase insert domain receptor (KDR), KIR, KIR2DL1, KIR2DL2, KIR2DL3, KIR3DL2, KIR-L, KG2D ligands, KIT (CD117), KLRGI, LAGE-1a, LAG3, lymphocyte-specific protein tyrosine kinase (LCK), Leukocyte immunoglobulin-like receptor subfamily A member 2 (LILRA2), legumain, Leukocyte-associated immunoglobulin-like receptor 1 (LAIRD, Lewis(Y) antigen, LeY, LG, LI cell adhesion molecule (LI-CAM), LIGHT, LMP2, lymphocyte antigen 6 complex, LTBR, locus K 9 (LY6K), Ly-6, lymphocyte antigen 75 (LY75), melanoma cancer testis antigen-1 (MAD-CT-1); melanoma cancer testis antigen-2 (MAD-CT-2), MAGE, Melanoma-associated antigen 1 (MAGE-A1), MAGE-A3 melanoma antigen recognized by T cells 1 (MelanA or MARTI), MelanA/MART1, Mesothelin, MAGE A3, melanoma inhibitor of apoptosis (ML-IAP), melanoma-specific chondroitin-sulfate proteoglycan (MCSCP), MORAb-009, MS4A1, Mucin 1 (MUC1), MUC2, MUC3, MUC4, MUC5AC, MUC5b, MUC7, MUC16, mucin CanAg, Mullerian inhibitory substance (MIS) receptor type II, v-myc avian myelocytomatosis viral oncogene neuroblastoma derived homolog (MYCN), N-glycolylneuraminic acid, N-Acetyl glucosaminyl-transferase V (NA17), neural cell adhesion molecule (NCAM), NKG2A, NKG2C, NKG2D, NKG2E ligands, NKR-P IA, NPC-1C, NTB-A, mammary gland differentiation antigen (NY-BR-1), NY-ESO-1, oncofetal antigen (h5T4), Olfactory receptor 51E2 (OR51E2), OX40, plasma cell antigen, poly SA, proacrosin binding protein sp32 (OY-TES 1), p53, p53 mutant, pannexin 3 (PANX3), prostatic acid phosphatase (PAP), paired box protein Pax-3 (PAX3), Paired box protein Pax-5 (PAX5), prostate carcinoma tumor antigen-1 (PCTA-1 or Galectin 8), PD-1H, Platelet-derived growth factor receptor alpha (PDGFR-alpha), PDGFR-beta, PDL192, PEN-5, phosphatidylserine, placenta-specific 1 (PLAC1), Polysialic acid, Prostase, prostatic carcinoma cells, prostein, Protease Serine 21 (Testisin or PRSS21), Proteinase3 (PR1), prostate stem cell antigen (PSCA), prostate-specific membrane antigen (PSMA), Proteasome (Prosome, Macropain) Subunit, Beta Type, Receptor for Advanced Glycation Endproducts (RAGE-1), RANKL, Ras mutant, Ras Homolog Family Member C (RhoC), RON, Receptor tyrosine kinase-like orphan receptor 1 (ROR1), renal ubiquitous 1 (RU1), renal ubiquitous 2 (RU2), sarcoma translocation breakpoints, Squamous Cell Carcinoma Antigen Recognized By T Cells 3 (SART3), SAS, SDC1, SLAMF7, sialyl Lewis adhesion molecule (sLe), Siglec-3, Siglec-7, Siglec-9, sonic hedgehog (SHH), sperm protein 17 (SPA17), Stage-specific embryonic antigen-4 (SSEA-4), STEAP, sTn antigen, synovial sarcoma, X breakpoint 2 (SSX2), Survivin, Tumor-associated glycoprotein 72 (TAG72), TCR5y, TCRa, TCRB, TCR Gamma Alternate Reading Frame Protein (TARP), telomerase, TIGIT TNF-α precursor, tumor endothelial marker 1 (TEM1/CD248), tumor endothelial marker 7-related (TEM7R), tenascin C, TGF beta 2, TGF-β, transglutaminase 5 (TGS5), angiopoietin-binding cell surface receptor 2 (Tie 2), TIM1, TIM2, TIM3, Tn Ag, TRAIL-R1, TRAIL-R2, Tyrosinase-related protein 2 (TRP-2), thyroid stimulating hormone receptor (TSHR), tumor antigen CTAA16.88, Tyrosinase, ROR1, TAG-72, uroplakin 2 (UPK2), VEGF-A, VEGFR-1, vascular endothelial growth factor receptor 2 (VEGFR2), and vimentin, Wilms tumor protein (WT1), or X Antigen Family, Member 1A (XAGE1) with a $K_d$ of about $1\times10^{-10}$ M to about $5\times10^{10}$ M.

In certain embodiments, provided herein is an antibody or an antigen binding molecule thereof that binds to the target human antigen, e.g., 2B4 (CD244), 4-1BB, 5T4, A33 antigen, adenocarcinoma antigen, adrenoceptor beta 3 (ADRB3), A kinase anchor protein 4 (AKAP-4), alpha-fetoprotein (AFP), anaplastic lymphoma kinase (ALK), Androgen receptor, B7H3 (CD276), β2-integrins, BAFF, B-lymphoma cell, B cell maturation antigen (BCMA), bcr-abl (oncogene fusion protein consisting of breakpoint cluster region (BCR) and Abelson murine leukemia viral oncogene homolog 1 (Abl), BhCG, bone marrow stromal cell antigen 2 (BST2), CCCTC-Binding Factor (Zinc Finger Protein)-Like (BORIS or Brother of the Regulator of Imprinted Sites), BST2, C242 antigen, 9-0-acetyl-CA19-9 marker, CA-125, CAEX, calreticulin, carbonic anhydrase 9 (CAIX), C-MET, CCR4, CCR5, CCR8, CD2, CD3, CD4, CD5, CD8, CD7, CD10, CD16, CD19, CD20, CD22, CD23 (IgE receptor), CD24, CD25, CD27, CD28, CD30 (TNFRSF8), CD33, CD34, CD38, CD40, CD40L, CD41, CD44, CD44V6, CD49f, CD51, CD52, CD56, CD63, CD70, CD72, CD74, CD79a, CD79b, CD80, CD84, CD96, CD97, CD100, CD123, CD125, CD133, CD137, CD138, CD150, CD152 (CTLA-4), CD160, CD171, CD179a, CD200, CD221, CD229, CD244, CD272 (BTLA), CD274 (PDL-1, B7H1), CD279 (PD-1), CD352, CD358, CD300 molecule-like family member f (CD300LF), Carcinoembryonic antigen (CEA), claudin 6 (CLDN6), C-type lectin-like molecule-1 (CLL-1 or CLECL1), C-type lectin domain family 12 member A (CLEC12A), a cytomegalovirus (CMV) infected cell antigen, CNT0888, CRTAM (CD355), CS-1 (also referred to as CD2 subset 1, CRACC, CD319, and 19A24), CTLA-4, Cyclin B 1, chromosome X open reading frame 61 (CX-ORF61), Cytochrome P450 1B 1 (CYP1B1), DNAM-1 (CD226), desmoglein 4, DR3, DR5, E-cadherin neoepitope, epidermal growth factor receptor (EGFR), EGF1R, epidermal growth factor receptor variant III (EGFRvIII), epithelial glycoprotein-2 (EGP-2), epithelial glycoprotein-40 (EGP-40), EGF-like module-containing mucin-like hormone receptor-like 2 (EMR2), elongation factor 2 mutated (ELF2M), endosialin, Epithelial cell adhesion molecule (EPCAM), ephrin type-A receptor 2 (EphA2), Ephrin B2, receptor tyrosine-protein kinases erb-B2,3,4 (erb-B2,3,4), ERBB, ERBB2 (Her2/neu), ERG (transmembrane protease, serine 2 (TMPRSS2) ETS fusion gene), ETA, ETS translocation-variant gene 6, located on chromosome 12p (ETV6-AML), Fc fragment of IgA receptor (FCAR or CD89), fibroblast activation protein alpha (FAP), FBP, Fc receptor-like 5 (FCRL5), fetal acetylcholine receptor (AChR), fibronectin extra domain-B, Fms-Like Tyrosine Kinase 3 (FLT3), folate-binding protein (FBP), folate receptor 1, folate receptor a, Folate receptor (3, Fos-related antigen 1, Fucosyl, Fucosyl GM1; GM2, ganglioside G2 (GD2), ganglioside GD3 (aNeu5Ac(2-8)aNeu5Ac(2-3)bDGalp(1-4) bDG1cp(1-1)Cer), o-acetyl-GD2 ganglioside (OAcGD2), GITR (TNFRSF 18), GM1, ganglioside GM3 (aNeu5Ac(2-3)bDGalp(1-4)bDG1cp(1-1)Cer), GP 100, hexasaccharide portion of globoH glycoceramide (GloboH), glycoprotein 75, Glypican-3 (GPC3), glycoprotein 100 (gplOO), GPNMB, G protein-coupled receptor 20 (GPR20), G protein-coupled receptor class C group 5, member D (GPRC5D), Hepatitis A virus cellular receptor 1 (HAVCR1), human Epidermal Growth Factor Receptor 2 (HER-2), HER2/neu, HER3, HER4, HGF, high molecular weight-melanoma-associated antigen (HMWMAA), human papilloma virus E6 (HPV E6), human papilloma virus E7 (HPV E7), heat shock protein 70-2 mutated (mut hsp70-2), human scatter factor receptor kinase, human Telomerase reverse transcriptase (hTERT), HVEM, ICOS, insulin-like growth factor receptor 1 (IGF-1 receptor), IGF-I, IgG1, immunoglobulin lambda-like polypeptide 1 (IGLL1), IL-6, Interleukin 11 receptor alpha (IL-11Ra), IL-13, Interleukin-13 receptor subunit alpha-2 (IL-13Ra2 or CD213A2), insulin-like growth factor I receptor (IGF1-R), integrin α5β1, integrin αvβ3, intestinal carboxyl esterase, κ-light chain, KCS1, kinase insert domain receptor (KDR), KIR, KIR2DL1, KIR2DL2, KIR2DL3, KIR3DL2, KIR-L, KG2D ligands, KIT (CD117), KLRGI, LAGE-1a, LAG3, lymphocyte-specific protein tyrosine kinase (LCK), Leukocyte immunoglobulin-like receptor subfamily A member 2 (LILRA2), legumain, Leukocyte-associated immunoglobulin-like receptor 1 (LAIR1), Lewis(Y) antigen, LeY, LG, LI cell adhesion molecule (LI-CAM), LIGHT, LMP2, lymphocyte antigen 6 complex, LTBR, locus K 9 (LY6K), Ly-6, lymphocyte antigen 75 (LY75), melanoma cancer testis antigen-1 (MAD-CT-1); melanoma cancer testis antigen-2 (MAD-CT-2), MAGE, Melanoma-associated antigen 1 (MAGE-A1), MAGE-A3 melanoma antigen recognized by T cells 1 (MelanA or MARTI), MelanA/MART1, Mesothelin, MAGE A3, melanoma inhibitor of apoptosis (ML-IAP), melanoma-specific chondroitin-sulfate proteoglycan (MCSCP), MORAb-009, MS4A1, Mucin 1 (MUC1), MUC2, MUC3, MUC4, MUC5AC, MUC5b, MUC7, MUC16, mucin CanAg, Mullerian inhibitory substance (MIS) receptor type II, v-myc avian myelocytomatosis viral oncogene neuroblastoma derived homolog (MYCN), N-glycolylneuraminic acid, N-Acetyl glucosaminyl-transferase V (NA17), neural cell adhesion molecule (NCAM), NKG2A, NKG2C, NKG2D, NKG2E ligands, NKR-P IA, NPC-1C, NTB-A, mammary gland differentiation antigen (NY-BR-1), NY-ESO-1, oncofetal antigen (h5T4), Olfactory receptor 51E2 (OR51E2), OX40, plasma cell antigen, poly SA, proacrosin binding protein sp32 (OY-TES 1), p53, p53 mutant, pannexin 3 (PANX3), prostatic acid phosphatase (PAP), paired box protein Pax-3 (PAX3), Paired box protein Pax-5 (PAX5), prostate carcinoma tumor antigen-1 (PCTA-1 or Galectin 8), PD-1H, Platelet-derived growth factor receptor alpha (PDGFR-alpha), PDGFR-beta, PDL192, PEN-5, phosphatidylserine, placenta-specific 1 (PLAC1), Polysialic acid, Prostase, prostate prostatic carcinoma cells, prostein, Protease Serine 21 (Testisin or PRSS21), Proteinase3 (PR1), prostate stem cell antigen (PSCA), prostate-specific membrane antigen (PSMA), Proteasome (Prosome, Macropain) Subunit, Beta Type, Receptor for Advanced Glycation Endproducts (RAGE-1), RANKL, Ras mutant, Ras Homolog Family Member C (RhoC), RON, Receptor tyrosine kinase-like orphan receptor 1 (ROR1), renal ubiquitous 1 (RU1), renal ubiquitous 2 (RU2), sarcoma translocation breakpoints, Squamous Cell Carcinoma Antigen Recognized By T Cells 3 (SART3), SAS, SDC1, SLAMF7, sialyl Lewis adhesion molecule (sLe), Siglec-3, Siglec-7, Siglec-9, sonic hedgehog (SHH), sperm protein 17 (SPA17), Stage-specific embryonic antigen-4 (SSEA-4), STEAP, sTn antigen, synovial sarcoma, X breakpoint 2 (SSX2), Survivin, Tumor-associated glycoprotein 72 (TAG72), TCR5y, TCRa, TCRB, TCR Gamma Alternate Reading Frame Protein (TARP), telomerase, TIGIT TNF-α precursor, tumor endothelial marker 1 (TEM1/CD248), tumor endothelial marker 7-related (TEM7R), tenascin C, TGF beta 2, TGF-β, transglutaminase 5 (TGS5), angiopoietin-binding cell surface receptor 2 (Tie 2), TIM1, TIM2, TIM3, Tn Ag, TRAIL-R1, TRAIL-R2, Tyrosinase-related protein 2 (TRP-2), thyroid stimulating hormone receptor (TSHR), tumor antigen CTAA16.88, Tyrosinase, ROR1, TAG-72, uroplakin 2 (UPK2), VEGF-A, VEGFR-1, vascular endothelial growth factor receptor 2 (VEGFR2), and vimentin, Wilms tumor protein (WT1), or X Antigen Family, Member 1A (XAGE1), with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

"Blimp-1" PR domain zinc finger protein 1 also known as BLIMP-1 is a protein encoded by the PRDM1 gene. BLIMP-1 acts as a repressor of beta-interferon (β-IFN) gene expression. The protein binds specifically to the PRDI (positive regulatory domain I element) of the β-IFN gene promoter. Blimp-1 is considered a 'master regulator' of hematopoietic stem cells. Details of Blimp-1 including nucleic acid and amino acid sequences can be found on the NCBI website; Gene ID: 639, updated on 22 Jul. 2020, which is specifically incorporated herein by reference.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present disclosure include, but are not limited to, cancers of the immune system including lymphoma, leukemia, myeloma, and other leukocyte malignancies. In some embodiments, the methods of the present disclosure can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time. Cancer further includes relapsed or refractory large B-cell lymphoma after two or more lines of systemic therapy, including diffuse large B-cell lymphoma (DLBCL) not otherwise specified, primary mediastinal large B-cell lymphoma after two or more lines of systemic therapy, high grade B-cell lymphoma, and DLBCL arising from follicular lymphoma.

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

"Chimeric antigen receptor" or "CAR" refers to a molecule engineered to comprise a binding motif and a means of activating immune cells (for example T cells such as naive T cells, central memory T cells, effector memory T cells or combination thereof) upon antigen binding. CARs are also known as artificial T cell receptors, chimeric T cell receptors or chimeric immunoreceptors. In some embodiments, a CAR comprises a binding motif, an extracellular domain, a transmembrane domain, one or more co-stimulatory domains, and an intracellular signaling domain. A T cell that has been genetically engineered to express a chimeric antigen receptor may be referred to as a CAR T cell. "Extracellular domain" (or "ECD") refers to a portion of a polypeptide that, when the polypeptide is present in a cell membrane, is understood to reside outside of the cell membrane, in the extracellular space.

The term "extracellular ligand-binding domain," as used herein, refers to an oligo- or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells.

The binding domain of the CAR may be followed by a "spacer," or, "hinge," which refers to the region that moves the antigen binding domain away from the effector cell surface to enable proper cell/cell contact, antigen binding and activation (Patel et al., Gene Therapy, 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered.

The "transmembrane" region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In certain embodiments, the transmembrane domain is synthetic in which case it would comprise predominantly hydrophobic residues such as leucine and valine.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular use in the disclosure include those derived from TCRzeta, FeRgamma, FcRbeta, CD3gamma, CD3delta, CD3epsilon, CD5, CD22, CD79a, CD79b and CD66d.

As used herein, the term, "costimulatory signaling domain," or "costimulatory domain", refers to the portion of the CAR comprising the intracellular domain of a costimulatory, molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1 BB (CD137), 0X40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD3zeta and 4-1 BB, other costimulatory domains are contemplated for use with the CARs described herein. The inclusion of one or more co stimulatory signaling domains may enhance the efficacy and expansion of T cells expressing CAR receptors. The intracellular signaling and costimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain derived from CD3zeta or FcRgamma together with one or more costimulatory signaling domains (e.g., intracellular costimulatory domains derived from CD28, CD137, CD134 and CD278) may more effectively direct antitumor activity as well as increased cytokine secretion, lytic activity, survival and proliferation in CAR expressing T cells in vitro, and in animal models and cancer patients (Milone et al., Molecular Therapy, 2009; 17: 1453-1464; Zhong et al., Molecular Therapy, 2010; 18: 413-420; Carpenito et al., PNAS, 2009; 106:3360-3365).

A "costimulatory signal" refers to a signal, which in combination with a primary signal, such as TCR/CD3 ligation, leads to a T cell response, such as, but not limited to, proliferation and/or upregulation or down regulation of key molecules.

A "costimulatory ligand" includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MEW class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MEW class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

A "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be "substantially similar" if they contain a conservative amino acid substitution in corresponding positions. For example, certain amino acids are generally classified as "hydrophobic" or "hydrophilic" amino acids, and/or as having "polar" or "non-polar" side chains. Substitution of one amino acid for another of the same type may be considered a conservative substitution. Exemplary amino acid categorizations are summarized in Tables 1 and 3 below:

TABLE 2

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 3

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

"Combination therapy" refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

"Corresponding to" may be used to designate the position/identity of a structural element in a molecule or composition through comparison with an appropriate reference molecule or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, for purposes of simplicity, residues in a polypeptide may be designated using a canonical numbering system based on a reference related polypeptide, so that an amino acid "corresponding to" a residue at position 100, for example, need not actually be the 100th amino acid in an amino acid chain provided it corresponds to the residue found at position 100 in the reference polypeptide. Various sequence alignment strategies are available, comprising software programs such as, for example, BLAST, CS-BLAST, CUDASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that may be utilized, for example, to identify "corresponding" residues in polypeptides and/or nucleic acids in accordance with the present disclosure.

An antigen binding molecule, such as an antibody, an antigen binding fragment thereof, CAR or TCR, "cross-competes" with a reference binding molecule, such as an antibody or an antigen binding fragment thereof, if the interaction between an antigen and the first antigen binding molecule blocks, limits, inhibits, or otherwise reduces the ability of the reference binding molecule to interact with the antigen. Cross competition can be complete, e.g., binding of the antigen binding molecule to the antigen completely blocks the ability of the reference binding molecule to bind the antigen, or it can be partial, e.g., binding of the antigen binding molecule to the antigen reduces the ability of the reference antigen binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137: 3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

A "cytokine," refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g., the FokI domain), while in other embodiments, the DNA binding molecule is a guide RNA component of an RNA-guided nuclease (e.g., Cas9 or Cfp1).

A "RNA binding molecule" is a molecule that can bind to RNA. Such RNA binding molecule can be a polypeptide, a domain of a protein, a domain within a larger protein or a polynucleotide. In some embodiments, the polynucleotide is DNA, while in other embodiments, the polynucleotide is RNA. In some embodiments, the RNA binding molecule is a small interfering RNA, such as a siRNA or miRNA, for example an siRNA or miRNA specific for Bach2, TCF7, Blimp-1, or A20.

The term "domain" refers to a portion of an entity. In some embodiments, a "domain" is associated with a structural and/or functional feature of the entity, e.g., so that, when the domain is physically separated from the rest of its parent entity, it substantially or entirely retains the structural and/or functional feature. In some embodiments, a domain may comprise a portion of an entity that, when separated from that (parent) entity and linked or connected with a different (recipient) entity, substantially retains and/or imparts on the recipient entity one or more structural and/or functional features, e.g., that characterized it in the parent entity. In some embodiments, a domain is a portion of a molecule (e.g., a small molecule, carbohydrate, lipid, nucleic acid, or polypeptide). In some embodiments, a domain is a section of a polypeptide; in some such embodiments, a domain is characterized by a structural element (e.g., an amino acid sequence or sequence motif, α-helix character, β-sheet character, coiled-coil character, random coil character, etc.), and/or by a functional feature (e.g., binding activity, enzymatic activity, folding activity, signaling activity, etc.).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from a naturally-occurring costimulatory domain, or a variant thereof, e.g., a variant having a truncated hinge domain ("THD"), and the activating domain can be derived from, e.g., CD3-zeta. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, which are incorporated by reference in their entirety. "Adoptive cell therapy" or "ACT" involves transfer of immune cells with anti-tumor activity into a subject, e.g., a cancer patient. In some embodiments, ACT is a treatment approach that involves the use of lymphocytes (e.g., engineered lymphocytes) with anti-tumor activity.

An "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham BC & Wells JA (1989) Science 244: 1081-1085 for a description of mutagenesis techniques, including alanine scanning mutagenesis techniques.

"Endogenous" with reference to a gene, protein, and/or nucleic acid refers to the natural presence of that gene, protein, and/or nucleic acid in a cell, such as an immune cell.

"Exogenous" refers to an introduced agent, such as a nucleic acid, gene, or protein, into a cell, for example from an outside source. A nucleic acid introduced into a cell is exogenous even if it encodes a protein which is naturally found in the cell. Such exogenous introduction of a nucleic acid encoding a protein can be used to increase the expression of the protein over the level that would naturally be found in the cell under similar conditions, e.g. without introduction of the exogenous nucleic acid.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of man. In embodiments, a CAR is a fusion protein.

The term "gene product" or "expression product" generally refers to an RNA transcribed from the gene (pre- and/or post-processing) or a polypeptide (pre- and/or post-modification) encoded by an RNA transcribed from the gene.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, or other mechanism, or previously present genetic material is altered or removed, for example by substitution or deletion mutation, or by other protocols). In some embodiments, a binding agent is a modified lymphocyte, e.g., a T cell, may be obtained from a patient or a donor. An engineered cell may be modified to express an exogenous construct, such as, e.g., a chimeric antigen receptor (CAR) or a T cell receptor (TCR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents.

A "T cell receptor" or "TCR" refers to antigen-recognition molecules present on the surface of T cells. During normal T cell development, each of the four TCR genes, α, β, γ, and δ, may rearrange leading to highly diverse TCR proteins.

The term "heterologous" means from any source other than naturally occurring sequences. For example, a heterologous sequence included as a part of a costimulatory protein is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions.

The terms "improve," "increase," "inhibit," and "reduce" indicate values that are relative to a baseline or other reference measurement. In some embodiments, an appropriate reference measurement may comprise a measurement in certain system (e.g., in a single individual) under otherwise comparable conditions absent presence of (e.g., prior to and/or after) an agent or treatment, or in presence of an appropriate comparable reference agent. In some embodiments, an appropriate reference measurement may comprise a measurement in comparable system known or expected to respond in a comparable way, in presence of the relevant agent or treatment.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "in vitro" refers to events occurring in an artificial environment, e.g., in a test tube, reaction vessel, cell culture, etc., rather than within a multi-cellular organism. The term "in vitro cell" refers to any cell which is cultured ex vivo. In particular, an in vitro cell can include a T cell. The term "in vivo" refers to events that occur within a multi-cellular organism, such as a human or a non-human animal.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Linker" (L) or "linker domain" or "linker region" refers to an oligo- or polypeptide region from about 1 to 100 amino acids in length, for example linking together any of the domains/regions of a CAR and or scFv. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL sequences of porcine teschovirus (P2A), virus (T2A) or combinations, variants and functional equivalents thereof. In other embodiments, the linker sequences may comprise Asp-Val/Ile-Glu-X-Asn-Pro-Gly$^{(2,4)}$-Pro$^{(2B)}$ motif (SEQ ID NO: 2), which results in cleavage between the 2A glycine and the 2B proline. Other linkers will be apparent to those of skill in the art and may be used in connection with this disclosure. A linker may be a portion of a multi-element agent that connects different elements to one another. For example, a polypeptide comprises two or more functional or structural domains may comprise a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. A linker may connect or link together any of the domains/regions of a CAR. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length (e.g., 1 to 10, 1 to 20, 1 to 30, 1 to 40, 1 to 50, 1 to 60, 1 to 70, 1 to 80, 1 to 90, 1 to 100, 10 to 20, 10 to 30, 10 to 40, 10 to 50, 10 to 60, 10 to 70, 10 to 80, 10 to 90, or 10 to 100 amino acids in length). In some embodiments, a linker is characterized in that it tends not to adopt a rigid three-dimensional structure, and instead provides flexibility to the polypeptide. In some examples, a linker may be used to connect or link different antigen binding systems such as two CARs of a bicistronic CAR. In another example it may be used to connect to or more polypeptides to be expressed, such as a CAR, TCF7 and/or Bach2. In some examples, CAR, TCF7 and/or Bach2 are connected by a cleavable linker. In another example, a linker may be used to connect or link different antigen binding domains, such as two scFv of a bispecific CARs.

The term "lymphocyte" includes natural killer (NK) cells, T cells, or B cells. NK cells are a type of cytotoxic (cell toxic) lymphocyte that represent a component of the inherent immune system. NK cells reject tumors and cells infected by viruses. It works through the process of apoptosis or programmed cell death. They were termed "natural killers" because they do not require activation in order to kill cells. T cells play a role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory $T_{SCM}$ cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element.

A "patient" includes any human who is afflicted with a cancer (e.g., a lymphoma or a leukemia). The terms "subject" and "patient" are used interchangeably herein.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

"Regulatory T cells" ("Treg", "Treg cells", or "Tregs") refer to a lineage of CD4+T lymphocytes that participate in controlling certain immune activities, e.g., autoimmunity, allergy, and response to infection. Regulatory T cells may regulate the activities of T cell populations, and may also influence certain innate immune system cell types. Tregs may be identified by the expression of the biomarkers CD4, CD25 and Foxp3, and low expression of CD127. Naturally occurring Treg cells normally constitute about 5-10% of the peripheral CD4+T lymphocytes. However, Treg cells within a tumor microenvironment (i.e. tumor-infiltrating Treg cells), Treg cells may make up as much as 20-30% of the total CD4+T lymphocyte population.

The term "sample" generally refers to an aliquot of material obtained or derived from a source of interest. In some embodiments, a source of interest is a biological or environmental source. In some embodiments, a source of interest may comprise a cell or an organism, such as a cell population, tissue, or animal (e.g., a human). In some embodiments, a source of interest comprises biological tissue or fluid. In some embodiments, a biological tissue or fluid may comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may comprise an intracellular fluid, an extracellular fluid, an intravascular fluid (blood plasma), an interstitial fluid, a lymphatic fluid, and/or a transcellular fluid. In some embodiments, a biological fluid may comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

"Single chain variable fragment", "single-chain antibody variable fragments" or "scFv" antibodies refer to forms of antibodies comprising the variable regions of only the heavy and light chains, connected by a linker peptide.

The term "stage of cancer" refers to a qualitative or quantitative assessment of the level of advancement of a cancer. In some embodiments, criteria used to determine the stage of a cancer may comprise, without limitation, one or more of where the cancer is located in a body, tumor size, whether the cancer has spread to lymph nodes, whether the cancer has spread to one or more different parts of the body, etc. In some embodiments, cancer may be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present without having spread to nearby tissue, also called carcinoma in situ, or CIS; CIS is not cancer, though could become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ; localized (cancer is limited to the place where it started, with no sign that it has spread); regional (cancer has spread to nearby lymph nodes, tissues, or organs): distant (cancer has spread to distant parts of the body); and unknown (there is not enough information to determine the stage).

"Stimulation," refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MEW Class I molecule loaded with a peptide, a superagonist anti-CD2 antibody, and a superagonist anti-CD28 antibody.

"TCF7" is a member of the T cell factor/lymphoid enhancer-binding factor family of high mobility group (HMG) box transcriptional activators. This gene is expressed predominantly in T cells and plays a role in natural killer cell and innate lymphoid cell development. The encoded protein forms a complex with beta-catenin and activates transcription through a Wnt/beta-catenin signaling pathway. Details of TCF7 including nucleic acid and amino acid sequences can be found on the NCBI website; Gene ID: 6932, updated on 22 Jul. 2020, which is specifically incorporated herein by reference.

The phrase "therapeutic agent" may refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms or human subjects. In some embodiments, an appropriate population may be defined by various criteria, such as a certain age group, gender, genetic background, preexisting clinical conditions, in accordance with presence or absence of a biomarker, etc. In some embodiments, a therapeutic agent is a substance that may be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it may be marketed for administration to humans. In some embodiments, a therapeutic agent is an agent for which a medical prescription is required for administration to humans.

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission. In some embodiments, treatment may be of a subject who does not exhibit signs of the relevant disease, disorder and/or condition and/or of a subject who exhibits only early signs of the disease, disorder, and/or condition. In some embodiments, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., Molecular Cloning: A Laboratory Manual (2d ed., Cold Spring Harbor Laboratory Press, Cold Spring Harbor, N.Y. (1989)), which is incorporated herein by reference.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. Thus, each zinc finger of a multi-finger ZFP includes a recognition helix region for binding to DNA within a backbone. The term zinc finger DNA binding protein is often abbreviated as zinc finger protein or ZFP. The term "zinc finger nuclease" includes one ZFN as well as a pair of ZFNs (the members of the pair are referred to as "left and right" or "first and second" or "pair") that dimerize to cleave the target gene.

A "TALE DNA binding domain" or "TALE" is a polypeptide comprising one or more TALE repeat domains/units. The repeat domains, each comprising a repeat variable diresidue (RVD), are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TALE proteins may be designed to bind to a target site using canonical or non-canonical RVDs within the repeat units. See, e.g., U.S. Pat. Nos. 8,586,526 and 9,458,205. Zinc finger and TALE DNA-binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the repeat variable diresidue or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs (canonical and non-canonical RVDs) and binding data. See, for example, U.S. Pat. Nos. 9,458,205; 8,586,526; 6,140,081; 6,453,242; and 6,534,261; see also International Patent Publication Nos. WO 98/53058; WO 98/53059; WO 98/53060; WO 02/016536; and WO 03/016496. The term "TALEN" includes one TALEN as well as a pair of TALENs (the members of the pair are referred to as "left and right" or "first and second" or "pair") that dimerize to cleave the target gene.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. "Modulation" or "modification" of gene expression refers to a change in the activity of a gene. Modulation of expression can include, but is not limited to, gene activation and gene repression, including by modification of the gene via binding of an exogenous molecule (e.g., a transcription factor). Modulation may also be achieved by modification of the gene sequence via genome editing (e.g., cleavage, alteration, inactivation, random mutation). Gene inactivation refers to any reduction in gene expression as compared to a cell that has not been modified as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

Less differentiated cells (for example, Naïve and CM) can proliferate robustly and have greater anti-tumor efficacy than more differentiated cells (EM/TEMRA) in vivo. To better understand the mechanism underlying the these differences at the gene expression level RNAseq was performed to examine genome-wide RNA expression of transcription factors highly expressed in sorted, unactivated and subsequently activated and CAR transduced T cell memory subsets. The data obtained showed that expression level of several genes was altered between the unactivated and subsequently activated and CAR transduced T cell memory subsets, including TCF7, Bach2, Blimp-1, and A20. In some examples the expression was increased in the naïve phenotype for both unactivated and subsequently activated and CAR transduced T cells. For example, the expression level of TCF7 and Bach2 was increased in both unactivated and subsequently activated and CD19 CAR transduced T cells. In some examples the expression was decreased in the naïve phenotype for both unactivated and subsequently activated and CAR transduced T cells. For example, the expression level of Blimp-1 and A20 was decreased in both unactivated and subsequently activated and CAR transduced T cells Blimp-1 and A20.

The present disclosure relates to methods of modulating the expression of transcription factors and other cellular proteins, for example decreasing expression of some genes, and increasing the expression of other genes, to increase and/or induce the cellular characteristics associated with naïve phenotype, proliferation, and/or functional properties in CAR-mediated killing and/or cytokine production, for example upon activation. In certain embodiments, the cellular characteristics associated with naïve phenotype include the surface expression, without limitation, one or more of, CD62L, CD127, CCR7, CD27, and CD45RA.

Some aspects of the disclosure relate increasing the expression of one or more of Bach2 and TCF7. The present disclosure also provides vectors (e.g., viral vectors) comprising nucleic acids for expressing Bach2 and TCF7 and compositions comprising such vectors. Some aspects of the disclosure relate to agents that inhibit the expression of one or more of Blimp-1. Some aspects of the disclosure relate to agents that inhibit the expression of one or more of Blimp-1 and A20. The present disclosure also relates to nucleic acids encoding such agents, for example agents that inhibit the expression of Blimp-1, and agents that inhibit the expression of A20. The present disclosure also provides vectors (e.g., viral vectors) comprising such nucleic acids and compositions comprising such vectors.

The present disclosure additionally provides engineered cells (e.g., T cells) comprising such polynucleotides and/or transduced with such viral vectors and compositions comprising such engineered cells, which in certain cases include one or more expressed CARs or engineered T cell receptors (TCRs). The present disclosure provides compositions (e.g., pharmaceutical compositions) including a plurality of engineered cells (e.g., engineered T cells). The present disclosure provides methods for manufacturing such engineered cells and compositions and uses (e.g., in treating a cancer) of such engineered cells and compositions. And, the present disclosure provides a method of inducing an immunity against a tumor comprising administering to a subject an effective amount of a cell comprising a polynucleotide, a vector, or a polypeptide of the present disclosure. Other aspects of the disclosure relate to cells in which the expression of Blimp-1, and A20, is reduced and/or inhibited and/or the expression Bach2 and TCF7 is increased, their use in a T cell therapy, such as CAR T cell therapy for the treatment of a patient suffering from a cancer. In certain embodiments the expression Bach2 and/or TCF7 is increased. Such an increase or over expression includes any detectable increase or over expression of Bach2 and/or TCF7. In certain examples, detectable Bach2 and/or TCF7 in a cell increase by at least 20%, at least 30%, at least 40%, at least 50%, at least 60%, at least 70%, at least 75%, at least 80%, at least 90%, at least 100%, at least 1.5 fold, at least 2.0 fold, at least 5 fold, at least 10 fold, at least 50 fold, at least 100 fold, at least 500 fold, or at least 1000 fold (such an amount of Bach2 and/or TCF7 detected in a corresponding cell in which the Bach2 and/or TCF7 has not been over expressed). In certain embodiments, the over expression of Bach2 and/or TCF7 induces a naïve T cell phenotype. In certain embodiments, the cellular characteristics associated with naïve phenotype include the surface expression, without limitation, one or more of, CD62L, CD127, CCR7, CD27, and CD45RA. In certain embodiments, the over expression of Bach2 and/or TCF7 promotes continued long-term CAR T cell expansion. In certain embodiments, the over expression of Bach2 increases CD62L and CD127 expression on cells after long-term expansion. In certain embodiments, the over expression of Bach2 and/or TCF7 increases peak CD8 T cell expansion. In certain embodiments, the reduced expression of Blimp-1 promotes continued long-term CAR expansion. In certain embodiments, the over expression Bach2 increases CD127 expression on cells after long-term expansion. In certain embodiments, the over expression of expression of Bach2 increases IL-2, IFNγ, and TNFα production.

Described are engineered cells, such as engineer T cells, where the expression of one or more of Blimp-1 and/or A20 has been reduced or eliminated. Such reduction or elimination includes any detectable decrease in the production of Blimp-1 and/or A20. In certain examples, detectable Blimp-1 and/or A20 in a cell decreases by at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such an amount of Blimp-1 and/or A20 detected in a corresponding cell in which the Blimp-1 and/or A20 has not been inhibited). In certain embodiments, the engineered cells further include a CAR and/or a TCR. In certain embodiments, the expression of one or more of Blimp-1, and A20 is reduced using a DNA-binding domains, for example coupled to a nuclease domain, that specifically binds to a target site in Blimp-1 gene or a A20 gene and mediates mutation at the target site thereby decreasing expression of functional Blimp-1, gene or A20 gene. Any DNA-binding domain can be used in the compositions and methods disclosed herein, including but not limited to a zinc finger DNA-binding domain, a TALE DNA binding domain, the DNA-binding portion (sgRNA) of a CRISPR/Cas nuclease, or a DNA-binding domain from a meganuclease. In certain embodiments, the reduced expression of Blimp-1 and/or A20 induces a naïve T cell phenotype. In certain embodiments, the cellular characteristics associated with naïve phenotype include the surface expression, without limitation, one or more of, CD62L, CD127, CCR7, CD27, and CD45RA. In certain embodiments, the reduced expression of Blimp-1 and/or A20 promotes continued long-term CAR T cell expansion. In certain embodiments, the reduced expression of Blimp-1 promotes continued long-term CAR expansion. In certain embodiments, the inhibition of Blimp-1 and/or A20 expression increases peak T cell expansion. In certain embodiments, the reduced expression of Blimp-1 and/or A20 expression increase the killing capacity during CAR-mediated killing.

Nucleic acid sequence of Blimp-1 can be any nucleic acid sequence known in the art, for example as available NCBI Gene database at Gene ID: 639, updated on 22 Jul. 2020, which is specifically incorporated herein by reference. In embodiments, the nucleotide sequence for Blimp-1 corresponds to NCBI Reference Sequence Nos. NM_001198, NM_182907, NM_001198.44, NM_182907.3, and NG_029115.

Nucleic acid sequence of A20 can be any nucleic acid sequence known in the art, for example as available NCBI Gene database at Gene ID: 7128, updated on 22 Jul. 2020, which is specifically incorporated herein by reference. In embodiments, the nucleotide sequence for A20 corresponds to NCBI Reference Sequence Nos. NM_001270507.1, NM_001270508.1, NM_006290.3, NG_032761.1, NM_001270507.2, NM_001270508.2, and NM_006290.4.

In certain embodiments, the DNA binding domain comprises a zinc finger protein.

Preferably, the zinc finger protein is non-naturally occurring in that it is engineered to bind to a target site of choice. See, for example, Beerli, et al. (2002) Nature Biotechnol. 20:135-141; Pabo, et al. (2001) Ann. Rev. Biochem. 70:313-340; Isalan, et al. (2001) Nature Biotechnol. 19:656-660; Segal, et al. (2001) Curr. Opin. Biotechnol. 12:632-637; Choo, et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; and 7,253,273; and U.S. Patent Publication Nos. 2005/0064474; 2007/0218528; and 2005/0267061. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in U.S. Pat. No. 6,794,136. Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

In some embodiments, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort, et al. (1997) Nucleic Acids Res. 25:3379-3388; Dujon, et al. (1989) Gene 82:115-118; Perler, et al. (1994) Nucleic Acids Res. 22, 1125-1127; Jasin (1996) Trends Genet. 12:224-228; Gimble, et al. (1996) J. Mol. Biol. 263:163-180; Argast, et al. (1998) J. Mol. Biol. 280: 345-353 and the New England Biolabs catalogue. In addition, the DNA-binding specificity of homing endonucleases and meganucleases can be engineered to bind non-natural target sites. See, for example, Chevalier, et al. (2002) Molec. Cell 10:895-905; Epinat, et al. (2003) Nucleic Acids Res. 31:2952-2962; Ashworth, et al. (2006) Nature 441:656-659; Pâques, et al. (2007) Current Gene Therapy 7:49-66; U.S. Patent Publication No. 2007/0117128.

In other embodiments, the DNA binding domain comprises an engineered domain from a TAL effector similar to those derived from the plant pathogens Xanthomonas (see Boch, et al. (2009) Science 326: 1509-1512 and Moscou and Bogdanove (2009) Science 326:1501) and Ralstonia (see Heuer, et al. (2007) Applied and Environmental Microbiology 73(13): 4379-4384); U.S. Patent Publication Nos. 2011/0301073 and 2011/0145940. The plant pathogenic bacteria of the genus Xanthomonas are known to cause many diseases in important crop plants. Pathogenicity of Xanthomonas depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay, et al. (2007) Science 318:648-651). These proteins contain a DNA binding domain and a transcriptional activation domain. One of the most well characterized TALEs is AvrBs3 from Xanthomonas campestgris pv. Vesicatoria (see Bonas, et al. (1989) Mol Gen Genet 218: 127-136 and International Patent Publication No. WO 2010/ 079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S., et al. (2006) J Plant Physiol 163(3): 256-272). In addition, in the phytopathogenic bacteria Ralstonia solanacearum two genes, designated brg11 and hpx17 have been found that are homologous to the AvrBs3 family of Xanthomonas in the R. solanacearum biovar 1 strain GMI1000 and in the biovar 4 strain RS1000 (See Heuer, et al. (2007) Appl and Envir Micro 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of Xanthomonas.

Specificity of these TAL effectors depends on the sequences found in the tandem repeats. The repeated sequence comprises approximately 102 base pairs and the repeats are typically 91-100% homologous with each other (Bonas, et al., ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove (2009) Science 326: 1501 and Boch, et al. (2009) Science 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch, et al., ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel, et al. (2013) Nucl Acid Res: 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley, et al. (2013) Nat Comm 4:1762 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In certain embodiments, the DNA-binding domain is part of a CRISPR/Cas nuclease system, including a single guide RNA (sgRNA) that binds to DNA. See, e.g., U.S. Pat. No. 8,697,359 and U.S. Patent Publication Nos. 2015/0056705 and 2015/0159172. The CRISPR (clustered regularly interspaced short palindromic repeats) locus, which encodes RNA components of the system, and the cas (CRISPR-associated) locus, which encodes proteins (Jansen, et al. (2002) Mol. Microbiol. 43:1565-1575; Makarova, et al. (2002) Nucleic Acids Res. 30:482-496; Makarova, et al. (2006) Biol. Direct 1:7; Haft, et al. (2005) PLoS Comput. Biol. 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs functional domain (e.g., nuclease such as Cas) to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran, et al. (2015) Nature 510:186).

Fusion molecules comprising DNA-binding domains (e.g., ZFPs or TALEs, CRISPR/Cas components such as single guide RNAs) as described herein associated with a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers. Such fusion molecules include transcription factors comprising the DNA-binding domains described herein and a transcriptional regulatory domain as well as nucleases comprising the DNA-binding domains and one or more nuclease domains.

Suitable domains for achieving activation (transcriptional activation domains) include the HSV VP16 activation domain (see, e.g., Hagmann, et al. (1997) J Virol. 71:5952-5962) nuclear hormone receptors (see, e.g., Torchia, et al. (1998) Curr. Opin. Cell. Biol. 10:373-383); the p65 subunit of nuclear factor kappa B (Bitko & Barik (1998) J. Virol. 72:5610-5618 and Doyle & Hunt (1997) Neuroreport 8:2937-2942); Liu, et al. (1998) Cancer Gene Ther. 5:3-28), or artificial chimeric functional domains such as VP64 (Beerli, et al. (1998) Proc. Natl. Acad. Sci. USA 95:14623-33), and degron (Molinari, et al. (1999) EMBO J. 18, 6439-6447). Additional exemplary activation domains include, Oct 1, Oct-2A, Sp1, AP-2, and CTF1 (Seipel, et al. (1992) EMBO J. 11, 4961-4968 as well as p300, CBP, PCAF, SRC1 PvALF, AtHD2A and ERF-2. See, for example, Robyr, et al. (2000) Mol. Endocrinol. 14:329-347; Collingwood, et al. (1999) J. Mol. Endocrinol. 23:255-275; Leo, et al. (2000) Gene 245:1-11; Manteuffel-Cymborowska (1999) Acta Biochim. Pol. 46:77-89; McKenna, et al. (1999) J. Steroid Biochem. Mol. Biol. 69:3-12; Malik, et al. (2000) Trends Biochem. Sci. 25:277-283; and Lemon, et al. (1999) Curr. Opin. Genet. Dev. 9:499-504. Additional exemplary activation domains include, but are not limited to, OsGAI, HALF-1, Cl, AP1, ARF-5, -6, -7, and -8, CPRF1, CPRF4, MYC-RP/GP, and TRAB 1. See, for example, Ogawa, et al. (2000) Gene 245:21-29; Okanami, et al. (1996) Genes Cells 1:87-99; Goff, et al. (1991) Genes Dev. 5:298-309; Cho, et al. (1999) Plant Mol. Biol. 40:419-429; Ulmason, et al. (1999) Proc. Natl. Acad. Sci. USA 96:5844-5849; Sprenger-Haussels, et al. (2000) Plant J. 22:1-8; Gong, et al. (1999) Plant Mol. Biol. 41:33-44; and Hobo, et al. (1999) Proc. Natl. Acad. Sci. USA 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in U.S. Pat. No. 7,053,264.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird, et al. (1999) Cell 99:451-454; Tyler, et al. (1999) Cell 99:443-446; Knoepfler, et al. (1999) Cell 99:447-450; and Robertson, et al. (2000) Nature Genet. 25:338-342. Additional exemplary repression domains include, but are not limited to, ROM2 and AtHD2A. See, for example, Chem, et al. (1996) Plant Cell 8:305-321; and Wu, et al. (2000) Plant J. 22:19-27.

Fusion molecules are constructed by methods of cloning and biochemical conjugation that are well known to those of skill in the art. Fusion molecules comprise a DNA-binding domain (e.g., ZFP, TALE, sgRNA) associated with a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp, et al. (2000) Proc. Natl. Acad. Sci. USA 97:3930-3935. Furthermore, single guide RNAs of the CRISPR/Cas system associate with functional domains to form active transcriptional regulators and nucleases.

In certain embodiments, the target site is present in an accessible region of cellular chromatin. Accessible regions can be determined as described, for example, in U.S. Pat. Nos. 7,217,509 and 7,923,542. If the target site is not present in an accessible region of cellular chromatin, one or more accessible regions can be generated as described in U.S. Pat. Nos. 7,785,792 and 8,071,370. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3) (Cordingley, et al. (1987) Cell 48:261-270; Pina, et al. (1990) Cell 60:719-731; and Cirillo, et al. (1998) EMBO J. 17:244-254).

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers. Additional exemplary functional domains are disclosed, for example, in U.S. Pat. Nos. 6,534,261 and 6,933,113.

Functional domains that are regulated by exogenous small molecules or ligands may also be selected. For example, RheoSwitch® technology may be employed wherein a functional domain only assumes its active conformation in the presence of the external RheoChem™ ligand (see for example U.S. Patent Publication No. 2009/0136465). Thus, the ZFP may be operably linked to the regulatable functional domain wherein the resultant activity of the ZFP-TF is controlled by the external ligand.

In certain embodiments, the fusion molecule comprises a DNA-binding binding domain associated with a cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames, et al. (2005) Nucleic Acids Res 33(20):e178; Arnould, et al. (2006)J. Mol. Biol. 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and/or TALEs can be fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel, et al. (2013) Nucl Acid Res: 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley, et al. (2013) Nat Comm: 1-8 DOI: 10.1038/ncomms2782). Any TALENs may be used in combination with additional TALENs (e.g., one or more TALENs (cTALENs or FokI-TALENs) with one or more mega-TALs) or other DNA cleavage enzymes.

In certain embodiments, the nuclease comprises a meganuclease (homing endonuclease) or a portion thereof that exhibits cleavage activity. Naturally-occurring meganucleases recognize 15-40 base-pair cleavage sites and are commonly grouped into four families: the LAGLIDADG family ("LAGLIDADG" disclosed as SEQ ID NO: 3), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort, et al. (1997) Nucleic Acids Res. 25:3379-3388; Dujon, et al. (1989) Gene 82:115-118; Perler, et al. (1994) Nucleic Acids Res. 22:1125-1127; Jasin (1996) Trends Genet. 12:224-228; Gimble, et al. (1996) J. Mol. Biol. 263:163-180; Argast, et al. (1998) J. Mol. Biol. 280:345-353 and the New England Biolabs catalogue.

DNA-binding domains from naturally-occurring meganucleases, have been used to promote site-specific genome modification in plants, yeast, Drosophila, mammalian cells and mice, but this approach has been limited to the modification of either homologous genes that conserve the meganuclease recognition sequence (Monet, et al. (1999), Biochem. Biophysics. Res. Common. 255: 88-93) or to pre-engineered genomes into which a recognition sequence has been introduced (Route, et al. (1994), Mol. Cell. Biol. 14:8096-106; Chilton, et al. (2003), Plant Physiology. 133: 956-65; Puchta, et al. (1996), Proc. Natl. Acad. Sci. USA 93:5055-60; Rong, et al. (2002), Genes Dev. 16:1568-81; Gouble, et al. (2006), J. Gene Med. 8(5):616-622). Accordingly, attempts have been made to engineer meganucleases to exhibit novel binding specificity at medically or biotechnologically relevant sites (Porteus, et al. (2005), Nat. Biotechnol. 23:967-73; Sussman, et al. (2004), J. Mol. Biol. 342:31-41; Epinat, et al. (2003) Nucleic Acids Res. 31:2952-62; Chevalier, et al. (2002) Molec. Cell 10:895-905; Epinat, et al. (2003) Nucleic Acids Res. 31:2952-2962; Ashworth, et al. (2006) Nature 441:656-659; Paques, et al. (2007) Current Gene Therapy 7:49-66; U.S. Patent Publication Nos. 2007/0117128; 2006/0206949; 2006/0153826; 2006/0078552; and 2004/0002092). In addition, naturally-occurring or engineered DNA-binding domains from meganucleases can be operably linked with a cleavage domain from a heterologous nuclease (e.g., FokI) and/or cleavage domains from meganucleases can be operably linked with a heterologous DNA-binding domain (e.g., ZFP or TALE).

In other embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain (e.g., from a restriction and/or meganuclease as described herein).

As described in detail above, zinc finger binding domains and TALE DNA binding domains can be engineered to bind to a sequence of choice. See, for example, Beerli, et al. (2002) Nature Biotechnol. 20:135-141; Pabo, et al. (2001) Ann. Rev. Biochem. 70:313-340; Isalan, et al. (2001) Nature Biotechnol. 19:656-660; Segal, et al. (2001) Curr. Opin. Biotechnol. 12:632-637; Choo, et al. (2000) Curr. Opin. Struct. Biol. 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet) nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, U.S. Pat. Nos. 6,453,242 and 6,534,261, incorporated by reference herein in their entireties.

Selection of target sites; and methods for design and construction of fusion proteins (and polynucleotides encoding same) are known to those of skill in the art and described in detail in U.S. Pat. Nos. 7,888,121 and 8,409,861, incorporated by reference in their entireties herein.

In addition, as disclosed in these and other references, zinc finger domains, TALEs and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Pat. No. 8,772,453.

Thus, nucleases such as ZFNs, TALENs and/or meganucleases can comprise any DNA-binding domain and any nuclease (cleavage) domain (cleavage domain, cleavage half-domain). As noted above, the cleavage domain may be heterologous to the DNA-binding domain, for example a zinc finger or TAL-effector DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort, et al. (1997) Nucleic Acids Res. 25:3379-3388. Additional enzymes which cleave DNA are known (e.g., 51 Nuclease; mung bean nuclease; pancreatic DNase I; micrococcal nuclease; yeast HO endonuclease; see also Linn, et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites, but may lie 1 or more kilobases away from the cleavage site, including between 1-50 base pairs (or any value therebetween including 1-5, 1-10, and 1-20 base pairs), 1-100 base pairs (or any value therebetween), 100-500 base pairs (or any value therebetween), 500 to 1000 base pairs (or any value therebetween) or even more than 1 kb from the cleavage site.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li, et al. (1992) Proc. Natl. Acad. Sci. USA 89:4275-4279; Li, et al. (1993) Proc. Natl. Acad. Sci. USA 90:2764-2768; Kim, et al. (1994a) Proc. Natl. Acad. Sci. USA 91:883-887; Kim, et al. (1994b)J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered. An exemplary Type IIS restriction enzyme, whose cleavage domain is separable from the binding domain, is FokI. This particular enzyme is active as a dimer. Bitinaite, et al. (1998) Proc. Natl. Acad. Sci. USA 95:10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure. A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts, et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598; and 8,623,618; and U.S. Patent Publication No. 2011/0201055, the disclosures of all of which are incorporated by reference in their entireties herein. "Sharkey" mutations (e.g., 418 and 441, numbered relative to full-length) and additional mutations, for example, to residue 416 (e.g., R416S) and/or residue 525 (e.g., K525S) as described in U.S. Patent Publication No. 2018/0087072, may also be included. Thus, the FokI cleavage domains used in the nucleases may be mutated at one or more of the following amino acid residues positions (numbered relative to full length): 416, 418, 441, 446, 447, 479, 483, 484, 486, 487, 490, 491, 496, 498, 499, 500, 525, 531, 534, 537, and/or 538.

In certain embodiments, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen, et al. (2002) Mol. Microbiol. 43:1565-1575; Makarova, et al. (2002) Nucleic Acids Res. 30:482-496; Makarova, et al. (2006) Biol. Direct 1:7; Haft, et al. (2005) PLoS Comput. Biol. 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Described herein are engineered cells, such as engineered T cells, where the expression of one or more of Bach2 and TCF7 has been increased. In certain embodiments, the engineered cells further include a CAR and/or a TCR. The full length amino acid sequence of TCF7 is shown below as SEQ ID NO: 4 (an exemplary nucleic acid sequence is shown below as SEQ ID NO: 5) In embodiments, In certain embodiments, the engineered cells are engineered to express a TCF7 polypeptide or fragment there comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID NO: 4.

```
                                                          (SEQ ID NO: 4)
MPQLDSGGGGAGGGDDLGAPDELLAFQDEGEEQDDKSRDSAAGPERDLAEL

KSSLVNESEGAAGGAGIPGVPGAGAGARGEAEALGREHAAQRLFPDKLPEPLEDGLKA

PECTSGMYKETVYSAFNLLMHYPPPSGAGQHPQPQPPLHKANQPPHGVPQLSLYEHENS

PHPTPAPADISQKQVHRPLQTPDLSGFYSLTSGSMGQLPHTVSWFTHPSLMLGSGVPGH

PAAIPHPAIVPPSGKQELQPFDRNLKTQAESKAEKEAKKPTIKKPLNAFMLYMKEMRAK

VIAECTLKESAAINQILGRRWHALSREEQAKYYELARKERQLHMQLYPGWSARDNYG

KKKRRSREKHQESTTGGKRNAFGTYPEKAAAPAPFLPMTVLRAKRS (SEQ ID NO: 5)
ATGCCTCAGCTGGATTCTGGCGGAGGCGGAGCTGGTGGCGGAGATGATCTT

GGAGCACCTGATGAGCTGCTGGCATTCCAGGACGAGGGCGAAGAACAGGACGACA

AGAGCAGAGATTCTGCCGCCGGACCTGAGAGAGATCTGGCCGAGCTGAAGTCCAGC

CTGGTCAATGAATCTGAAGGCGCCGCTGGCGGCGCTGGAATTCCTGGTGTTCCTGGC

GCTGGTGCTGGTGCAAGAGGCGAAGCTGAAGCCCTGGGAAGAGAACACGCTGCCC

AGAGACTGTTCCCCGACAAGCTGCCTGAGCCTCTGGAAGATGGACTGAAGGCCCCT

GAGTGTACCAGCGGCATGTACAAAGAAACCGTGTACAGCGCCTTCAACCTGCTGAT

GCACTACCCTCCACCTAGCGGAGCAGGACAGCATCCTCAACCTCAGCCTCCACTGC

ACAAGGCCAATCAGCCACCTCATGGCGTGCCACAGCTGAGCCTGTACGAGCACTTC

AACAGCCCTCATCCTACTCCAGCTCCAGCCGACATCAGCCAGAAACAGGTGCACAG

ACCTCTGCAGACCCCTGACCTGAGCGGCTTTTACAGCCTGACAAGCGGCAGCATGG

GACAGCTGCCTCATACCGTGTCCTGGTTCACACACCCCAGCCTGATGCTTGGAAGCG

GAGTGCCTGGACACCCTGCCGCTATTCCTCATCCTGCCATCGTGCCTCCAAGCGGCA

AGCAAGAGCTGCAGCCCTTCGACCGGAACCTGAAAACACAGGCCGAGAGCAAGGC

CGAGAAAGAGGCCAAGAAGCCCACCATCAAGAAGCCTCTGAACGCCTTCATGCTGT

ACATGAAAGAAATGCGGGCCAAAGTGATCGCCGAGTGCACCCTGAAAGAGTCCGC

CGCCATCAACCAGATCCTGGGCAGAAGATGGCACGCCCTGTCCAGAGAGGAACAG

GCCAAGTACTACGAGCTGGCCCGGAAAGAACGGCAGCTGCACATGCAACTGTACCC

TGGCTGGAGCGCCAGAGACAACTACGGCAAGAAGAAGCGGCGGAGCAGAGAGAAG

CACCAAGAGTCTACAACCGGCGGCAAGAGAAACGCCTTCGGCACATATCCCGAGAA

AGCCGCTGCTCCCGCTCCTTTCCTGCCTATGACTGTGCTGAGGGCCAAGAGAAGC

>TCF7_2A_LN (LNGFR for all sequences is truncated, - is stop codon)
                                                          (SEQ ID NO: 6)
MPQLDSGGGGAGGGDDLGAPDELLAFQDEGEEQDDKSRDSAAGPERDLAEL

KSSLVNESEGAAGGAGIPGVPGAGAGARGEAEALGREHAAQRLFPDKLPEPLEDGLKA

PECTSGMYKETVYSAFNLLMHYPPPSGAGQHPQPQPPLHKANQPPHGVPQLSLYEHENS
```

-continued

PHPTPAPADISQKQVHRPLQTPDLSGFYSLTSGSMGQLPHTVSWFTHPSLMLGSGVPGH

PAAIPHP AIVPPSGKQELQPFDRNLKTQAESKAEKEAKKPTIKKPLNAFMLYMKEMRAK

VIAECTLKESAAINQILGRRWHALSREEQAKYYELARKERQLHMQLYPGWSARDNYG

KKKRRSREKHQESTTGGKRNAFGTYPEKAAAPAPFLPMTVLRAKRSGSGEGRGSLLTC

GDVEENPGPMGAGATGRAMDGPRLLLLLLLGVSLGGAKEACPTGLYTHSGECCKACN

LGEGVAQPCGANQTVCEPCLDSVTFSDVVSATEPCKPCTECVGLQSMSAPCVEADDAV

CRCAYGYYQDETTGRCEACRVCEAGSGLVFSCQDKQNTVCEECPDGTYSDEANHVDP

CLPCTVCEDTERQLRECTRWADAECEEIPGRWITRSTPPEGSDSTAPSTQEPEAPPEQDLI

ASTVAGVVTTVMGSSQPVVTRGTTDNLIPVYCSILAAVVVGLVAYIAFKR

>TCF7_2A_LNGFR (LNGFR for all sequences is truncated)
(SEQ ID NO: 7)
ATGCCTCAGCTGGATTCTGGCGGAGGCGGAGCTGGTGGCGGAGATGATCTTGGAGC

ACCTGATGAGCTGCTGGCATTCCAGGACGAGGGCGAAGAACAGGACGACAAGAGC

AGAGATTCTGCCGCCGGACCTGAGAGAGATCTGGCCGAGCTGAAGTCCAGCCTGGT

CAATGAATCTGAAGGCGCCGCTGGCGGCGCTGGAATTCCTGGTGTTCCTGGCGCTG

GTGCTGGTGCAAGAGGCGAAGCTGAAGCCCTGGGAAGAGAACACGCTGCCCAGAG

ACTGTTCCCCGACAAGCTGCCTGAGCCTCTGGAAGATGGACTGAAGGCCCCTGAGT

GTACCAGCGGCATGTACAAAGAAACCGTGTACAGCGCCTTCAACCTGCTGATGCAC

TACCCTCCACCTAGCGGAGCAGGACAGCATCCTCAACCTCAGCCTCCACTGCACAA

GGCCAATCAGCCACCTCATGGCGTGCCACAGCTGAGCCTGTACGAGCACTTCAACA

GCCCTCATCCTACTCCAGCTCCAGCCGACATCAGCCAGAAACAGGTGCACAGACCT

CTGCAGACCCCTGACCTGAGCGGCTTTTACAGCCTGACAAGCGGCAGCATGGGACA

GCTGCCTCATACCGTGTCCTGGTTCACACACCCCAGCCTGATGCTTGGAAGCGGAGT

GCCTGGACACCCTGCCGCTATTCCTCATCCTGCCATCGTGCCTCCAAGCGGCAAGCA

AGAGCTGCAGCCCTTCGACCGGAACCTGAAAACACAGGCCGAGAGCAAGGCCGAG

AAAGAGGCCAAGAAGCCCACCATCAAGAAGCCTCTGAACGCCTTCATGCTGTACAT

GAAAGAAATGCGGGCCAAAGTGATCGCCGAGTGCACCCTGAAAGAGTCCGCCGCC

ATCAACCAGATCCTGGGCAGAAGATGGCACGCCCTGTCCAGAGAGGAACAGGCCA

AGTACTACGAGCTGGCCCGGAAAGAACGGCAGCTGCACATGCAACTGTACCCTGGC

TGGAGCGCCAGAGACAACTACGGCAAGAAGAAGCGGCGGAGCAGAGAGAAGCACC

AAGAGTCTACAACCGGCGGCAAGAGAAACGCCTTCGGCACATATCCCGAGAAAGC

CGCTGCTCCCGCTCCTTTCCTGCCTATGACTGTGCTGAGGGCCAAGAGAAGCGGAA

GTGGAGAGGGAAGAGGCTCCCTTCTGACATGCGGCGACGTGGAGGAGAACCCTGG

ACCTATGGGAGCTGGAGCTACCGGAAGAGCTATGGACGGACCAAGACTTCTCCTGC

TCCTCCTGCTGGGTGTGAGCCTGGGAGGAGCTAAGGAGGCTTGCCCTACCGGACTG

TACACCCACTCTGGCGAGTGCTGCAAGGCTTGCAACCTGGGAGAGGGAGTGGCTCA

ACCCTGCGGAGCTAACCAAACTGTCTGCGAGCCTTGCCTGGACTCTGTGACATTCTC

CGACGTGGTGTCTGCCACCGAGCCTTGCAAGCCTTGCACCGAATGCGTGGGCCTGC

AAAGCATGAGCGCTCCTTGCGTGGAGGCTGACGACGCTGTGTGCCGATGCGCTTAC

GGATACTACCAAGACGAGACCACCGGAAGATGCGAGGCTTGCCGAGTGTGCGAGG

CTGGAAGCGGACTCGTGTTCTCCTGCCAAGACAAGCAAAACACCGTGTGTGAGGAA

TGCCCTGACGGAACCTACTCCGACGAGGCTAACCACGTGGACCCTTGCCTGCCTTGC

```
ACCGTGTGTGAGGACACCGAGAGACAACTGAGGGAGTGCACAAGATGGGCTGACG

CTGAGTGTGAGGAGATCCCTGGAAGATGGATCACAAGATCTACCCCTCCTGAGGGA

AGCGACTCCACCGCTCCTTCCACCCAAGAGCCCGAGGCTCCTCCTGAGCAAGACCT

GATCGCAAGCACCGTGGCTGGAGTGGTTACAACCGTGATGGGAAGCTCCCAACCCG

TGGTTACAAGGGGAACCACCGACAACCTGATCCCTGTGTACTGCTCCATCCTGGCTG

CTGTGGTGGTGGGATTGGTGGCCTACATCGCTTTCAAGAGATGAATCGAT.
```

The full length amino acid sequence of Bach2 is shown below as SEQ ID NO: 8 (an exemplary nucleic acid sequence is shown below as SEQ ID NO: 9) In embodiments, In certain embodiments, the engineered cells are engineered to express a Bach2 polypeptide or fragment there comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID NO: 8.

```
                                                    (SEQ ID NO: 8)
MSVDEKPDSPMYVYESTVHCTNILLGLNDQRKKDILCDVTLIVERKEFRAHRA

VLAACSEYFWQALVGQTKNDLVVSLPEEVTARGFGPLLQFAYTAKLLLSRENIREVIRC

AEFLRMHNLEDSCFSFLQTQLLNSEDGLFVCRKDAACQRPHEDCENSAGEEEDEEEET

MDSETAKMACPRDQMLPEPISFEAAAIPVAEKEEALLPEPDVPTDTKESSEKDALTQYP

RYKKYQLACTKNVYNASSHSTSGFASTFREDNSSNSLKPGLARGQIKSEPPSEENEEESI

TLCLSGDEPDAKDRAGDVEMDRKQPSPAPTPTAPAGAACLERSRSVASPSCLRSLFSITK

SVELSGLPSTSQQHFARSPACPFDKGITQGDLKTDYTPFTGNYGQPHVGQKEVSNFTMG

SPLRGPGLEALCKQEGELDRRSVIFSSSACDQVSTSVHSYSGVSSLDKDLSEPVPKGLWV

GAGQSLPSSQAYSHGGLMADHLPGRMRPNTSCPVPIKVCPRSPPLETRTRTSSSCSSYSY

AEDGSGGSPCSLPLCEFSSSPCSQGARFLATEHQEPGLMGDGMYNQVRPQIKCEQSYGT

NSSDESGSFSEADSESCPVQDRGQEVKLPFPVDQITDLPRNDFQMMIKMHKLTSEQLEFI

HDVRRRSKNRIAAQRCRKRKLDCIQNLECEIRKLVCEKEKLLSERNQLKACMGELLDNF

SCLSQEVCRDIQSPEQIQALHRYCPVLRPMDLPTASSINPAPLGAEQNIAASQCAVGENV

PCCLEPGAAPPGPPWAPSNTSENCTSGRRLEGTDPGTFSERGPPLEPRSQTVTVDFCQEM

TDKCTTDEQPRKDYTRAKRS (SEQ ID NO: 9)
ATGAGCGTGGACGAGAAGCCTGACAGCCCTATGTACGTGTACGAGAGCAC

CGTGCACTGCACCAACATCCTGCTGGGCCTGAACGACCAGCGGAAGAAAGACATCC

TGTGCGACGTGACCCTGATCGTGGAACGGAAAGAGTTCAGAGCCCACAGAGCCGTG

CTGGCCGCCTGTAGCGAGTATTTTTGGCAGGCCCTCGTGGGCCAGACCAAGAACGA

TCTGGTGGTGTCCCTGCCTGAGGAAGTGACCGCCAGAGGATTTGGACCCCTGCTGC

AGTTTGCCTACACCGCCAAACTGCTGCTGAGCCGCGAGAACATCCGGGAAGTGATC

AGATGCGCCGAGTTCCTGCGGATGCACAACCTGGAAGATAGCTGCTTCAGCTTCCT

GCAGACCCAGCTGCTGAACAGCGAGGATGGCCTGTTCGTGTGCAGAAAGGATGCCG

CCTGTCAGAGGCCTCACGAGGACTGCGAAAATTCTGCCGGCGAGGAAGAGGACGA

AGAGGAAGAAACCATGGACAGCGAGACAGCCAAGATGGCTTGCCCCAGGGACCAG

ATGCTGCCTGAGCCTATCTCTTTCGAGGCCGCTGCCATTCCTGTGGCCGAGAAAGAA

GAAGCCCTGCTGCCAGAGCCAGACGTGCCCACCGATACAAAAGAGAGCAGCGAGA

AGGACGCCCTGACACAGTACCCCAGATACAAGAAGTACCAGCTGGCCTGCACCAAG

AATGTGTACAACGCCAGCAGCCACAGCACCAGCGGCTTTGCCTCTACCTTCAGAGA
```

-continued

```
GGACAACAGCAGCAACAGCCTGAAGCCTGGACTGGCCAGAGGCCAGATCAAGTCT

GAGCCTCCTAGCGAGGAAAATGAAGAGGAATCTATCACCCTGTGCCTGAGCGGCGA

CGAGCCTGATGCCAAAGATAGAGCTGGCGACGTGGAAATGGACCGGAAGCAGCCT

TCTCCAGCTCCTACACCTACAGCTCCAGCTGGCGCAGCCTGCCTGGAAAGATCAAG

ATCTGTGGCTAGCCCCAGCTGCCTGCGGAGCCTGTTTAGCATCACCAAGAGCGTGG

AACTGAGCGGCCTGCCTAGCACATCCCAGCAGCACTTTGCCAGATCTCCCGCCTGTC

CTTTCGACAAGGGAATCACCCAGGGCGACCTGAAAACCGACTACACCCCTTTCACC

GGCAACTACGGACAGCCTCACGTGGGACAGAAAGAGGTGTCCAACTTTACCATGGG

CAGCCCTCTGAGAGGCCCAGGACTTGAGGCCCTGTGTAAACAAGAGGGCGAGCTGG

ATCGGCGGAGCGTGATCTTTTCTAGCAGCGCCTGTGACCAGGTGTCCACCAGCGTGC

ACTCTTACAGCGGAGTGTCCAGCCTGGATAAGGACCTGTCTGAGCCCGTGCCTAAA

GGCCTGTGGGTTGGAGCTGGACAGAGCCTGCCAAGCAGCCAGGCTTATTCTCACGG

CGGACTGATGGCCGATCATCTGCCTGGTAGAATGCGGCCCAACACCAGCTGTCCCG

TGCCAATCAAAGTGTGCCCTAGAAGCCCTCCTCTGGAAACCCGGACCAGAACCAGC

AGCAGCTGTTCCAGCTACAGCTATGCCGAGGATGGAAGCGGCGGCAGCCCTTGTTC

ACTGCCTCTGTGCGAGTTTAGCAGCAGCCCCTGTTCTCAGGGCGCCAGATTTCTGGC

CACCGAGCATCAAGAACCTGGCCTGATGGGCGACGGCATGTACAATCAAGTGCGGC

CCCAGATTAAGTGCGAGCAGAGCTACGGCACCAACAGCTCTGATGAGAGCGGCAGC

TTTAGCGAGGCCGATAGCGAAAGCTGCCCCGTGCAGGATAGAGGCCAAGAAGTGA

AGCTGCCCTTTCCAGTGGATCAGATCACCGACCTGCCTCGGAACGACTTCCAGATGA

TGATCAAGATGCACAAGCTGACCTCCGAGCAGCTGGAATTCATCCACGACGTGCGG

CGGAGAAGCAAGAACAGAATCGCTGCCCAGCGGTGCCGGAAGAGAAAGCTGGACT

GCATCCAGAATCTGGAATGCGAGATCCGGAAGCTCGTGTGCGAAAAAGAGAAGCT

GCTGTCCGAGCGGAACCAGCTGAAGGCCTGTATGGGAGAGCTGCTGGACAACTTCA

GCTGTCTGTCTCAAGAAGTGTGCCGGGACATCCAGTCTCCAGAGCAGATTCAGGCC

CTGCACAGATACTGCCCTGTGCTGAGGCCTATGGATCTGCCTACAGCCAGCAGCATC

AACCCTGCTCCTCTGGGAGCCGAGCAGAATATTGCCGCCTCTCAGTGTGCCGTGGGC

GAGAATGTGCCTTGCTGTCTTGAACCTGGCGCCGCTCCTCCTGGACCTCCTTGGGCT

CCTTCTAACACCAGCGAGAACTGCACCTCCGGCAGAAGGCTGGAAGGCACAGATCC

TGGCACCTTCAGCGAAAGAGGCCCACCACTGGAACCCAGATCTCAGACCGTGACCG

TGGACTTCTGCCAAGAGATGACCGACAAGTGCACCACCGACGAGCAGCCCAGAAA

GGACTACACCAGGGCCAAGAGAAGC
```

>BACH2 2A LN
(SEQ ID NO: 10)

```
MSVDEKPDSPMYVYESTVHCTNILLGLNDQRKKDILCDVTLIVERKEFRAHRA

VLAACSEYFWQALVGQTKNDLVVSLPEEVTARGFGPLLQFAYTAKLLLSRENIREVIRC

AEFLRMHNLEDSCFSFLQTQLLNSEDGLFVCRKDAACQRPHEDCENSAGEEEDEEEET

MDSETAKMACPRDQMLPEPISFEAAAIPVAEKEEALLPEPDVPTDTKESSEKDALTQYP

RYKKYQLACTKNVYNASSHSTSGFASTFREDNSSNSLKPGLARGQIKSEPPSEENEEESI

TLCLSGDEPDAKDRAGDVEMDRKQPSPAPTPTAPAGAACLERSRSVASPSCLRSLFSITK

SVELSGLPSTSQQHFARSPACPFDKGITQGDLKTDYTPFTGNYGQPHVGQKEVSNFTMG
```

-continued

SPLRGPGLEALCKQEGELDRRSVIFSSSACDQVSTSVHSYSGVSSLDKDLSEPVPKGLWV

GAGQSLPSSQAYSHGGLMADHLPGRMRPNTSCPVPIKVCPRSPPLETRTRTSSSCSSYSY

AEDGSGGSPCSLPLCEFSSSPCSQGARFLATEHQEPGLMGDGMYNQVRPQIKCEQSYGT

NSSDESGSFSEADSESCPVQDRGQEVKLPFPVDQITDLPRNDFQMMIKMHKLTSEQLEFI

HDVRRRSKNRIAAQRCRKRKLDCIQNLECEIRKLVCEKEKLLSERNQLKACMGELLDNF

SCLSQEVCRDIQSPEQIQALHRYCPVLRPMDLPTASSINPAPLGAEQNIAASQCAVGENV

PCCLEPGAAPPGPPWAPSNTSENCTSGRRLEGTDPGTFSERGPPLEPRSQTVTVDFCQEM

TDKCTTDEQPRKDYTRAKRSGSGEGRGSLLTCGDVEENPGPMGAGATGRAMDGPRLL

LLLLLGVSLGGAKEACPTGLYTHSGECCKACNLGEGVAQPCGANQTVCEPCLDSVTFS

DVVSATEPCKPCTECVGLQSMSAPCVEADDAVCRCAYGYYQDETTGRCEACRVCEAG

SGLVFSCQDKQNTVCEECPDGTYSDEANHVDPCLPCTVCEDTERQLRECTRWADAECE

EIPGRWITRSTPPEGSDSTAPSTQEPEAPPEQDLIASTVAGVVTTVMGSSQPVVTRGTTD

NLIPVYCSILAAVVVGLVAYIAFKR

Bach2_2A_LNGFR (LNGFR for all sequences is truncated)
(SEQ ID NO: 11)
ATGAGCGTGGACGAGAAGCCTGACAGCCCTATGTACGTGTACAGAGAGCAC

CGTGCACTGCACCAACATCCTGCTGGGCCTGAACGACCAGCGGAAGAAAGACATCC

TGTGCGACGTGACCCTGATCGTGGAACGGAAAGAGTTCAGAGCCCACAGAGCCGTG

CTGGCCGCCTGTAGCGAGTATTTTTGGCAGGCCCTCGTGGGCCAGACCAAGAACGA

TCTGGTGGTGTCCCTGCCTGAGGAAGTGACCGCCAGAGGATTTGGACCCCTGCTGC

AGTTTGCCTACACCGCCAAACTGCTGCTGAGCCGCGAGAACATCCGGGAAGTGATC

AGATGCGCCGAGTTCCTGCGGATGCACAACCTGGAAGATAGCTGCTTCAGCTTCCT

GCAGACCCAGCTGCTGAACAGCGAGGATGGCCTGTTCGTGTGCAGAAAGGATGCCG

CCTGTCAGAGGCCTCACGAGGACTGCGAAAATTCTGCCGGCGAGGAAGAGGACGA

AGAGGAAGAAACCATGGACAGCGAGACAGCCAAGATGGCTTGCCCCAGGGACCAG

ATGCTGCCTGAGCCTATCTCTTTCGAGGCCGCTGCCATTCCTGTGGCCGAGAAAGAA

GAAGCCCTGCTGCCAGAGCCAGACGTGCCCACCGATACAAAAGAGAGCAGCGAGA

AGGACGCCCTGACACAGTACCCCAGATACAAGAAGTACCAGCTGGCCTGCACCAAG

AATGTGTACAACGCCAGCAGCCACAGCACCAGCGGCTTTGCCTCTACCTTCAGAGA

GGACAACAGCAGCAACAGCCTGAAGCCTGGACTGGCCAGAGGCCAGATCAAGTCT

GAGCCTCCTAGCGAGGAAAATGAAGAGGAATCTATCACCCTGTGCCTGAGCGGCGA

CGAGCCTGATGCCAAAGATAGAGCTGGCGACGTGGAAATGGACCGGAAGCAGCCT

TCTCCAGCTCCTACACCTACAGCTCCAGCTGGCGCAGCCTGCCTGGAAAGATCAAG

ATCTGTGGCTAGCCCCAGCTGCCTGCGGAGCCTGTTTAGCATCACCAAGAGCGTGG

AACTGAGCGGCCTGCCTAGCACATCCCAGCAGCACTTTGCCAGATCTCCCGCCTGTC

CTTTCGACAAGGGAATCACCCAGGGCGACCTGAAAACCGACTACACCCCTTTCACC

GGCAACTACGGACAGCCTCACGTGGGACAGAAAGAGGTGTCCAACTTTACCATGGG

CAGCCCTCTGAGAGGCCCAGGACTTGAGGCCCTGTGTAAACAAGAGGGCGAGCTGG

ATCGGCGGAGCGTGATCTTTTCTAGCAGCGCCTGTGACCAGGTGTCCACCAGCGTGC

ACTCTTACAGCGGAGTGTCCAGCCTGGATAAGGACCTGTCTGAGCCCGTGCCTAAA

GGCCTGTGGGTTGGAGCTGGACAGAGCCTGCCAAGCAGCCAGGCTTATTCTCACGG

CGGACTGATGGCCGATCATCTGCCTGGTAGAATGCGGCCCAACACCAGCTGTCCCG

-continued

```
TGCCAATCAAAGTGTGCCCTAGAAGCCCTCCTCTGGAAACCCGGACCAGAACCAGC
AGCAGCTGTTCCAGCTACAGCTATGCCGAGGATGGAAGCGGCGGCAGCCCTTGTTC
ACTGCCTCTGTGCGAGTTTAGCAGCAGCCCCTGTTCTCAGGGCGCCAGATTTCTGGC
CACCGAGCATCAAGAACCTGGCCTGATGGGCGACGGCATGTACAATCAAGTGCGGC
CCCAGATTAAGTGCGAGCAGAGCTACGGCACCAACAGCTCTGATGAGAGCGGCAGC
TTTAGCGAGGCCGATAGCGAAAGCTGCCCCGTGCAGGATAGAGGCCAAGAAGTGA
AGCTGCCCTTTCCAGTGGATCAGATCACCGACCTGCCTCGGAACGACTTCCAGATGA
TGATCAAGATGCACAAGCTGACCTCCGAGCAGCTGGAATTCATCCACGACGTGCGG
CGGAGAAGCAAGAACAGAATCGCTGCCCAGCGGTGCCGGAAGAGAAAGCTGGACT
GCATCCAGAATCTGGAATGCGAGATCCGGAAGCTCGTGTGCGAAAAAGAGAAGCT
GCTGTCCGAGCGGAACCAGCTGAAGGCCTGTATGGGAGAGCTGCTGGACAACTTCA
GCTGTCTGTCTCAAGAAGTGTGCCGGGACATCCAGTCTCCAGAGCAGATTCAGGCC
CTGCACAGATACTGCCCTGTGCTGAGGCCTATGGATCTGCCTACAGCCAGCAGCATC
AACCCTGCTCCTCTGGGAGCCGAGCAGAATATTGCCGCCTCTCAGTGTGCCGTGGGC
GAGAATGTGCCTTGCTGTCTTGAACCTGGCGCCGCTCCTCCTGGACCTCCTTGGGCT
CCTTCTAACACCAGCGAGAACTGCACCTCCGGCAGAAGGCTGGAAGGCACAGATCC
TGGCACCTTCAGCGAAAGAGGCCCACCACTGGAACCCAGATCTCAGACCGTGACCG
TGGACTTCTGCCAAGAGATGACCGACAAGTGCACCACCGACGAGCAGCCCAGAAA
GGACTACACCAGGGCCAAGAGAAGCGGAAGTGGAGAGGGAAGAGGCTCCCTTCTG
ACATGCGGCGACGTGGAGGAGAACCCTGGACCTATGGGAGCTGGAGCTACCGGAA
GAGCTATGGACGGACCAAGACTTCTCCTGCTCCTCCTGCTGGGTGTGAGCCTGGGA
GGAGCTAAGGAGGCTTGCCCTACCGGACTGTACACCCACTCTGGCGAGTGCTGCAA
GGCTTGCAACCTGGGAGAGGGAGTGGCTCAACCCTGCGGAGCTAACCAAACTGTCT
GCGAGCCTTGCCTGGACTCTGTGACATTCTCCGACGTGGTGTCTGCCACCGAGCCTT
GCAAGCCTTGCACCGAATGCGTGGGCCTGCAAAGCATGAGCGCTCCTTGCGTGGAG
GCTGACGACGCTGTGTGCCGATGCGCTTACGGATACTACCAAGACGAGACCACCGG
AAGATGCGAGGCTTGCCGAGTGTGCGAGGCTGGAAGCGGACTCGTGTTCTCCTGCC
AAGACAAGCAAAACACCGTGTGTGAGGAATGCCCTGACGGAACCTACTCCGACGA
GGCTAACCACGTGGACCCTTGCCTGCCTTGCACCGTGTGTGAGGACACCGAGAGAC
AACTGAGGGAGTGCACAAGATGGGCTGACGCTGAGTGTGAGGAGATCCCTGGAAG
ATGGATCACAAGATCTACCCCTCCTGAGGGAAGCGACTCCACCGCTCCTTCCACCCA
AGAGCCCGAGGCTCCTCCTGAGCAAGACCTGATCGCAAGCACCGTGGCTGGAGTGG
TTACAACCGTGATGGGAAGCTCCCAACCCGTGGTTACAAGGGGAACCACCGACAAC
CTGATCCCTGTGTACTGCTCCATCCTGGCTGCTGTGGTGGTGGGATTGGTGGCCTAC
ATCGCTTTCAAGAGATGAATCGAT.
```

The present disclosure contemplates the use of, engineered cells, such as T cells, with chimeric antigen receptors (CARs) and engineered T cell receptors (TCRs) that are modified to modulate the expression of one or more of Bach2, TCF7, Blimp-1, and A20. In embodiments, one or more agents that inhibit the expression of one or more of Blimp-1, and A20 are co-expressed in a cell, such as a T cell, with a CAR or a TCR. In embodiments, one or more of TCF7 and Bach2 are co-expressed (for example from an exogenously introduced nucleic acid) in a cell, such as a T cell, with a CAR or a TCR. In embodiments, the nucleic acids encoding TCF7, Bach2, a CAR and/or a TCR are present in a single vector. In embodiments, the nucleic acids encoding TCF7, Bach2, a CAR and/or a TCR TCR are present in multiple vectors, such as two or more. In embodiments, one or more agents that inhibit the expression of one or more of Blimp-1, and A20 and one or more of TCF7 and Bach2 are co-expressed in a cell, such as a T cell, with a CAR or a TCR.

T cells may also be genetically engineered with vectors designed to express CARs that redirect cytotoxicity toward tumor cells. CARs are molecules that combine antibody based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins. Expression of CAR in T cells where the expression of one or more of Blimp-1, and A20 have been inhibited may promote CAR T cell expansion and effectiveness. In addition, over expression of one or more of Bach2 and TCF7 may promote CAR T cell expansion and effectiveness.

The CARs contemplated herein comprise an extracellular domain that binds to a specific target antigen (also referred to as a binding domain or antigen-specific binding domain), a transmembrane domain and an intracellular signaling domain. A characteristic of CARs are their ability to redirect immune effector cell specificity, thereby triggering proliferation, cytokine production, phagocytosis or production of molecules that may mediate cell death of the target antigen expressing cell in a major histocompatibility (MHC) independent manner, exploiting the cell specific targeting abilities of monoclonal antibodies, soluble ligands or cell specific co-receptors.

In some embodiments, a CAR comprises an extracellular binding domain including but not limited to an antibody or antigen binding fragment thereof, a tethered ligand, or the extracellular domain of a co-receptor, that specifically binds a target antigen.

By way of non-limiting examples, target antigens may include: HPV oncoproteins, including HPV-16 E6 and HPV-16 E7, alpha folate receptor, 5T4, $\alpha_v\beta6$ integrin, BCMA, TACI, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, FAP, fetal AchR, FRa, GD2, GD3, Glypican-3 (GPC3), HLA-A1+MAGEI, HLA-A2+MAGE1, HLAA3+MAGE1, HLA-A1+NY-ESO-1, HLA-A2+NY-ESO-1, HLA-A3+NY-ESO-1, IL-11Ra, IL-13Ra2, Lambda, Lewis-Y, Kappa, Mesothelin, Mud, Muc16, NCAM, NKG2D Ligands, NYE-S0-1, PRAME, PSCA, PSMA, RORI, SSX, Survivin, TAG72, TEMs, and VEGFRII; one or more hinge domains or spacer domains; a transmembrane domain including, but not limited to, transmembrane domains from CD8a, CD4, CD45, PD-1, and CD152; one or more intracellular costimulatory signaling domains including but not limited to intracellular costimulatory signaling domains from CD28, CD54 (ICAM), CD134 (0X40), CD137 (41BB), CD152 (CTLA4), CD273 (PD-L2), CD274 (PD-L1), and CD278 (ICOS); and a primary signaling domain from CD3ζ or FcRγ. In one embodiment described herein, the CAR binds to a tumor antigen comprising CLL-1, CD19, CD20, CD28, CD137 (4-1BB), Glypican-3 (GPC3), PSCA or PSMA.

A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8.alpha., CD8.beta., CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TN-FRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (0X40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA1-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof. In certain embodiments, a CAR does not comprise a CD28 hinge.

A transmembrane domain may be derived either from a natural or from a synthetic source. Where the source is natural, a domain may be derived from any membrane-bound or transmembrane protein. Exemplary transmembrane domains may be derived from (e.g., may comprise at least a transmembrane domain of) an alpha, beta or zeta chain of a T cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunogulobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CDS, CEACAM1, CRTAM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet.

In some embodiments, a signaling domain and/or activation domain comprises an immunoreceptor tyrosine-based activation motif (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)).

In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CD S, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

A CAR may comprise a costimulatory signaling domain, e.g., to increase signaling potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). Signals generated through a TCR alone may be insufficient for full activation of a T cell and a secondary or co-stimulatory signal may increase activation. Thus, in some embodiments, a signaling domain further comprises one or more additional signaling domains (e.g., costimulatory signaling domains) that activate one or more immune cell effector functions (e.g., a native immune cell effector function described herein). In some embodiments, a portion of such costimulatory signaling domains may be used, as long as the portion transduces the effector function signal. In some embodiments, a cytoplasmic domain described herein comprises one or more cytoplasmic sequences of a T cell co-receptor (or fragment thereof). Non-limiting examples of such T cell co-receptors comprise CD27, CD28, 4-1BB (CD137), OX40, CD30, CD40, PD-1, ICOS, lymphocyte function-associated antigen-1 (LFA-1), MYD88, CD2, CD7, LIGHT, NKG2C, B7-H3, and a ligand that binds with CD83.

In some embodiments, the CARs contemplated herein comprise an extracellular binding domain that specifically binds to a target polypeptide, e.g., target antigen, expressed on tumor cell. As used herein, the terms, "binding domain," "extracellular domain," "extracellular binding domain," "antigen-specific binding domain," "antigen binding domain" and "extracellular antigen specific binding domain," are used interchangeably and provide a CAR with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In some embodiments, the extracellular binding domain of a CAR comprises an antibody or antigen binding fragment thereof. An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments thereof. The term also includes genetically engineered forms such as chimeric antibodies (for example, humanized murine antibodies), hetero-conjugate antibodies (such as, bispecific antibodies) and antigen binding fragments thereof. See also, *Pierce Catalog and Handbook*, 1994-1995 (Pierce Chemical Co., Rockford, Ill.); Kuby, J., *Immunology*, 3rd Ed., W. H. Freeman & Co., New York, 1997.

In some embodiments, the target antigen is an epitope of an HPV oncoproteins, including HPV-16 E6 and HPV-16 E7, alpha folate receptor, 5T4, $\alpha_v\beta_6$ integrin, BCMA, TACI, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, F AP, fetal AchR, FRa, GD2, GD3, Glypican-3 (GPC3), HLA-A1+MAGEI, HLA-A2+MAGE1, HLAA3+MAGE1, HLA-A1+NY-ESO-1, HLA-A2+NY-ESO-1, HLA-A3+NY-ESO-1, IL-11Rα, IL-13Ra2, Lambda, Lewis-Y, Kappa, Mesothelin, Mud, Muc16, NCAM, NKG2D Ligands, NYE-S0-1, PRAME, PSCA, PSMA, RORI, SSX, Survivin, TAG72, TEMs, and VEGFRII polypeptide. In one embodiment described herein, the CAR binds to a tumor antigen epitope comprising CD19, CD20, CD28, CD137 (4-1BB), CLL-1, Glypican-3 (GPC3), PSCA or PSMA.

In some embodiments, a CAR contemplated herein comprises antigen-specific binding domain that may be a scFv (a murine, human or humanized scFv) that binds an antigen expressed on a cancer cell. In a certain embodiment, the scFv binds HPV oncoproteins, including HPV-16 E6 and HPV-16 E7, alpha folate receptor, 5T4, $\alpha_v\beta6$ integrin, BCMA, TACI, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, F AP, fetal AchR, FRa, GD2, GD3, Glypican-3 (GPC3), HLA-A1+MAGEI, HLA-A2+MAGE1, HLAA3+MAGE1, HLA-A1+NY-ESO-1, HLA-A2+NY-ESO-1, HLA-A3+NY-ESO-1, IL-11Ra, IL-13Ra2, Lambda, Lewis-Y, Kappa, Mesothelin, Mud, Muc16, NCAM, NKG2D Ligands, NYE-S0-1, PRAME, PSCA, PSMA, RORI, SSX, Survivin, TAG72, TEMs, and VEGFRII. In other embodiment described herein, the CAR comprises antigen specific binding domains scFv that bind CD19, CD20, CD28, CD137 (4-1BB), CLL-1, Glypican-3 (GPC3), PSCA or PSMA.

In certain embodiments, the CARs contemplated herein may comprise linker residues between the various domains, e.g., between VH and VL domains, added for appropriate spacing conformation of the molecule. CARs contemplated herein, may comprise one, two, three, four, or five or more linkers. In some embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers $(G_{1-5}S_{1-5})$n, where n is an integer of at least one, two, three, four, or five (SEQ ID NO: 15); glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses more phi-psi space than even alanine, and is much less restricted than residues with longer side chains (see Scheraga, *Rev. Computational Chem.* 11173-142 (1992)). Other linkers contemplated herein include Whitlow linkers (see Whitlow, *Protein Eng.* 6(8): 989-95 (1993)). The ordinarily skilled artisan will recognize that design of a CAR in some embodiments may include linkers that are all or partially flexible, such that the linker may include a flexible linker as well as one or more portions that confer less flexible structure to provide for a desired CAR structure. In one embodiment, any of the constructs described herein may comprise a "GS" linker. In another embodiment, any of the constructs described herein comprise a "GSG" linker.

In other embodiments, a CAR comprises a scFv that further comprises a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In one embodiment, the variable region linking sequence is 1, 2, 3, 4, 5, 6, 7, 8, 9, 10, 11, 12, 13, 14, 15, 16, 17, 18, 19, 20, 21, 22, 23, 24, 25, or more amino acids long.

In other embodiments, the binding domain of the CAR is followed by one or more "spacer domains," which refers to the region that moves the antigen binding domain away from the effector cell surface to enable proper cell/cell contact, antigen binding and activation (Patel et al., *Gene Therapy*, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain may include the amino acid sequence of a naturally occurring immunoglobulin hinge region or an altered immunoglobulin hinge region.

The binding domain of the CAR may generally be followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain. The hinge domain may be derived either from a natural, synthetic, semi-synthetic, or recombinant source. The hinge domain may include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8a, CD4, CD28 and CD7, which may be wild-type hinge regions from these molecules or may be altered, for example a truncated CD28 hinge domain. A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8.alpha., CD8.beta., CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (0X40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA1-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof. In certain embodiments, a CAR does not comprise a CD28 hinge. In another embodiment, the hinge domain comprises a CD8a hinge region.

The "transmembrane domain" is the portion of the CAR that fuses the extracellular binding portion and intracellular signaling domain and anchors the CAR to the plasma membrane of the immune effector cell. Exemplary transmembrane domains may be derived from (e.g., may comprise at least a transmembrane domain of) an alpha, beta or zeta chain of a T cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet.

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a signaling domain and/or activation domain comprises an immunoreceptor tyrosine-based activation motif (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)). In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain may be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal may also be required. Thus, T cell activation may be said to be mediated by two distinct classes of intracellular signaling domains: primary signaling domains that initiate antigen-dependent primary activation through the TCR (e.g., a TCR/CD3 complex) and costimulatory signaling domains that act in an antigen independent manner to provide a secondary or costimulatory signal. In some embodiments, a CAR contemplated herein comprises an intracellular signaling domain that comprises one or more "costimulatory signaling domain" and a "primary signaling domain."

Illustrative examples of ITAM containing primary signaling domains that are useful in the present disclosure include those derived from TCRζ, FcRγ, FcRβ, DAP12, CD3γ, CD3δ, CD3ε, CD3ζ, CD22, CD79a, CD79b, and CD66d. In some embodiments, a CAR comprises a CD3t primary signaling domain and one or more costimulatory signaling domains. The intracellular primary signaling and costimulatory signaling domains may be linked in any order in tandem to the carboxyl terminus of the transmembrane domain.

CARs contemplated herein comprise one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule. In some embodiments, costimulatory molecules may include CD27, CD28, CD137 (4-IBB), OX40 (CD134), CD30, CD40, PD-I, ICOS (CD278), CTLA4, LFA-1, CD2, CD7, LIGHT, TRIM, LCK3, SLAM, DAPIO, LAG3, HVEM, and NKD2C, and CD83.

The engineered CARs described herein may also comprise an N-terminal signal peptide or tag at the N-terminus of the scFv or antigen binding domain. In one embodiment, a heterologous signal peptide may be used. The antigen binding domain or scFV may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as the CAR constructs described herein, are generally expressed at the cell surface as a mature protein lacking the signal peptide, whereas the precursor form of the polypeptide includes the signal peptide. Any suitable signal sequence known in the art may be used. Similarly any known tag sequence known in the art may also be used.

T cells may also be genetically engineered with vectors designed to express CARs that redirect cytotoxicity toward tumor cells. CARs are molecules that combine antibody based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

The present disclosure contemplates the use of engineered cells, such T cells, engineered to inhibit the expression of one or more of Blimp-1, and A20 and/or increase the expression of one or more of Bach2 and TCF7, with T cell receptors (TCRs), for example, in T cell immunotherapy. Libraries of TCRs may be screened for their selectivity to target antigens. In this manner, natural TCRs, which have a high avidity and reactivity toward target antigens may be selected, cloned, and subsequently introduced into a population of T cells used for adoptive immunotherapy. Combining any TCR construct as described herein with a T cell modified to inhibit the expression of one or more of Blimp-1, and A20 may restore, maintain or enhance the therapeutic effect of the TCR containing cell. Furthermore, combining any TCR construct as described herein with a T cell modified to increase the expression of one or more of Bach2 and TCF7 may restore, maintain or enhance the therapeutic effect of TCR containing cell.

In one embodiment described herein, T cells are modified by introducing a polynucleotide encoding subunit of a TCR that may form TCRs that confer specificity to T cells for tumor cells expressing a target antigen. In some embodiments, the subunits have one or more amino acid substitutions, deletions, insertions, or modifications compared to the naturally occurring subunit, so long as the subunits retain the ability to form TCRs conferring upon transfected T cells the ability to home to target cells, and participate in immunologically-relevant cytokine signaling. The TCRs may also bind target cells displaying the relevant tumor-associated peptide with high avidity, and optionally mediate efficient killing of target cells presenting the relevant peptide in vivo.

The nucleic acids encoding TCRs may be isolated from their natural context in a (naturally-occurring) chromosome of a T cell, and may be incorporated into suitable vectors as described elsewhere herein. Both the nucleic acids and the vectors comprising them may be transferred into a cell, which cell may be a T cell. The modified T cells are then able to express one or more chains of a TCR (and in some aspects two chains) encoded by the transduced nucleic acid or nucleic acids. In some embodiments, the TCR is an exogenous TCR because it is introduced into T cells that do not normally express the introduced TCR. An aspect of the TCRs is that it has high avidity for a tumor antigen presented by a major histocompatibility complex (MEW) or similar immunological component. In contrast to TCRs, CARs are engineered to bind target antigens in an MHC independent manner.

The protein encoded by the nucleic acids described herein may be expressed with additional polypeptides attached to the amino-terminal or carboxyl-terminal portion of the α-chain or the β-chain of a TCR so long as the attached additional polypeptide does not interfere with the ability of the α-chain or the β-chain to form a functional T cell receptor and the MHC dependent antigen recognition.

Antigens that are recognized by the TCRs contemplated herein include, but are not limited to cancer antigens, including antigens on both hematological cancers and solid tumors and viral induced cancers. TCR therapy for the treatment of HPV induced cervical carcinoma is an area of interest that holds promise. The oncolytic proteins HPV-16 E6 and HPV-16 E7 may thus be potential target antigens for use with TCR.

Other illustrative antigens include, but are not limited HPV oncoproteins, including HPV-16 E6 and HPV-16 E7, alpha folate receptor, 5T4, $α_vβ_6$ integrin, BCMA, TACI, B7-H3, B7-H6, CAIX, CD19, CD20, CD22, CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, FAP, fetal AchR, FRa, GD2, GD3, Glypican-3 (GPC3), HLA-A1+MAGEI, HLA-A2+MAGE1, HLAA3+MAGE1, HLA-A1+NY-ESO-1, HLA-A2+NY-ESO-1, HLA-A3+NY-ESO-1, IL-11Ra, IL-13Ra2, Lambda, Lewis-Y, Kappa, Mesothelin, Mud, Muc16, NCAM, NKG2D Ligands, NY-ESO-1, PRAME, PSCA, PSMA, RORI, SSX, Survivin, TAG72, TEMs, and VEGFRII.

In embodiments, polynucleotides encoding one or more inhibitors of the expression Blimp-1, and A20. Further provided are polynucleotides encoding Bach2, TCF7 or function al fragments thereof. Further provided are polynucleotides encoding CARs and TCRs. As used herein, the terms "polynucleotide" or "nucleic acid" refers to messenger RNA (mRNA), RNA, genomic RNA (gRNA), plus strand RNA (RNA(+)), minus strand RNA (RNA(−)), complementary DNA (cDNA) or recombinant DNA. Polynucleotides include single and double stranded polynucleotides. Polynucleotides of the disclosure include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, the present disclosure contemplates, in part, polynucleotides comprising expression vectors, viral vectors, and transfer plasmids, and compositions, and cells comprising the same.

In some embodiments, polynucleotides are provided by this disclosure that encode at least about 5, 10, 25, 50, 100, 150, 200, 250, 300, 350, 400, 500, 1000, 1250, 1500, 1750, or 2000 or more contiguous amino acid residues of a polypeptide of the disclosure, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

The proteins (e.g., transcription factors, nucleases, TCR and CAR molecules), polynucleotides and/or compositions comprising the proteins and/or polynucleotides described herein may be delivered to a target cell by any suitable means, including, for example, by injection of the protein and/or mRNA components and expression of inhibitory RNAs, such as miRNAs and siRNAs.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions may be made to a reference polynucleotide whereby the expressed altered polynucleotide retains the biological function or activity of the reference polynucleotide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

The polynucleotides described herein, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, where the total length may be limited by the ease of preparation and use in the intended recombinant DNA protocol.

Polynucleotides may be prepared, manipulated and/or expressed using any of a variety of well-established techniques known and available in the art. In order to express a desired polypeptide, a nucleotide sequence encoding the polypeptide, may be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4N5-DEST™, pLenti6N5-DEST™, and pLenti6.2N5-GW/lacZ (Invitrogen) for lentivirus-mediated gene transfer and expression in mammalian cells. In some embodiments, the coding sequences of the chimeric proteins disclosed herein may be ligated into such expression vectors for the expression of the chimeric protein in mammalian cells.

The "control elements" or "regulatory sequences" present in an expression vector are those non-translated regions of the vector-origin of replication, selection cassettes, promoters, enhancers, translation initiation signals (Shine Dalgarno sequence or Kozak sequence), introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In other embodiments, a vector for use in practicing the embodiments described herein including, but not limited to expression vectors and viral vectors, will include exogenous, endogenous, or heterologous sequences such as promoters and/or enhancers. An "endogenous" control sequence is one which is naturally linked with a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" sequence is an exogenous sequence that may be from a different protein of the same species or a different species than the protein or cell being genetically manipulated.

The term "promoter" as used herein refers to a recognition site of a polynucleotide (DNA or RNA) to which an RNA polymerase binds. An RNA polymerase initiates and transcribes polynucleotides operably linked to the promoter. In some embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances may function independent of their orientation relative to another control sequence. An enhancer may function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide—of interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively. The present disclosure contemplates the use of any suitable cell line for use with the various constructs described herein including, but not limited to: T cells, CHO (e.g., CHO-S, CHO-K1, CHO-DG44, CHO-DUXB 11, CHO-DUKX, CHOK1 SV), BHK cells, MDCK cells, C3H 10T1/2 cells, FLY cells, Flp-cells, Psi-2 cells, BOSC 23 cells, P A317 cells, WEHI cells, COS cells, BSC 1 cells, BSC 40 cells, BMT 10 cells, Jurkat cells, VERO cells, MDCK, WI38, V79, B14 AF28-G3, BHK, HaK, NSO, SP2/0-Ag14, HeLa, HEK293 (e.g., HE 293-F, HEK293-H, HEK293-T), MRC5 cells, A549 cells, HTI080 cells, Hep cells, HEK cells, iHPC cells, 293 cells, 293T cells, B-50 cells, 3T3 cells, NIH3T3 cells, NK cells, HepG2 cells, Saos-2 cells, Huh7 cells, HeLa cells, W163 cells, 211 cells, and 211A, cells or any other suitable cell line and perC6 cells as well as insect cells such as *Spodoptera fugiperda* (Sf), or fungal cells such as *Saccharomyces, Pichia* and *Schizosaccharomyces*. Suitable cells also include stem cells such as, by way of example, embryonic stem cells, induced pluripotent stem cells (iPS cells), hematopoietic stem cells, neuronal stem cells and mesenchymal stem cells.

Illustrative ubiquitous expression control sequences suitable for use in some embodiments of the disclosure include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, HS, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B 1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-I (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter (Challita et al., *J Virol.* 69(2):748-55 (1995)).

As used herein, "conditional expression" may refer to any type of conditional expression including, but not limited to, inducible expression; repressible expression; expression in cells or tissues having a physiological, biological, or disease state, etc. This definition is not intended to exclude cell type or tissue specific expression. Certain embodiments described herein provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

Conditional expression may also be achieved by using a site specific DNA recombinase. According to certain embodiments of the disclosure the vector comprises at least one (typically two) site(s) for recombination mediated by a site specific recombinase. As used herein, the terms "recombinase" or "site specific recombinase" include excisive or integrative proteins, enzymes, cofactors or associated proteins that are involved in recombination reactions involving one or more recombination sites (e.g., two, three, four, five, seven, ten, twelve, fifteen, twenty, thirty, fifty, etc.), which may be wild-type proteins (see Landy, *Current Opinion in Biotechnology* 3:699-707 (1993)), or mutants, derivatives (e.g., fusion proteins containing the recombination protein sequences or fragments thereof), fragments, and variants thereof. Illustrative examples of recombinases suitable for use in some embodiments of the present disclosure include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The present disclosure contemplates, co-expression of polynucleotides comprising inhibitors of the expression Blimp-1, and A20 and/or polynucleotides encoding Bach2, TCF7 with engineered TCR and CAR polypeptides constructs, and fragments thereof, cells and compositions comprising the same, and vectors that express polypeptides. "Polypeptide," "polypeptide fragment," "peptide" and "protein" are, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the polypeptides contemplated herein comprise a signal (or leader) sequence at the N-terminal end of the protein, which co-translationally or post-translationally directs transfer of the protein. Illustrative examples of suitable signal sequences useful in disclosed herein include, but are not limited to the IgG 1 heavy chain signal sequence and the CD8a signal sequence. Polypeptides may be prepared using any of a variety of well-known recombinant and/or synthetic techniques.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. Preferably, polypeptides of the disclosure include polypeptides having at least about 50%, 60%, 65%, 70%, 75%, 85%, 90%, 95%, 98%, or 99% amino acid identity thereto. Polypeptides of the disclosure include variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. Polypeptides include "polypeptide fragments." Polypeptide fragments refer to a polypeptide, which may be monomeric or multimeric that has an amino-terminal deletion, a carboxyl-terminal deletion, and/or an internal deletion or substitution of a naturally-occurring or recombinantly-produced polypeptide. In certain embodiments, a polypeptide fragment may comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides of the present disclosure may be altered in various ways including amino acid substitutions, deletions, truncations, and insertions. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, Proc. Natl. Acad. Sci. USA. 82: 488-492), Kunkel et al., (1987, Methods in Enzymol, 154: 367-382), U.S. Pat. No. 4,873, 192, Watson, J. D. et al., (Molecular Biology of the Gene, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present disclosure and still obtain a functional molecule that encodes a variant or derivative polypeptide with desirable characteristics.

Polypeptide variants further include glycosylated forms, aggregative conjugates with other molecules, and covalent conjugates with unrelated chemical moieties (e.g., pegylated molecules). Covalent variants may be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Where expression of two or more polypeptides is desired, the polynucleotide sequences encoding them may be separated by an IRES sequence as discussed elsewhere herein. In another embodiment, two or more polypeptides may be expressed as a fusion protein that comprises one or more self-cleaving polypeptide sequences.

Polypeptides of the present disclosure include fusion polypeptides. In some embodiments, fusion polypeptides and polynucleotides encoding fusion polypeptides are provided. Fusion polypeptides and fusion proteins refer to a polypeptide having at least two, three, four, five, six, seven, eight, nine, or ten or more polypeptide segments. Fusion polypeptides are typically linked C-terminus to N-terminus, although they may also be linked C-terminus to C-terminus, N-terminus to N-terminus, or N-terminus to C-terminus. The polypeptides of the fusion protein may be in any order or a specified order. Fusion polypeptides or fusion proteins may also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other common techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, polypeptide site may be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. Traffic, 5(8); 616-26).

Suitable protease cleavages sites and self-cleaving peptides are known to the skilled person (see, e.g., in Ryan et al., 1997. J Gener. Viral. 78, 699-722; Scymczak et al. (2004) Nature Biotech. 5, 589-594). Exemplary protease cleavage sites include, but are not limited to the cleavage sites of potyvirus Nia proteases (e.g., tobacco etch virus protease), potyvirus HC proteases, potyvirus P1 (P35) proteases, byovirus Nia proteases, byovirus RNA-2-encoded proteases, aphthovirus L proteases, enterovirus 2A proteases, rhinovirus 2A proteases, picoma 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites may be used. In other embodiments, self-cleaving peptides may include those polypeptide sequences obtained from potyvirus and cardiovirus 2A peptides, FMDV (foot-and-mouth disease virus), equine rhinitis A virus, Thosea asigna virus and porcine teschovirus. In other embodiments, the self-cleaving polypeptide site comprises a 2A or 2A-like site, sequence or domain (Donnelly et al., 2001. J Gen. Viral. 82:1027-1041).

Generally, it is understood that any appropriate viral vector may be used for transduction of the engineered constructs described herein. In one embodiment described herein, a cell (e.g., T cell) is transduced with or more retroviral vectors, e.g., a lentiviral vector, encoding an engineered a TCR or CAR and one or more agents that inhibit the expression of one or more of Bach2, TCF7, Blimp-1, and A20. The transduced T cells elicits a stable, long-term, and persistent T cell response.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in some embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis encephalitis virus (CAEV); equine infectious anemia virus (EIAV); feline immunodeficiency virus (FIV); bovine immune deficiency virus (BIV); and simian immunodeficiency virus (SIV).

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-retroviral viral sequences. In one embodiment, a hybrid vector refers to a vector or transfer plasmid comprising retroviral e.g., lentiviral, sequences for reverse transcription, replication, integration and/or packaging.

In some embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the disclosure and are present in DNA form in the DNA plasmids of the disclosure. In one embodiment described herein, the expression vector is a lentivirus expression vector.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, Rand U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R, and U5. The U3 region contains the enhancer and promoter elements. The U5 region is the sequence between the primer binding site and the R region and contains the polyadenylation sequence. The R (repeat) region is flanked by the U3 and U5 regions. The LTR is composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. J of Virology, Vol. 69, No. 4; pp. 2101-2109. Several retroviral vectors use the minimal packaging signal (also referred to as the psi ['P] sequence) needed for encapsidation of the viral genome. Thus, as used herein, the terms "packaging sequence," "packaging signal," "psi" and the symbol "'P," are used in reference to the non-coding sequence required for encapsidation of retroviral RNA strands during viral particle formation.

In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the disclosure, the 3'LTR is modified such that the U5 region is replaced, for example, with an ideal poly(A) sequence. It should be noted that modifications to the LTRs such as modifications to the 3'LTR, the 5'LTR, or both 3' and 5'LTRs, are also contemplated herein.

An additional safety enhancement is provided by replacing the U3 region of the 5'LTR with a heterologous promoter to drive transcription of the viral genome during production of viral particles. Examples of heterologous promoters which may be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter may be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a retrovirus, e.g., HIV-I or HIV-2. Suitable FLAP elements are described in U.S. Pat. No. 6,682,907 and in Zennou, et al., 2000, Cell, 101: 173. During HIV-I reverse transcription, central initiation of the plus-strand DNA at the central polypurine tract (cPPT) and central termination at the central termination sequence (CTS) lead to the formation of a three-stranded DNA structure: the HIV-I central DNA flap. While not wishing to be bound by any theory, the DNA flap may act as a cis-active determinant of lentiviral genome nuclear import and/or may increase the titer of the virus.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J Virol. 65: 1053; and Cullen et al., 1991. Cell 58: 423), and the hepatitis B virus post-transcriptional regulatory element (HPRE). Generally, the RNA export element is placed within the 3' UTR of a gene, and may be inserted as one or multiple copies.

In other embodiments, expression of heterologous sequences in viral vectors is increased by incorporating post-transcriptional regulatory elements, efficient polyadenylation sites, and optionally, transcription termination signals into the vectors. A variety of posttranscriptional regulatory elements may increase expression of a heterologous nucleic acid at the protein, e.g., woodchuck hepatitis virus post-transcriptional regulatory element (WPRE; Zufferey et al., 1999, J Virol., 73:2886); the post-transcriptional regulatory element present in hepatitis B virus (HPRE) (Huang et al., Mol. Cell. Biol., 5:3864); and the like (Liu et al., 1995, Genes Dev., 9:1766).

In some embodiments, vectors may include regulatory oligonucleotides having transcriptional or translational regulatory activity. Such an oligonucleotide can be used in a variety of gene expression configurations for regulating control of expression. A transcriptional regulatory oligonucleotide, can increase (enhance) or decrease (silence) the level of expression of a recombinant expression construct. Regulatory oligonucleotides may selectively regulate expression in a context specific manner, including, for example, for conferring tissue specific, developmental stage specific, or the like expression of the polynucleotide, including constitutive or inducible expression. A regulatory oligonucleotide of the disclosure also can be a component of an expression vector or of a recombinant nucleic acid molecule comprising the regulatory oligonucleotide operatively linked to an expressible polynucleotide. A regulatory element can be of various lengths from a few nucleotides to several hundred nucleotides.

Elements directing the efficient termination and polyadenylation of the heterologous nucleic acid transcripts increases heterologous gene expression. Transcription termination signals are generally found downstream of the polyadenylation signal. In some embodiments, vectors comprise a polyadenylation sequence 3' of a polynucleotide encoding a polypeptide to be expressed. The term "poly A site" or "poly A sequence" as used herein denotes a DNA sequence which directs both the termination and polyadenylation of the nascent RNA transcript by RNA polymerase II. Polyadenylation sequences may promote mRNA stability by addition of a poly A tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of poly A signals that may be used in a vector of the disclosure, includes an ideal poly A sequence (e.g., AATAAA, ATTAAA, AGTAAA), a bovine growth hormone poly A sequence (BGHpA), a rabbit β-globin poly A sequence (rβgpA), or another suitable heterologous or endogenous poly A sequence known in the art.

In one embodiment described herein, the vectors described herein comprise a promoter operably linked to a polynucleotide encoding and one or more agents that inhibit the expression of one or more of Blimp-1, and A20. In one embodiment described herein, the vectors described herein comprise a promoter operably linked to a polynucleotide encoding one or more of Bach2 and TCF7. In one embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid sequence encoding Bach2 according to SEQ ID NO: 4. In one embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid sequence set forth as SEQ ID NO: 5. In one embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid sequence encoding TCF7 according to SEQ ID NO: 8. In one embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid sequence set forth as SEQ ID NO: 9.

In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to a nucleic acid sequence encoding SEQ ID NO: 4 operably linked to a nucleic acid sequence encoding an engineered TCR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to a nucleic acid sequence encoding SEQ ID NO: 4 operably linked to a nucleic acid sequence encoding an engineered CAR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to a nucleic acid sequence encoding SEQ ID NO: 8 operably linked to a nucleic acid sequence encoding an engineered TCR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to a nucleic acid sequence encoding SEQ ID NO:8 operably linked to a nucleic acid sequence encoding an engineered CAR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 5 operably linked to a nucleic acid sequence encoding an engineered TCR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 5 operably linked to a nucleic acid sequence encoding an engineered CAR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 9 operably linked to a nucleic acid sequence encoding an engineered TCR. In another embodiment described herein, the expression vector comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 9 operably linked to a nucleic acid sequence encoding an engineered CAR.

Also described herein are "codon-optimized" nucleic acids. A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells) by replacing at least one, more than one, or a significant number, of codons of the native sequence with codons that are more frequently or most frequently used in the genes of that species. Codon optimization does not alter the amino acid sequence of the encoded protein. In some examples, codon optimization is performed to decrease the possibility of unwanted recombination and/or splicing events.

The codon-optimized nucleotide sequences presented in the instant disclosure can present improved properties related to expression efficacy. In some embodiments, the DNA sequence to be transcribed may be optimized to facilitate more efficient transcription and/or translation. In some embodiments, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding.

The vectors may have one or more LTRs, wherein any LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences), and may optionally comprise a WPRE or HPRE. The skilled artisan would appreciate that many other different embodiments may be fashioned from the existing embodiments of the disclosure.

A "host cell" includes cells transfected, infected, or transduced in vivo, ex vivo, or in vitro with a recombinant vector or a polynucleotide of the disclosure. Host cells may include packaging cells, producer cells, and cells infected with viral vectors. In some embodiments, host cells infected with viral vector of the disclosure are administered to a subject in need of therapy. In certain embodiments, the term "target cell" is used interchangeably with host cell and refers to transfected, infected, or transduced cells of a desired cell type. In some embodiments, the target cell is a T cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present disclosure may be introduced into a packaging cell line, via transfection, transduction or infection, to generate a producer cell or cell line. The packaging vectors of the present disclosure may be introduced into human cells or cell lines by common methods including, e.g., calcium phosphate transfection, lipofection or electroporation. In some embodiments, the packaging vectors are introduced into the cells together with a dominant selectable marker, such as neomycin, hygromycin, puromycin, blasticidin, zeocin, thymidine kinase, DHFR, Gln synthetase or ADA, followed by selection in the presence of the appropriate drug and isolation of clones. A selectable marker gene may be linked physically to genes encoding by the packaging vector, e.g., by IRES or self-cleaving viral peptides.

Viral envelope proteins (env) determine the range of host cells which may ultimately be infected and transformed by recombinant retroviruses generated from the cell lines. In the case of lentiviruses, such as HIV-1, HIV-2, SIV, FIV and EIV, the env proteins include gp41 and gp120. In some embodiments, the viral env proteins expressed by packaging cells of the disclosure are encoded on a separate vector from the viral gag and pol genes, as has been previously described.

Illustrative examples of retroviral-derived env genes which may be employed in the embodiments described herein include, but are not limited to: MLV envelopes, IOAI envelope, BAEV, FeLV-B, RDI 14, SSAV, Ebola, Sendai, FPV (Fowl plague virus), and influenza virus envelopes. Similarly, genes encoding envelopes from RNA viruses (e.g., RNA virus families of Picomaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BL V, EBV, CAEV, SNV, ChTL V, STLV, MPMV SMRV, RAV, FuSV, MH2, AEV, AMV, CTIO, and EIAV.

In other embodiments, envelope proteins for pseudotyping a virus of present disclosure include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpes viruses such as Herpes simplex virus types 1 and 2, varicella zoster, cytomegalovirus, Epsteing Barr virus (EBV), human herpesviruses (HHV), human herpesvirus type 6 and 8, Human immunodeficiency virus (HIV), papilloma virus, murine gamma herpes virus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-Co V), West Nile virus, or any encephaliltis causing virus.

The terms "pseudotype" or "pseudotyping" as used herein, refer to a virus whose viral envelope proteins have been substituted with those of another virus possessing other characteristics. For example, HIV may be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line may be employed to prepare packaging cells of the disclosure. Generally, the cells are mammalian cells. In another embodiment, the cells used to produce the packaging cell line are human cells. Suitable cell lines which may be used to produce the packaging cell line include, for example, CHO cells, BHK cells, MDCK cells, C3H 10T1/2 cells, FLY cells, Psi-2 cells, BOSC 23 cells, P A317 cells, WEHI cells, COS cells, BSC 1 cells, BSC 40 cells, BMT 10 cells, VERO cells, W138 cells, MRC5 cells, A549 cells, HTIO80 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J Virol.* 66:5110-5113. Infectious virus particles may be collected from the packaging cells using conventional techniques. For example, the infectious particles may be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a target cell, e.g., a T cell, is "transduced" if it comprises a gene or other polynucleotide sequence delivered to the cell by infection using a viral or retroviral vector. In some embodiments, a transduced cell comprises one or more genes or other polynucleotide sequences delivered by a retroviral or lentiviral vector in its cellular genome.

In some embodiments, host cells expressing a TCR and/or a CAR are provided in which the expression of one or more of Blimp-1, and A20 have been inhibited and/or the expression of one or more of Bach2 and TCF7 is increased. The host cells may be transduced with one or more viral vectors comprising nucleic acid sequences encoding one or more polypeptides expressing a TCR and/or a CAR and inhibitors of the expression of one or more of Blimp-1, and A20 are provided. The host cells may be transduced with one or more viral vectors comprising nucleic acid sequences encoding one or more polypeptides expressing a TCR and/or a CAR and one or more of Bach2 and TCF7. The host cells may be administered to a subject to treat and/or prevent malignancies. Other methods relating to the use of viral vectors in gene therapy, which may be utilized according to certain embodiments of the present disclosure, may be found in, e.g., Kay, M. A. (1997) *Chest* 111(6 Supp.): 138S-142S; Ferry, N. and Heard, J. M. (1998) *Hum. Gene Ther.* 9:1975-81; Shiratory, Y. et al., (1999) *Liver* 19:265-74; Oka, K. et al., (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J Hepatol.* 23:746-58; Brody, S. L. and Crystal, R. G. (1994) *Ann. NY Acad. Sci.* 716:90-101; Strayer, D. S. (1999) *Expert Opin. Investig. Drugs* 8:2159-2172; Smith-Arica, J. R. and Bartlett, J. S. (2001) *Curr. Cardiol. Rep.* 3:43-49; and Lee, H. C. et al., (2000) *Nature* 408:483-8.

Methods of non-viral delivery of nucleic acids include electroporation, lipofection, microinjection, biolistics, virosomes, liposomes, lipid nanoparticles, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein. Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™, and Lipofectamine™ RNAiMAX). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al, Cancer Gene Ther. 2:291-297 (1995); Behr et al, Bioconjugate Chem. 5:382-389 (1994); Remy et al, Bioconjugate Chem. 5:647-654 (1994); Gao et al, Gene Therapy 2:710-722 (1995); Ahmad et al, Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al, Virology 160:38-47 (1987); U.S. Pat. No. 4,797,368; WO 93/24641; Kotin, Human Gene Therapy 5:793-801 (1994); Muzyczka, J. Clin. Invest. 94: 1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS USA 81:6466-6470 (1984); and Samulski et al., J. Virol. 63:03822-3828 (1989).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., Gene Ther. 9:748-55 (1996)). Other AAV serotypes, including AAV1, AAV3, AAV4, AAV5, AAV6, AAV8, AAV8.2, AAV9 and AAVrhlO and pseudo-typed AAV such as AAV2/8, AAV2/5 and AAV2/6 can also be used in accordance with the present disclosure.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al, Hum. Gene Ther. 7: 1083-9 (1998)). Additional examples of the use of adenovirus vectors for gene transfer in clinical trials include Rosenecker et al, Infection 24: 1 5-10 (1996); Sterman et al, Hum. Gene Ther. 9:7 1083-1089 (1998); Welsh et al., Hum. Gene Ther. 2:205-18 (1995); Alvarez et al., Hum. Gene Ther. 5:597-613 (1997); Topf et al, Gene Ther. 5:507-513 (1998); Sterman et al, Hum. Gene Ther. 7: 1083-1089 (1998).

Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

The compositions described herein may comprise one or more polynucleotides, polypeptides, vectors comprising same, and T cell compositions, as contemplated herein. One embodiment described herein is a composition comprising a modified T cell that co-express a TCR and/or a CAR and one or more inhibitors of the expression of one or more of Blimp-1, and A20 or a TCF7 or Bach2 polypeptide or fragment thereof (as described above). Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the present disclosure may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In one embodiment described herein, compositions of the present disclosure comprise an amount of modified T cells contemplated herein. It may generally be stated that a pharmaceutical composition comprising the T cells contemplated herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of cells will depend upon the ultimate use for which the composition is intended as will the type of cells included therein. T cells modified to express a TCR or CAR may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-7, IL-15, IL-12, TNF-alpha, IL-18, and TNF-beta, GM-CSF, IL-4, IL-13, Flt3-L, RANTES, MIP1α, etc.) as described herein to enhance engraftment and function of infused T cells.

Generally, compositions comprising the cells activated and expanded as described herein may be utilized in the treatment and prevention of diseases that arise in individuals who are immunocompromised or immunosuppressed. In some, compositions comprising the modified T cells contemplated herein are used in the treatment of cancers. The modified T cells described herein may be administered either alone, or as a pharmaceutical composition in combination with carriers, diluents, excipients, and/or with other components such as IL-2, IL-7, and/or IL-15 or other cytokines or cell populations. In some embodiments, pharmaceutical compositions contemplated herein comprise an amount of genetically modified T cells, in combination with one or more pharmaceutically or physiologically acceptable carriers, diluents or excipients.

Pharmaceutical compositions comprising modified T cells contemplated herein may further comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Sterile injectable pharmaceutical composition are also included.

In some embodiments, compositions contemplated herein comprise an effective amount of an expanded modified T cell composition, alone or in combination with one or more therapeutic agents. Thus, the T cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics and anti-viral agents. Such therapeutic agents may be accepted in the art as a treatment for a disease state as described herein, such as a cancer. In one embodiment the compositions contemplated herein may also be administered with inhibitors of TGF-β, for example the small molecule inhibitor LY55299. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising T cells contemplated herein may be administered in conjunction with any number of chemotherapeutic agents. Illustrative examples of chemotherapeutic agents include but are not limited to alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®' Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RPS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising T cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

In some embodiments, NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol or proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary disease-modifying anti-rheumatic drugs (DMARDs) include azathioprine, cyclophosphamide, cyclosporine, methotrexate, penicillamine, leflunomide, sulfasalazine, hydroxychloroquine, Gold (oral (auranofin) and intramuscular) and minocycline.

In other embodiments, the therapeutic antibodies suitable for combination with the CAR modified T cells contemplated herein, include but are not limited to, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

In some embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, chemokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-15, a tumor necrosis factor such as TNF-α or TNF-β; and other polypeptide factors including LIF and kit ligand (KL). As used herein, the term cytokine includes proteins from natural sources or from recombinant cell culture, and biologically active equivalents of the native sequence cytokines.

The present disclosure contemplates, in part, genetically modified T cell redirected to a target cell, e.g., a tumor or cancer cell, and that comprises expressing co-expressing a TCR and/or a CAR and one or more inhibitors of the expression of one or more of Blimp-1, and A20 or a TCF7 or Bach2 polypeptide or fragment thereof (as described above). Cancer cells may also spread to other parts of the body through the blood and lymph systems. There are several types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In one embodiment, the target cell expresses an antigen, e.g., target antigen. In one embodiment, the target cell is a pancreatic parenchymal cell, pancreatic duct cell, hepatic cell, cardiac muscle cell, skeletal muscle cell, osteoblast, skeletal myoblast, neuron, vascular endothelial cell, pigment cell, smooth muscle cell, glial cell, fat cell, bone cell, chondrocyte, pancreatic islet cell, CNS cell, PNS cell, liver cell, adipose cell, hepatic cell, renal cell, lung cell, skin cell, ovary cell, follicular cell, epithelial cell, immune cell, or an endothelial cell.

In certain embodiments, the target cell is part of a pancreatic tissue, neural tissue, cardiac tissue, bone marrow, muscle tissue, bone tissue, skin tissue, liver tissue, hair follicles, vascular tissue, adipose tissue, lung tissue, and kidney tissue.

In a one embodiment, the target cell is a tumor cell. In another embodiment, the target cell is a cancer cell, such as a cell in a patient with cancer. Exemplary cells that may be killed with the disclosed methods include cells of the following tumors: a liquid tumor such as a leukemia, including acute leukemia (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrom's macroglobulinemia, heavy chain disease).

In another embodiment, the cell is a solid tumor cell, such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinoma, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In one embodiment, the cancer may comprise Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In one embodiment, the target cell is a malignant cell of the liver, pancreas, lung, breast, bladder, brain, bone, thyroid, kidney, skin, and hematopoietic system. In another embodiment, the target cell is a cell in a liver cancer, pancreatic cancer, lung cancer, breast cancer, bladder cancer, brain cancer, bone cancer, thyroid cancer, kidney cancer, skin cancer, or hematological cancer. In another embodiment, the target cell is a cell, e.g., a cancer cell infected by a virus, including but not limited to CMV, HPV, and EBV.

In one embodiment, the target antigen is directed to or is an epitope of HPV oncoproteins, including HPV-16 E6 and HPV-16 E7, alpha folate receptor, 5T4, $\alpha_v\beta_6$ integrin, BCMA, TACI, B7-H3, B7-H6, CAIX, CD19, CD20, CD22-CD28, CD30, CD33, CD44, CD44v6, CD44v7/8, CD70, CD79a, CD79b, CD123, CD137 (4-1BB), CD138, CD171, CEA, CSPG4, CLL-1, EGFR, EGFR family including ErbB2 (HERII), EGFRvIII, EGP2, EGP40, EPCAM, EphA2, EpCAM, F AP, fetal AchR, FRa, GD2, GD3, Glypican-3 (GPC3), HLA-A1+MAGEI, HLA-A2+MAGE1, HLAA3+MAGE1, HLA-A1+NY-ESO-1, HLA-A2+NY-ESO-1, HLA-A3+NY-ESO-1, IL-11Ra, IL-13Ra2, Lambda, Lewis-Y, Kappa, Mesothelin, Mud, Muc16, NCAM, NKG2D Ligands, NYE-S0-1, PRAME, PSCA, PSMA, RORI, SSX, Survivin, TAG72, TEMs, and VEGFRII.

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Envinia; Klebsiella; Proteus; Salmonella*, e.g., *Salmonella typhimurium; Serratia*, e.g., *Serratia marcescans*, and *Shigella; Bacilli* such as *B. subtilis* and *B. licheniformis; Pseudomonas* such as *P. aeruginosa;* and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof. Unlike antibody therapies or standalone TCR or CAR modified T cells, T cells (or any cells as described above) modified expressing a TCR and/or a CAR and one or more of Bach2 and TCF7 or an inhibitor of the expression of one or more of Blimp-1, and A20 increased are able to not only replicate in vivo, and thus contribute to long-term persistence that may lead to sustained cancer therapy.

Another embodiment described herein is a method of treating a cancer in a subject in need thereof comprising administering an effective amount, e.g., therapeutically effective amount of a composition comprising T cells co-express a TCR and/or a CAR and/or one or more of Bach2 and TCF7 and/or or an inhibitor of the expression of one or more of Blimp-1, and A20 or fragment thereof (as described above). The quantity and frequency of administration will be determined by such factors as the condition of the patient, and the type and severity of the patient's disease, although appropriate dosages may be determined by clinical trials.

Another embodiment described herein is a method of treating a hepatic cancer in a subject in need thereof comprising administering an effective amount, e.g., therapeutically effective amount of a composition comprising T cells co-express a TCR and/or a CAR and/or one or more of Bach2 and TCF7 and/or or an inhibitor of the expression of one or more of Blimp-1, and A20 or fragment thereof (as described above). The quantity and frequency of administration will be determined by such factors as the condition of the patient, and the type and severity of the patient's disease, although appropriate dosages may be determined by clinical trials.

In other embodiments, compositions comprising T cell genetically modified with a vector comprising a promoter operably linked to a polynucleotide encoding a expressing a TCR and/or a CAR and and/or one or more of Bach2 and TCF7 and/or or an inhibitor of the expression of one or more of Blimp-1, and A20 or fragment thereof (as described above)constructs described herein, are used in the treatment of solid tumors or cancers including, without limitation, liver cancer, pancreatic cancer, lung cancer, breast cancer, bladder cancer, brain cancer, bone cancer, thyroid cancer, kidney cancer, skin cancer or virus induced cancers.

In some embodiments, compositions comprising T cell genetically modified with a vector comprising a promoter operably linked to a polynucleotide encoding a TCR and/or a CAR and/or one or more of Bach2 and TCF7 and/or or an inhibitor of the expression of one or more of Blimp-1, and A20 or fragment thereof (as described above), comprises an antigen-specific binding domain that binds an epitope of BCMA, TACI, CD19, CD20, CD28, CD137 (4-1BB), CLL-1, GPC3, PSMA or PSMA are used in the treatment of various cancers.

In other embodiments, methods comprising administering a therapeutically effective amount of modified T cells contemplated herein or a composition comprising the same, to a patient in need thereof, alone or in combination with one or more therapeutic agents, are provided. In certain embodiments, the cells of the disclosure are used in the treatment of patients at risk for developing a cancer. Thus, the present disclosure provides methods for the treatment or prevention of a cancer comprising administering to a subject in need thereof, a therapeutically effective amount of the modified T cells of the disclosure.

One of ordinary skill in the art would recognize that multiple administrations of the compositions of the disclosure may be required to effect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom according to the present disclosure, and reinfuse the patient with these activated and expanded T cells. This process may be carried out multiple times every few weeks. In certain embodiments, T cells may be activated from blood draws of from 10cc to 400cc. Not to be bound by theory, using this multiple blood draw/multiple reinfusion protocol may serve to select out certain populations of T cells.

The administration of the compositions contemplated herein may be carried out in any convenient manner, including by aerosol inhalation, injection, ingestion, transfusion, implantation or transplantation. In some embodiments, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a cancer in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present disclosure, which are well described in the art; e.g., *Current Protocols in Immunology*, Edited by: John E. Coligan, Ada M. Kruisbeek, David H. Margulies, Ethan M. Shevach, Warren Strober (2001) John Wiley & Sons, NY, N.Y.

In the case of T cell-mediated killing, CAR-ligand binding initiates CAR signaling to the T cell, resulting in activation of a variety of T cell signaling pathways that induce the T cell to produce or release proteins capable of inducing target cell apoptosis by various mechanisms. These T cell-mediated mechanisms include (but are not limited to) the transfer of intracellular cytotoxic granules from the T cell into the target cell, T cell secretion of proinflammatory cytokines that may induce target cell killing directly (or indirectly via recruitment of other killer effector cells), and up regulation of death receptor ligands (e.g. FasL) on the T cell surface that induce target cell apoptosis following binding to their cognate death receptor (e.g. Fas) on the target cell.

One embodiment described herein is a method of treating a subject diagnosed with a cancer, comprising removing T cells from the subject, genetically modifying said T cells with a vector comprising a nucleic acid encoding a TCR and/or a CAR and and/or one or more of Bach2 and TCF7 and/or or an inhibitor of the expression of one or more of Blimp-1, and A20 or fragment thereof (as described above), thereby producing a population of modified T cells, and administering the population of modified T cells to the same subject.

In certain embodiments, the present disclosure also provides methods for stimulating an effector cell mediated immune modulator response to a target cell population in a subject comprising the steps of administering to the subject an immune effector cell population expressing a nucleic acid construct encoding a TCR and/or a CAR and/or one or more of Bach2 and TCF7 and/or or an inhibitor of the expression of one or more of Blimp-1, and A20 or fragment thereof (as described above).

The methods for administering the cell compositions described herein includes any method which is effective to result in reintroduction of ex vivo genetically modified immune effector cells that either directly express an TCR or CAR in the subject or on reintroduction of the genetically modified progenitors of immune effector cells that on introduction into a subject differentiate into mature immune effector cells that express the TCR or CAR. One method comprises transducing peripheral blood T cells ex vivo with a nucleic acid construct in accordance with the present disclosure and returning the transduced cells into the subject.

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those skilled in the art will readily recognize a variety of noncritical parameters that could be changed or modified to yield similar results.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present disclosure. To the extent that any of the definitions or terms provided in the references incorporated by reference differ from the terms and discussion provided herein, the present terms and definitions control. The contents of all references cited throughout this application are expressly incorporated herein by reference.

EXAMPLES

Example 1

Less differentiated cells (for example, Naïve and CM) can proliferate robustly and have greater anti-tumor efficacy than more differentiated cells (for example, EM/TEMRA) in vivo. To better understand the mechanism underlying the these differences at the gene expression level RNAseq was performed to examine genome-wide RNA expression of transcription factors highly expressed in sorted, unactivated (day 0 cells=d0) and subsequently activated and CD19 CAR transduced T cell memory subsets (day 10=d10) in two healthy donors (Donor 1 and Donor 2). The T cells were classified according to state of differentiation Naïve=N, Central memory=CM, Effector memory, EM, TEMRA or bulk T cells (see below). For RNAseq analysis, 45,000,000 single-end reads per sample were obtained with a minimum read depth of 1×75 bp.

CD4 and CD8 T Cell Isolation

CD4$^+$ and CD8$^+$ T cells were isolated by positive selection from apheresis material from healthy donors sung CliniMACS® beads and CliniMACS® instrument. Cells were frozen at least at 25×10$^6$ cells/mL in and frozen down in CryoStor® cell cryopreservation media (Sigma Aldrich®) and stored under liquid nitrogen. Cells were used to generate anti-CD19 CAR T-cell products. As a controls, non-transduced (NTD) T cells were generated in parallel.

Memory Phenotyping

T cells were stained on day 7-10 of culture with CD4, CD8, CCR7, CD27, anti CD19-CAR, NGFR, CD62L, and CD127 antibodies for 30 minutes on ice. All flow cytometry data was collected on BD FACSCanto™ with BD FACS DIVA™ software and data was analyzed using FlowJo™ software (BD Biosciences). All antibody staining was performed in BD Stain Buffer at 4 degrees Celsius. Cells were sorted by CCR7 (BV650) and CD45RA (APC-CY7) expression. Upon manufacturing cells were evaluated for CD4, CD8, CCR7, CD45RA, CD62L, CD127, TCF7 (anti-CD19-CAR for CAR detection), anti-LNGFR (for the detection of TCF7 or Bach2 expression) expression on day 9 or day 30 of manufacturing. In some trials two expression panels were evaluated. Panel 1, CD4 (FITC), CD8 (PE), CD127 (PECY7), CD62L (APC-CY7), anti-CD19-CAR (AF647), LNGFR (BV421). Panel 2, CD8 (FITC), CD4 (PE-CY7), CD45RA (APC-CY7), CCR7 (BV650), CD27 (PE), anti TCF7 (AF647), LNGFR (BV421). For intracellular TCF7 staining, cells were surface stained with the respective antibodies, spun, washed in BD Stain buffer, fixed for 1 hour in 0.8% PFA room temperature, spun, washed in BD stain buffer, permeabilized with BD Permbuffer for 1 hour 4 degrees, stained with TCF7 antibody overnight in BD Permbuffer at 4 degrees Celsius. T Cells were then washed 1× in BD Stain buffer data was collected with a BD FACS Canto™ II.

Subset Bulk RNAseq

300×10$^6$ CD4 and 3300×10$^6$ CD8 T cells were stained with CD4, CD8, CCR7, and CD45RA for 30 minutes on ice. Naïve (CCR7+, CD45RA+), Central Memory (CCR7+, CD45RA−), Effector Memory (CCR7−, CD45RA−), and TEMRA (CCR7−, CD45RA+) were sorted based on surface expression of CCR7 and CD45RA. CD4 and CD8 cells were activated at a 1:1 ratio, and cultured detailed in Example 2. On days 7-10, subsets are frozen and sent for RNA isolation, polyA enrichment, and subsequent RNAseq analysis.

The data obtained for the expression of two transcription factors, TCF7 and Bach2 is shown in Table 4. Comparison of the expression levels in bulk T cells between day 0 and day 10 indicates that the overall expression of these two transcription factors dropped during the CD19 CAR manufacturing. However, this drop was dependent on differentiation. Closer examination of the data shown in Table 4 showed that in the naïve T cell population the two transcription factors, TCF7 and Bach2, were highly expressed on naïve T cells both before and after T cell manufacturing. This correlation between the expression of these two transcription factors and the naïve phenotype suggests the potential for enhanced proliferation and anti-tumor efficacy by over expression of Bach2 and TCF7.

TABLE 4

Bach2 and TCF7 are highly expressed on Naïve T cells and downregulated during CD19 CAR manufacturing and during differentiation.

| Sample_ID | Donor | CD4 or CD8 | Subset Type |
| --- | --- | --- | --- |
| Donor 1.Day0.4Bulk.2 | Donor 1 | CD4 | Bulk |
| Donor 1.Day0.8B.2 | Donor 1 | CD8 | Bulk |
| Donor 1.4B2 | Donor 1 | CD4 | Bulk |
| Donor 2.4B2 | Donor 2 | CD4 | Bulk |
| Donor 1.8B2 | Donor 1 | CD8 | Bulk |
| Donor 2.8B2 | Donor 2 | CD8 | Bulk |
| Donor 1.Day0.4N.2 | Donor 1 | CD4 | Naïve |
| Donor 1.Day0.8N.2 | Donor 1 | CD8 | Naïve |
| Donor 1.4N2 | Donor 1 | CD4 | Naïve |
| Donor 2.4N2 | Donor 2 | CD4 | Naïve |
| Donor 1.8N2 | Donor 1 | CD8 | Naïve |
| Donor 2.8N2 | Donor 2 | CD8 | Naïve |
| Donor 1.Day0.4CM.2 | Donor 1 | CD4 | CM |
| Donor 1.Day0.8CM.2 | Donor 1 | CD8 | CM |
| Donor 1.4CM2 | Donor 1 | CD4 | CM |
| Donor 2.4CM2 | Donor 2 | CD4 | CM |
| Donor 1.8CM2 | Donor 1 | CD8 | CM |
| Donor 2.8CM2 | Donor 2 | CD8 | CM |
| Donor 1.Day0.4EM.2 | Donor 1 | CD4 | EM |
| Donor 1.Day0.8EM.2 | Donor 1 | CD8 | EM |
| Donor 1.4EM2 | Donor 1 | CD4 | EM |
| Donor 2.4EM2 | Donor 2 | CD4 | EM |
| Donor 1.8EM2 | Donor 1 | CD8 | EM |
| Donor 2.8EM2 | Donor 2 | CD8 | EM |
| Donor 1.Day0.4TEMRA.2 | Donor 1 | CD4 | TEMRA |
| Donor 1.Day0.8TEMRA.2 | Donor 1 | CD8 | TEMRA |
| Donor 1.4TEMRA2 | Donor 1 | CD4 | TEMRA |
| Donor 2.4TEMRA2 | Donor 2 | CD4 | TEMRA |
| Donor 1.8TEMRA2 | Donor 1 | CD8 | TEMRA |
| Donor 2.8TEMRA2 | Donor 2 | CD8 | TEMRA |

| Sample_ID | Day of Manufacturing | BACH2 Expression (Log2 RPKM) | TCF7 Expression (Log2 RPKM) |
| --- | --- | --- | --- |
| Donor 1.Day0.4Bulk.2 | D0 | 12.18279951 | 15.08430598 |
| Donor 1.Day0.8B.2 | D0 | 11.07961759 | 14.35546964 |
| Donor 1.4B2 | D10 | 6.566978079 | 7.376676031 |
| Donor 2.4B2 | D10 | 8.391197945 | 11.28157454 |
| Donor 1.8B2 | D10 | 7.593652159 | 10.42085825 |
| Donor 2.8B2 | D10 | 8.548765578 | 10.96591916 |
| Donor 1.Day0.4N.2 | D0 | 12.85552314 | 16.22461816 |
| Donor 1.Day0.8N.2 | D0 | 13.08924987 | 16.13064736 |
| Donor 1.4N2 | D10 | 9.747879063 | 13.05668935 |
| Donor 2.4N2 | D10 | 11.03546011 | 14.67638568 |
| Donor 1.8N2 | D10 | 10.67095795 | 12.84559787 |
| Donor 2.8N2 | D10 | 10.59232067 | 12.74574201 |
| Donor 1.Day0.4CM.2 | D0 | 12.23280333 | 15.79375385 |
| Donor 1.Day0.8CM.2 | D0 | 12.20077083 | 15.7026238 |
| Donor 3.4CM2 | D10 | 7.939420091 | 9.738954805 |
| Donor 2.4CM2 | D10 | 8.921835472 | 12.50114575 |
| Donor 1.8CM2 | D10 | 9.326513686 | 11.2143676 |
| Donor 2.8CM2 | D10 | 8.447847292 | 10.15596136 |
| Donor 1.Day0.4EM.2 | D0 | 12.21097331 | 14.99352548 |
| Donor 1.Day0.8EM.2 | D0 | 10.98262397 | 14.74856124 |
| Donor 1.4EM2 | D10 | 5.621476907 | 6.712606975 |
| Donor 2.4EM2 | D10 | 5.751637619 | 9.844278779 |
| Donor 1.8EM2 | D10 | 5.40336555 | 7.68549119 |
| Donor 2.8EM2 | D10 | 8.792021509 | 10.70992176 |
| Donor 1.Day0.4TEMRA.2 | D0 | 11.61611948 | 14.36552319 |
| Donor 1.Day0.8TEMRA.2 | D0 | 10.15650348 | 13.58357807 |
| Donor 1.4TEMRA2 | D10 | 5.004983265 | 6.82225017 |
| Donor 2.4TEMRA2 | D10 | 4.39555045 | 5.437017386 |
| Donor 1.8TEMRA2 | D10 | 5.971951715 | 8.284621868 |
| Donor 2.8TEMRA2 | D10 | 7.653031748 | 9.772489956 |

Example 2

The example shows the effect of the over expression of Bach2 and TCF7 on T cell expansion. T cells were co-transduced with CD19 CAR and TCF7, Bach2 lentivirus, or control to overexpress these respective transcription factors. The cells from 4 healthy donors were activated for 20 days. As cells expanded, cell number was quantified using a Vi-Cell XR instrument (Beckman Coulter). The Beckman Coulter Vi-Cell XR automates the Trypan Blue Dye Exclusion Method. Cells transduced with CD19 CAR and TCF7 or Bach2 expanded substantially more than CD19 CAR single-transduced cells. These cells continued to expand for at least 60 days while CD19 CAR single-transduced expansion plateaued and eventually died off.

Transcription Factor RNAseq

CD19 CAR+ T cells transduced with TCF7, Bach2 or control were subjected to RNA isolation, polyA enrichment, and subsequent RNAseq analysis as described in Example 1.

Bach2 and TCF7 Constructs

Nucleic acid sequences encoding Bach2 and TCF7 each linked, by a cleavable linker, to LNGFR (SEQ ID NO: 7 and SEQ ID NO: 11 respectively) where inserted into lentivirus vector backbone. LNGFR was used as a surrogate marker of Bach2 and/or TCF7 expression.

CD4 and CD8 T Cell Isolation

CD4 and CD8 T cells were isolated from healthy donor PBMC with CD4 and CD8 CliniMACS® beads and Clini-MACS® instrument. Cells were frozen at least at $25 \times 10^6$ cells/mL in and frozen down in CryoStor® cell cryopreservation media (Sigma Aldrich®) and stored under liquid nitrogen.

T Cell Culture, Activation and Transduction

Healthy donor T cells (1:1 Ratio of CD4 and CD8 T cells) were activated with plate-bound MACS GMP CD3 Pure (1.23 ug/mL for coating) and soluble mouse anti-human CD28 antibody (1 ug/mL final concentration) at $1 \times 10^6$ cells/mL on day 0 in CTS™ OpTmizer™ media supplemented with CTS™ OpTmizer™ Cell SR, CTS™ OpTmizer™ T cell expansion supplement, Penn/Strep/Glutamine, and 300 IU/mL IL-2.

On day 1, cells were lentivirally transduced at an MOI of 10 with TCF7 T2A LNGFR, Bach2 T2A LNGFR, or not transduced. On day 2, cells were retrovirally transduced with an anti CD19 CAR (FMC63 scFv). On day 3 virus was washed off, cells were counted, and placed at $0.5 \times 10^6$ cells/mL. Cells were counted on day 5 and day 7, and maintained at $0.5 \times 10^6$ cells/mL. On day 7-10 cells frozen down in CryoStor® cell cryopreservation media (Sigma Aldrich®) and stored under liquid nitrogen for functional testing.

Cytokine Production

At 16h post-co-culture, supernatants were collected and analyzed for cytokine levels using the Meso Scale Discovery V-PLEX Proinflammatory Panel 1 human kit according to the manufacturer's instructions. Specifically, supernatants from the co-cultures of T cell products plated at the 1:1 E:T ratio with antigen-expressing target cells were analyzed for levels of interferon gamma (IFN-γ), IL-2, tumor necrosis factor alpha (TNF-α), and IL-10 secretion mediated by antigen engagement. All samples were diluted to be within the range of detection. The level of each cytokine is reported as pg/mL and the lower limit of quantitation and upper limit of quantitation of each assay is reported.

TABLE 5

Etopic expression of Bach2 and TCF7 promotes continued CAR expansion.

| | Donor 3 | | | Donor 4 | | |
|---|---|---|---|---|---|---|
| Days Post Activation | CD19 CAR + TCF7 Cell Count (1e6) | CD19 CAR + BACH2 Cell Count (1e6) | CD19 CAR Cell Count (1e6) | CD19 CAR + TCF7 Cell Count (1e6) | CD19 CAR + BACH2 Cell Count (1e6) | CD19 CAR Cell Count (1e6) |
| 0 | 1 | 1 | 1 | 1 | 1 | 1 |
| 3 | 4.22994 | 5.39168 | 4.467546667 | 2.55 | 2.58 | 3.12 |
| 5 | 14.0434008 | 33.2127488 | 29.485808 | 11.067 | 12.8484 | 14.04 |
| 7 | 123.301059 | 187.9841582 | 169.2485379 | 67.73004 | 117.177408 | 106.704 |
| 9 | 133.1651437 | 164.6741226 | 113.7350175 | 237.05514 | 421.8386688 | 285.96672 |
| 11 | 580.6000267 | 737.7400692 | 373.0508573 | 715.9065228 | 1982.641743 | 703.4781312 |
| 13 | 1706.964079 | 2080.426995 | 910.2440919 | 1259.99548 | 3449.796633 | 801.9650696 |
| 15 | 3584.624565 | 5825.195586 | 1674.849129 | 2242.791955 | 6692.605469 | 866.1222751 |
| 20 | 6308.939234 | 19106.64152 | 3048.225415 | 4665.007266 | 20747.07695 | 588.9631471 |

| | Donor 5 | | | Donor 6 | | |
|---|---|---|---|---|---|---|
| Days Post Activation | CD19 CAR + TCF7 Cell Count (1e6) | CD19 CAR + BACH2 Cell Count (1e6) | CD19 CAR Cell Count (1e6) | CD19 CAR + TCF7 Cell Count (1e6) | CD19 CAR + BACH2 Cell Count (1e6) | CD19 CAR Cell Count (1e6) |
| 0 | 1 | 1 | 1 | 1 | 1 | 1 |
| 3 | 2.04 | 1.44 | 2.4 | 1.4915 | 1.4459 | 1.6131 |
| 5 | 4.896 | 8.8128 | 13.296 | 6.86 | 7.54 | 7.35 |
| 7 | 31.92192 | 72.26496 | 76.85088 | 18.48 | 20.88 | 19.8 |
| 9 | 86.8276224 | 260.153856 | 181.3680768 | 73.92 | 144.4896 | 108.108 |
| 11 | 458.4498463 | 1706.609295 | 714.5902226 | 335.6 | 890.06 | 510.27 |
| 13 | 733.519754 | 2696.442687 | 643.1312003 | 1006.79 | 2331.95 | 440.87 |
| 15 | 2127.207287 | 9113.976281 | 1003.284673 | 4288.93 | 11519.82 | 459.39 |
| 20 | 10508.404 | 43747.08615 | 1304.270074 | 9349.86 | 36402.62 | 354.65 |

TABLE 6

BACH2 increases IL-2 production, TCF7 lower IL-2 production compared to CD19 CAR.

| Donor | CD19 CAR + TCF7 IL-2 Production (pg/mL) |
|---|---|
| Donor 3 | 494.0382667 |
| Donor 5 | 287.2189333 |
| Donor 4 | 596.1678333 |

| CD19 CAR + BACH2 IL-2 Production (pg/mL) | CD19 CAR IL-2 Production (pg/mL) |
|---|---|
| 5858.250333 | 3847.085 |
| 2936.783333 | 2199.272 |
| 2645.996667 | 1141.695 |

Example 4

T cells were co-transduced with an anti CD19 CAR and/or TCF7, Bach2 expressing lentivirus (described in Example 3), to overexpress these respective transcription factors in the presence or absence of anti CD19 CAR. Cells from 2 healthy donors were activated for 16 days. As cells expanded, cell number was quantified using the Vi-Cell XR instrument. Cells transduced with only TCF7 or Bach2 alone did not have the same sustained rate of expansion of cells as CD19 CAR T cells with TCF7 or Bach2.

TABLE 7

Bach2 and TCF7 expansion in the presence and absence of anti CD19 CAR

| Days Post-Activation | UTD | CD19 CAR + TCF7 | CD19 CAR + BACH2 | CD19 CAR | TCF7 | BACH2 |
|---|---|---|---|---|---|---|
| Experiment #1 | | | | | | |
| 0 | 30 | 30 | 30 | 30 | 30 | 30 |
| 2 | 35.4 | 38.4 | 36.3 | 38.1 | 36.9 | 28.53 |
| 3 | 129.564 | 142.848 | 137.94 | 146.304 | 147.6 | 98.7138 |
| 5 | 285.0408 | 308.5517 | 284.1564 | 377.4643 | 283.392 | 232.9648 |
| 7 | 855.1224 | 894.7999 | 986.1318 | 1147.492 | 793.4978 | 931.8583 |
| 10 | 2189.113 | 4438.207 | 5932.049 | 5003.063 | 3761.179 | 4584.743 |
| 13 | 5385.219 | 17042.72 | 28948.4 | 13808.45 | 4513.414 | 9352.875 |
| 16 | 1615.568 | 36130.56 | 116372.6 | 11046.76 | 2617.78 | 7295.243 |
| Experiment #2 | | | | | | |
| 0 | 15 | 15 | 15 | 15 | 15 | 15 |
| 2 | 18.27 | 14.355 | 16.24 | 15.805 | 17.835 | 16.82 |
| 3 | 68.3298 | 63.4491 | 80.8752 | 67.0132 | 73.4802 | 62.5704 |
| 5 | 336.1826 | 210.651 | 498.1912 | 442.2871 | 596.6592 | 304.0921 |
| 7 | 1586.782 | 1849.516 | 2819.762 | 2538.728 | 2367.544 | 1678.589 |
| 10 | 8586.795 | 8709 | 11066.1 | 5595.763 | 16585.21 | 9609.517 |
| 13 | 6377.599 | 53769.37 | 87377.93 | 25122.74 | 15258.4 | 14125.99 |
| 16 | 4464.319 | 94634.09 | 286599.6 | 45723.38 | 15258.4 | 16386.15 |

Example 5

T cells from 4 healthy donors were co-transduced with CD19 CAR and TCF7, Bach2 lentivirus, or control as described in Example 3 to overexpress these respective transcription factors. Cells were activated for 30 days (see Example 3). After 30 days, surface expression of CD62L and CD127 was quantified using flow cytometry, see Example 1. Higher CD62L and CD127 expression levels were observed on CD19-CAR cells engineered to over express Bach2 cells compared to CD19 CAR alone, suggesting a less-differentiated memory phenotype on extended manufacturing.

TABLE 8A

Bach2-transduced cells, CD62L+ % on Extended Manufacturing (Day 30 Phenotype)

| Donor | CD19 CAR + TCF7 |
|---|---|
| Donor 4 | 29.2 |
| Donor 5 | 26.9 |
| Donor 6 | 8.17 |
| Donor 3 | 74 |

| CD19 CAR + BACH2 | CD19 CAR |
|---|---|
| 54.2 | 7.81 |
| 86.5 | 24.8 |
| 43.5 | 8.23 |
| 83.4 | 79.3 |

TABLE 8B

Bach2-transduced cells; CD127+ % on Extended Manufacturing (Day 30 Phenotype)

| Donor | CD19 CAR + TCF7 |
|---|---|
| Donor 4 | 15.8 |
| Donor 5 | 4.99 |
| Donor 6 | 20.7 |
| Donor 3 | 15.1 |

TABLE 8B-continued

Bach2-transduced cells; CD127+ % on Extended Manufacturing (Day 30 Phenotype)

| CD19 CAR + BACH2 | CD19 CAR |
|---|---|
| 33.8 | 3.61 |
| 44.4 | 2.97 |
| 16.8 | 6.83 |
| 47.5 | 12.7 |

Example 6

T cells from 5 healthy donors were co-transduced with CD19 CAR and TCF7, Bach2 lentivirus, or control to overexpress these respective transcription factors, as described in Example 3. Cells were activated for 7-9 days and cryopreserved as described in Example 3. Cells were thawed and re-stimulated with NALM6 CD19 antigen positive targets at a 1:1 ratio. Fresh targets were added every 3-4 days until T cells were unable to fully kill these targets. CD8 T cell counts were captured every 3-4 days using flow cytometry. Peak CD8 T cell count was determined as the highest number of CD8+ T cells recorded in the well during the serial killing assay.

To facilitate tracking of T cells in culture, NALM6 target cells were engineered to express both luciferase and GFP. NALM6 cells express CD19 antigen and are targeted by CD19 CAR containing T cells. CD4, CD8, and anti CD19 CAR antibodies were used to identify CD4+, CD8+, or CAR+ T cells in serial killing. GFP was used to identify surviving NALM6 target cells. At the start of serial killing, 25,000 NALM6 were added to 25,000 CAR+ T cells in R10 media in a 96 well plate. Every 4 days in a serial killing, luciferase was quantified using a Varioskan™ instrument (Thermo Scientific) (to measure % killing). Cells were stained for flow cytometry (CD4 PE-CY7, CD8-PE, anti-CD19-CAR-AF647, GFP) and cell counts were quantified on the Attune™ Nxt Flow Cytometer with Invitrogen™ Attune™ NxT Software and analyzed with FlowJo™ by BD Biosciences. Every 3-4 days, 25,000 NALM6 (target cells) were added to the existing wells of CAR T cells and the serial killing continued with new rounds of targets added every 3-4 days until T cells were unable to fully kill these targets.

TABLE 9

Ectopic Bach2 and TCF7 increases peak CD8 T cell expansion during CAR-mediated serial killing.

| Donor | CD19 CAR + TCF7 CD8 Cell Count | CD19 CAR + BACH2 CD8 Cell Count | CD19 CAR + TCF7 CD8 Cell Count |
|---|---|---|---|
| Donor 3 | 11512.66667 | 15633.66667 | 1204.5 |
| Donor 4 | 11624 | 6678.666667 | 3049.5 |
| Donor 5 | 6507.5 | 3007.833333 | 3536.333 |
| Donor 6 | 977.1666667 | 10435.16667 | 5793.667 |
| Donor 7 | 1105 | 4587 | 1647.5 |

Example 7

T cells were co-transduced with CD19 CAR and TCF7 or BACH2 lentivirus, or nothing to overexpress these respective transcription factors, as described in Example 3. Cells were activated for 7-9 days and cryopreserved, as described in Example 3. These cells were thawed and restimulated with NALM6 CD19 antigen positive targets at a 1:1 ratio. After 24 hours, supernatant was collected and the Meso Scale Discovery assay was performed to measure cytokine production, see Example 3.

TABLE 10

BACH2 increases IL-2 production, TCF7 lowers IL-2 production compared to CD19 CAR

| Donor | CD19 CAR + TCF7 IL-2 Production (pg/mL) |
|---|---|
| Donor 3 | 494.0382667 |
| Donor 5 | 287.2189333 |
| Donor 4 | 596.1678333 |

| CD19 CAR + BACH2 IL-2 Production (pg/mL) | CD19 CAR IL-2 Production (pg/mL) |
|---|---|
| 5858.250333 | 3847.085 |
| 2936.783333 | 2199.272 |
| 2645.996667 | 1141.695 |

Example 8

CD4 and CD8 T Cell Isolation

CD4 and CD8 T cells were isolated from healthy donor PBMC with CD4 and CD8 CliniMACS® beads and CliniMACS® instrument. Cells were frozen at least at $25 \times 10^6$ cells/mL in and frozen down in CryoStor® cell cryopreservation media (Sigma Aldrich®) and stored under liquid nitrogen.

T Cell Culture, Activation and Transduction

Healthy donor T cells (1:1 Ratio of CD4 and CD8 T cells) were activated with plate-bound MACS GMP CD3 Pure (1.23 ug/mL for coating) and soluble mouse anti-human CD28 antibody (1 ug/mL final concentration) at $1 \times 10^6$ cells/mL on day 0 in Optmizer CTS media supplemented with CTS Immune Cell SR, Optmizer CTS T cell expansion supplement, Penn/Strep/Glutamine, and 300 IU/mL IL-2.

On day 2, cells were retrovirally transduced with FMC63 Anti-CD19 CAR. On day 3, virus was washed off, cells were counted, and the Neon® Transfection Kit and Neon® Transfection System were used to transfect the Blimp-1 KO condition. On day 3, virus was washed off and cells were counted. Lyophilized multi-guide RNA (Gene Knockout Kit v2, Synthego) was reconstituted to 5 μg/μL in TE buffer. RNP complex was prepared by mixing equal volumes of Cas9 protein and sgRNA (10 μg of each) and incubated at 37 C for 15 minutes. $3 \times 10^6$ cells were washed once with 1×PBS before being resuspended in 100 μL using resuspension buffer from the Neon Transfection Kit and combined with RNP complex. Cells were then electroporated at 1600 V for 10 ms with 3 pulses using the Neon Transfection System (Thermo Fisher Scientific) and transferred to media at $1 \times 10^6$ cells/mL. Cells were counted on day 5 and day 7 and also maintained at $0.5 \times 10^6$ cells/mL. On day 9, cells were frozen in CryoStor® cell cryopreservation media (Sigma Aldrich®) at $10 \times 10^6$ cells/mL and stored in liquid nitrogen for functional testing. Under extended manufacturing, these cells were cultured for many days until cell viability fell below 40%, with cells counted and placed at $0.5 \times 10^6$ cells/mL every 3-4 days. The BLIMP1 gRNA sequences used for Blimp-1 knockout:

```
                                      (SEQ ID NO: 12)
GAAGUGGUGAAGCUCCCCUC;

(SEQ ID NO: 13)
CUCUCCCCGGGAGCAAAACC;

(SEQ ID NO: 14)
GUUGGCAGGGAUGGGCUUAA.
```

Memory Phenotyping

T cells were stained on day 9 of culture with CD4, CD8, CCR7, CD45RA, CD27, KIP1, CD62L, and CD127 antibodies for 30 minutes on ice. Cells were then washed 1× in BD Stain buffer and data was collected with a BD Fortessa™ cytometer.

Cytokine Production

At 16 hours post-co-culture, supernatants were collected and analyzed for cytokine levels using the Meso Scale Discovery V-PLEX Proinflammatory Panel 1 human kit according to the manufacturer's instructions. Specifically, supernatants from the co-cultures of T cell products plated at the 1:1 E:T ratio with antigen-expressing target cells were analyzed for levels of interferon gamma (IFN-γ), IL-2, tumor necrosis factor alpha (TNF-α), and IL-10 secretion mediated by antigen engagement. All samples were diluted to be within the range of detection. The level of each cytokine is reported as pg/mL and the lower limit of quantitation and upper limit of quantitation of each assay is reported.

Serial Killing Co-Culture

CD19 CAR T were thawed in RPMI media supplemented with HEPES, Penn/Strep/Glutamine and 10% FBS. T cells were counted and CAR Transduction was normalized between conditions so that 25,000 T cells were added to 25,000 NALM6 target cells engineered to express both luciferase and GFP (1:1 Effector: Target ratio). NALM6 cells express CD19 antigen and are targeted by CD19 CAR containing T cells. Every 3-4 days, T cell killing of NALM6 target cells was measured via luciferase detection. D-luciferin substrate was added to the co-culture wells at a final concentration of 0.14 mg/mL and plates were incubated at 37° C. in the dark for 10 minutes. Luminescent signal was read immediately after in a VarioSkan™ LUX or VarioSkan® Flash multimode microplate reader. T cell-mediated cytotoxicity was calculated as follows:

% Cytotoxicity=[1−luciferase signal of (sample of interest/target alone control)]*100.

T cells and target cell numbers were quantified via the Attune™ NxT flow cytometer. T cells were then repeatedly stimulated with fresh 25,000 target cells and this process was repeated every 3-4 days.

T cells from 2 healthy donors were transduced with CD19 CAR with or without Blimp-1 KO and activated for 30 days in. The Vi-Cell XR was used to obtain cell counts at each time point. Blimp-1 KO CD19 CAR T cells exhibited increased expansion over the CD19 CAR wildtype (WT) controls. The WT controls cell expansion plateaued and eventually died off, while the Blimp-1 KO CD19 CAR T cells continued to expand for at least 70 total days in an IL2 dependent manner.

TABLE 12

Blimp-1 KO improves proliferative capacity in continued expansion of CD19 CAR.

| Days Post Activation | CD19 CAR no pulse cell count (e6) | CD19 CAR pulse + cas9 cell count (e6) | CD19 CAR BLIMP1 KO cell count (e6) |
| --- | --- | --- | --- |
| Donor 8 | | | |
| 3 | 3 | 3 | 3 |
| 5 | 4.74 | 3.84 | 2.67 |
| 7 | 28.22 | 29.41 | 18.82 |
| 9 | 47.01 | 40.00 | 34.93 |
| 13 | 170.25 | 159.94 | 314.11 |

TABLE 12-continued

Blimp-1 KO improves proliferative capacity in continued expansion of CD19 CAR.

| Days Post Activation | CD19 CAR no pulse cell count (e6) | CD19 CAR pulse + cas9 cell count (e6) | CD19 CAR BLIMP1 KO cell count (e6) |
| --- | --- | --- | --- |
| 16 | 619.70 | 492.63 | 2010.27 |
| 20 | 1697.98 | 1812.87 | 16122.39 |
| 23 | 1212.36 | 1954.27 | 56105.91 |
| 27 | 1605.16 | 2861.05 | 355711.48 |
| 30 | 1486.38 | 2042.79 | 416893.85 |
| Donor 5 | | | |
| 3 | 3 | 3 | 3 |
| 5 | 5.82 | 4.74 | 4.32 |
| 7 | 30.39 | 28.22 | 24.23 |
| 9 | 57.83 | 47.01 | 36.04 |
| 13 | 155.94 | 75.89 | 392.72 |
| 16 | 517.71 | 160.89 | 2419.13 |
| 20 | 1832.68 | 331.43 | 17659.67 |
| 23 | 1502.79 | 391.75 | 61808.84 |
| 27 | 2094.90 | 550.79 | 425244.79 |
| 30 | 1717.81 | 425.21 | 348700.73 |

Example 9

T cells were transduced with CD19 CAR with or without Blimp-1 KO and activated for 9 days in 2 healthy donors and cryopreserved as described in Example 8. CD127 surface expression was quantified using flow cytometry as described in Example 8. A higher CD127 expression (higher memory expression) was observed on the Blimp-1 KO CD19 CAR T cells compared to the CD19 CAR wildtype controls.

TABLE 13

CD19 CAR Blimp-1 KO cells have less differentiated memory phenotype by end of manufacturing.

| | % CD127+ at day 9 | | |
| --- | --- | --- | --- |
| | CD19 CAR no pulse | CD19 CAR pulse + cas9 | CD19 CAR BLIMP1 KO |
| Donor 8 | 75.3 | 68.8 | 93.4 |
| Donor 5 | 80.2 | 76.8 | 87.6 |

Example 10

T cells from 2 healthy donors were transduced with CD19 CAR with or without Blimp-1 KO and activated for 9 days and cryopreserved as described in Example 8. These cells were thawed and restimulated with NALM6 CD19 antigen positive targets at a 1:1 ratio. After 24 hours, supernatant was collected and the Meso Scale Discovery assay was performed to measure cytokine production (see example 8). Blimp-1 KO CD19 CAR T cells resulted in increased IL-2, IFN-gamma, and TNF-alpha production compared to the CD19 CAR wildtype controls. Numbers in table reflect an average of n=3.

TABLE 14

CD19 CAR Blimp-1 KO cells produce higher levels of IL-2, IFN-gamma, and TNF-alpha upon restimulation with NALM6 target cells.

| | IL-2 production (pg/mL) | | | IfN gamma production (pg/mL) | | | TNF-alpha production (pg/mL) | | |
|---|---|---|---|---|---|---|---|---|---|
| | CD19 CAR no pulse | CD19 CAR pulse + cas9 | CD19 CAR BLIMP1 KO | CD19 CAR no pulse | CD19 CAR pulse + cas9 | CD19 CAR BLIMP1 KO | CD19 CAR no pulse | CD19 CAR pulse + cas9 | CD19 CAR BLIMP1 KO |
| Donor 8 | 1519.89 | 1225.46 | 3275.65 | 84425.07 | 83832.55 | 233445.70 | 926.07 | 1027.86 | 2162.34 |
| Donor 5 | 2355.43 | 736.92 | 3397.92 | 99699.07 | 34936.58 | 241314.00 | 994.21 | 384.65 | 1809.12 |

Example 11

T cells from 2 healthy donors were transduced with CD19 CAR with or without Blimp-1 KO and activated for 9 days and cryopreserved as described in Example 8. These cells were thawed and restimulated with NALM6 CD19 antigen positive targets at a 1:1 ratio. Fresh NALM6 CD19 antigen positive targets were added every 3-4 days until T cells were unable to fully kill these targets as described in Example 8. Total T cell counts were captured every 3-4 days using flow cytometry as described in Example 8. Blimp-1 KO CD19 CAR T cells had higher peak cell expansion and persistence upon this serial restimulation assay. Numbers in table reflect an average of n=6.

TABLE 15

Blimp-1 KO improves proliferative capacity upon repeated stimulation with CD19 positive NALM6 cells in a serial killing assay.

| Round of restimulation | CD19 CAR no pulse | CD19 CAR pulse + cas9 only | CD19 CAR BLIMP1 KO |
|---|---|---|---|
| CD4 cell count | | | |
| Donor 8 | | | |
| 1 | 402.33 | 394.33 | 3131.00 |
| 2 | 147.50 | 194.50 | 683.83 |
| 3 | 106.17 | 115.33 | 485.50 |
| 4 | 3.00 | 23.17 | 41.33 |
| 5 | 0.33 | 1.00 | 53.83 |
| 6 | 0.00 | 0.00 | 2.67 |
| 7 | 0.00 | 0.00 | 0.00 |
| 8 | 0.00 | 0.00 | 0.00 |
| Donor 5 | | | |
| 1 | 615.33 | 479.00 | 1511.67 |
| 2 | 327.83 | 91.33 | 4604.00 |
| 3 | 777.83 | 162.00 | 3640.83 |
| 4 | 77.00 | 18.83 | 1442.00 |
| 5 | 12.33 | 7.17 | 1462.83 |
| 6 | 1.83 | 1.50 | 345.33 |
| 7 | 0.00 | 0.00 | 58.83 |
| 8 | 0.00 | 0.00 | 0.00 |
| CD8 cell count | | | |
| Donor 8 | | | |
| 1 | 1661.17 | 2029.50 | 3131.00 |
| 2 | 1467.50 | 1069.33 | 9058.50 |
| 3 | 1065.00 | 822.83 | 7941.33 |
| 4 | 72.50 | 71.67 | 1938.00 |
| 5 | 23.83 | 22.33 | 2569.67 |
| 6 | 10.33 | 8.67 | 375.50 |
| 7 | 0.00 | 0.00 | 19.33 |
| 8 | 0.00 | 0.00 | 0.00 |
| Donor 5 | | | |
| 1 | 2082.00 | 885.00 | 3860.33 |
| 2 | 804.83 | 278.83 | 28081.67 |
| 3 | 1304.33 | 321.33 | 20119.33 |
| 4 | 439.83 | 68.33 | 11091.00 |
| 5 | 123.67 | 40.50 | 12821.83 |
| 6 | 44.67 | 13.67 | 4693.00 |
| 7 | 0.00 | 0.00 | 1091.50 |
| 8 | 0.00 | 0.00 | 0.00 |

Example 12

T cells were transduced with CD19 CAR with or without Blimp-1 KO and activated for 9 days in 2 healthy donors and cryopreserved, see Example 8. These cells were thawed and restimulated with NALM6 CD19 antigen positive targets at a 1:1 ratio. Fresh targets were added every 3-4 days until T cells were unable to fully kill these targets as described in Example 8. Killing was measured at each time point via a luminescence-based assay as described in Example 8. Blimp-1 KO CD19 CAR T cells were able to maintain close to 100% cytotoxicity for multiple more rounds of re-stimulation with targets than the CD19 CAR wildtype control. Numbers in table reflect an average of n=6.

TABLE 16

CD19 CAR Blimp-1 KO cells kill CD19 positive NALM6 target cells for more rounds of serial stimulation than CD19 CAR no pulse control.

| Round of restimulation | CD19 CAR no pulse | CD19 CAR pulse + cas9 only | CD19 CAR BLIMPI KO |
|---|---|---|---|
| Donor 8 | | | |
| 1 | 99.89 | 99.88 | 99.95 |
| 2 | 99.91 | 99.89 | 99.93 |
| 3 | 96.59 | 96.34 | 99.92 |
| 4 | 7.65 | 6.68 | 99.82 |
| 5 | 0.00 | 0.00 | 99.22 |
| 6 | 0.00 | 0.00 | 61.30 |
| 7 | 0.00 | 0.00 | 2.08 |
| 8 | 0.00 | 0.00 | 0.00 |
| Donor 5 | | | |
| 1 | 99.63 | 96.44 | 99.94 |
| 2 | 99.44 | 71.15 | 99.98 |
| 3 | 99.62 | 61.58 | 99.97 |
| 4 | 60.35 | 10.06 | 99.91 |
| 5 | 0.00 | 0.00 | 99.70 |
| 6 | 0.00 | 0.00 | 96.99 |
| 7 | 0.00 | 0.00 | 51.22 |
| 8 | 0.00 | 0.00 | 0.00 |

Example 13

The CAR construct used in Examples 13-17 was anti-CD19 (FMC63 scFv). A lentivirus vector was used for all T cell transductions.

CD3+ cells obtained from STEMCELL™ Technologies (Vancouver, Canada) were isolated from peripheral blood mononuclear cells obtained from healthy donors and frozen down in CryoStor® cell cryopreservation media (Sigma Aldrich®).

Donor CD3+ T cells were thawed and rested overnight in T cell media (X-VIVO™ with 5% human serum) with IL-2 (50 international units/ml). Cells were stimulated with anti-CD3/CD28 Dynabeads, (ThermoFisher Scientific) and simultaneously transduced with viral constructs (for CAR expression) for 48 hours. These cells were then CRISPR edited using RNP (ribonucleoprotein) complex delivered via a Lonza 4D-Nucleofector™ (described below). Cells were continuously cultured in T cells media with IL-2 until they were used for functional assays.

For CRISPR editing, 160 μM crRNA was combined with 160 μM trRNA (#cat; Horizon Discovery) at 1:1 molar ratio and incubated at 37 degrees for 20 min. Equal volume of 40 μM Cas9 protein was added to the crRNA:trRNA mixture and incubated for another 20 min. The mixture was then added to T cells resuspended in P3 buffer and nucleofected using manufacturers setting for activated human T cells on the 96-well shuttle device of the Lonza 4D-Nucleofector™. The crRNA used for knockouts are as follows: TNFAIP3/A20 (#cat CM-009919-03-0002; Horizon Discovery); non target guide (#cat U-007501-01-20; Horizon Discovery).

For serial stimulation and expansion assay, edited CAR-T cells from Day 10 of manufacturing and CD19+ Nalm6 target cells from American Type Culture Company (ATCC, Manassas, Va.) were incubated together at 1:1 effector:target ratio. 2-3 days later, a sample was collected, stained for different markers and phenotyped using flow cytometry. Absolute cell counts for both effector and target cells were also determined by including counting beads (ThermoFisher Scientific) during flow cytometry. As the CAR-T cells expanded during the assay, extra target cells were added to bring the E:T ratio back to 1:1 each time the cells were phenotyped. The assay was continued till CAR fold expansion dropped below one fold.

CD19CAR with A20KO showed increased expansion in comparison with the canonical CD19CAR. Absolute CAR+ numbers are shown in table 17 (a) and CAR+ fold expansion is shown in table 17(b).

TABLE 17a

| Total CAR+ cell numbers | | |
| --- | --- | --- |
| Days | CD19CAR (non target gRNA) | CD19CAR A20KO |
| 0 | 500000.00 | 500000.00 |
| 4 | 1320000.00 | 1380000.00 |
| 8 | 8250000.00 | 9690000.00 |
| 11 | 31100000.00 | 41300000.00 |
| 15 | 15455954.30 | 22007171.50 |
| 18 | 11300000.00 | 22100000.00 |
| 22 | 8110597.85 | 12560690.70 |
| 26 | 1111437.94 | 5447363.77 |
| 29 | 685502.46 | 16305349.10 |
| 33 | 360031.21 | 21561851.30 |
| 36 | 189817.29 | 24957395.70 |
| 40 | NA | 7573652.44 |
| 43 | NA | 1251515.99 |

TABLE 17b

| CAR+ fold expansion | | |
| --- | --- | --- |
| Days | CD19CAR (non target qRNA) | CD19CAR A20KO |
| 0 | 1.00 | 1.00 |
| 4 | 2.64 | 2.76 |
| 8 | 16.50 | 19.38 |
| 11 | 62.20 | 82.60 |
| 15 | 30.91 | 44.01 |
| 18 | 22.60 | 44.20 |
| 22 | 16.22 | 25.12 |
| 26 | 2.22 | 10.89 |
| 29 | 1.37 | 32.61 |
| 33 | 0.72 | 43.12 |
| 36 | 0.38 | 49.91 |
| 40 | NA | 15.15 |
| 43 | NA | 2.50 |

Example 14

T cells from a different donor were manufactured similar to that described in Example 13 and cells from day 12 of manufacturing were used in serial stimulation and expansion assay, see example 13.

CD19CAR with A20KO showed increased expansion in comparison with the canonical CD19CAR. Absolute CAR+ numbers are shown in table 18(a) and CAR+ fold expansion is shown in table 18(b). A20KO enhances CAR fold expansion in Serial Kill Assay.

TABLE 18a

| Total CAR+ cell numbers | | |
| --- | --- | --- |
| Days | CD19CAR (non target gRNA) | CD19CAR A20KO |
| 0 | 250000.00 | 250000.00 |
| 2 | 346989.53 | 237128.47 |
| 5 | 1202158.82 | 1529052.27 |
| 8 | 620732.16 | 2162885.29 |
| 12 | 124733.08 | 1718220.77 |
| 15 | 43478.69 | 1508315.82 |
| 19 | 7954.12 | 745226.69 |
| 22 | 1313.41 | 445980.56 |
| 27 | 1899.94 | 64640.39 |

TABLE 18b

| CAR+ fold expansion | | |
| --- | --- | --- |
| Days | CD19CAR (non target gRNA) | CD19CAR A20KO |
| 0 | 1.00 | 1.00 |
| 2 | 1.39 | 0.95 |
| 5 | 4.81 | 6.12 |
| 8 | 2.48 | 8.65 |
| 12 | 0.50 | 6.87 |
| 15 | 0.17 | 6.03 |
| 19 | 0.03 | 2.98 |
| 22 | 0.01 | 1.78 |
| 27 | 0.01 | 0.26 |

Example 15

The effect of A20KO in the CD19 CAR context was evaluated in in vivo using a disseminated CD19+ Nalm6 mouse model.

CD19+ Nalm6 cells containing a bioluminescent reporter were grown in 90% RPMI, 10% FBS, 1% L-Glutamine. NSG mice (NOD.Cg-Prkdc$^{scid}$Il2rg$^{tm1Wjl}$/SzJ) from Jackson Laboratory were used for the study. 8 week old mice were implanted by injecting intravenously via the lateral tail vein on day 0 with 5.0×10$^5$ CD19+ Nalm6 cells in 0.1 ml using a BD U-100 Insulin Syringes 1/2cc, 28G.

CAR-T cells were manufactured and edited as described in example 13. For CRISPR editing, The RNP complex was nucleofected into the T cells using the MaxCyte GT® Flow Transfection™ System. Briefly, RNP complexes were made as described in Example 13. T cells were resuspended in 90 ul of MaxCyte® Electroporation buffer (Cat # EPBS; HyClone™) transferred to the OC-100 Processing Assembly and nucleofected using the Expanded T cell-3 setting as per manufacturer's guidelines. Nucleofected cells were then cultured in G-Rex using T cell media supplemented with 100 international units/ml of IL-2. 100 ul of CAR-T cells from day 12 of manufacturing were dosed in mice through intravenous injection on day 7 post CD19+ Nalm6 implantation.

In vivo bioluminescence imaging was performed using an IVIS Lumina S5. Animals were imaged three at a time under ~2-3% isoflurane gas anesthesia. Each mouse was injected IP with 150 mg/kg D-luciferin and imaged in the prone 15 minutes after the injection. Large binning of the CCD chip was used, and the exposure time was adjusted to 30 second to obtain at least several hundred counts from the metastatic tumors that were observable in each mouse in the image and to avoid saturation of the CCD chip. BLI images were collected on days 5, 8, 12, 15, 19, 22, 22, 26, 28, 33, and 36. Images were analyzed using the Living Image version 4.5.4 software. Whole body fixed-volume ROIs were placed on prone images for each individual animal and labeled based on animal identification. Total flux (photons/sec) was calculated and exported for all ROIs.

BLI (Bioluminescence imaging) values (shown as Mean±SEM) corresponding to CD19+ Nalm6 tumor burden in mice is presented for different treatment groups (Table 19). Higher values indicate higher tumor burden. The A20KO enhancement performed better against the canonical CD19CAR at two different doses (number of cells indicated next to the group names). Control groups 1~4 were terminated earlier due to higher tumor burden as expected.

Example 16

T cells from a different donor were manufactured similar to that described in Example 13 and were used in serial stimulation and expansion assay as described in Example 13.

For CRISPR editing, 160 µM crRNA was combined with 160 µM trRNA (#cat; Horizon Discovery) at 1:1 molar ratio and incubated at 37 degrees for 20 min. Equal volume of 40 µM Cas9 protein was added to the crRNA:trRNA mixture and incubated for another 20 min. The mixture was then added to T cells resuspended in P3 buffer and nucleofected using manufacturers setting for activated human T cells on the Lonza 4D-Nucleofector™. The crRNA used for knockouts are as follows: TNFAIP3/A20 (#cat CM-009919-03-0002; Horizon Discovery); BLIMP1 (#cat CM-009322-04-0002; Horizon Discovery); non target guide (#cat U-007501-01-20; Horizon Discovery).

For serial stimulation and expansion assay, edited CAR-T cells from day 10 of manufacturing and CD19+ Nalm6 target cells from American Type Culture Company (ATCC, Manassas, Va.) were incubated together at 1:1 effector:target ratio. 2-3 days later, a sample was collected, stained for different markers and phenotyped using flow cytometry. Absolute cell counts for both effector and target cells were also determined by including counting beads (ThermoFisher Scientific) during flow cytometry. As the CAR-T cells expanded during the assay, extra target cells were added to bring the E:T ratio back to 1:1 each time the cells were phenotyped. The assay was continued till CAR fold expansion dropped below one fold.

CD19CAR with A20KO, BLIMP1KO showed increased expansion in comparison with the canonical CD19CAR. Absolute CAR+ numbers are shown in table 20 (a) and CAR+ fold expansion is shown in table 20(b).

TABLE 19

| Days | G1. Vehicle | G2. UT (6e5) | G3. UT A20KO (6e5) | G4. UT A20KO (2e5) |
|---|---|---|---|---|
| 5 | 4063333.33333333 ± 737516.85 | 5286666.66666667 ± 578461.56 | 5238333.33333333 ± 113583.33 | 406333.33333333 ± 283298.04 |
| 8 | 44466666.6666667 ± 15211545.32 | 83383333.3333333 ± 8488282.77 | 60716666.6666667 ± 19096987.84 | 66366666.6666667 ± 9786271.56 |
| 12 | 2618333333.33333 ± 564537667.28 | 3580000000 ± 353006137.81 | 3873333333.33333 ± 1129045811.49 | 3476666666.66667 ± 377974131.98 |
| 15 | 7353333333.33333 ± 763534180.27 | 10261666666.6667 ± 1067609218.98 | 9870000000 ± 946460071.35 | 7961666666.66667 ± 937451924.69 |
| 19 | 25750000000 ± 1682607104.07 | 28483333333.3333 ± 2416252838.13 | 27616666666.6667 ± 1663413491.72 | 28600000000 ± 3889130151.25 |
| 22 | | | | |
| 26 | | | | |
| 29 | | | | |
| 33 | | | | |
| 36 | | | | |

TABLE 20a

Total CAR+ cell numbers

| Days | CD19CAR (non target gRNA) | CD19CAR BLIMP1KO | CD19CAR A20KO |
|---|---|---|---|
| 0 | 500000 | 500000 | 500000 |
| 3 | 892374.11 | 853042.73 | 996026.20 |
| 6 | 1919232.19 | 3860092.65 | 3798406.97 |
| 9 | 2639387.27 | 9661408.46 | 9180460.42 |
| 12 | 2085323.43 | 7450750.61 | 7134948.74 |
| 16 | 1561165.78 | 4052771.73 | 8362042.51 |
| 19 | 1140000.00 | 1490000.00 | 4180000.00 |
| 21 | 624342.48 | 879249.92 | 2282454.75 |

TABLE 20b

CAR+ fold expansion

| Days | CD19CAR (non target gRNA) | CD19CAR BLIMP1KO | CD19CAR A20KO |
|---|---|---|---|
| 0 | 1 | 1 | 1 |
| 3 | 1.78 | 1.71 | 1.99 |
| 6 | 3.84 | 7.72 | 7.60 |
| 9 | 5.28 | 19.32 | 18.36 |
| 12 | 4.17 | 14.90 | 14.27 |
| 16 | 3.12 | 8.11 | 16.72 |
| 19 | 2.28 | 2.98 | 8.36 |
| 21 | 1.25 | 1.76 | 4.56 |

Example 17

CAR+ T cells were phenotyped prior to feeding at each time point. Memory compartments were assessed using CD62L, CD45RO (Table 21a) and CD127 (Table 2b) markers for both CD4 and CD8 compartments. A20KO, BLIMIP1KO and showed differential memory phenotype, especially at later time points in the serial kill assay. The antibodies used for this phenotyping are as follows: BUV737-CD3 (cat #612752; BD Biosciences), BUV563-CD4 (cat #612912; BD Biosciences), BUV395 (cat #563795; BD Biosciences), BV650-CD62L (cat #304832; BioLegend), AF488-CD45RO (cat #304212; BioLegend), PE-Cy7-CD127 (cat #351320; BioLegend), and in-house antibody (DL650-anti-FMC63) for CAR+ assessment. Data was acquired on BD FACSymphony A5 and BD FACSymphony A3 flow cytometers and was processed using BD FlowJo™ software.

TABLE 21a

Gene KOs in CD19CAR demonstrate differential memory compartments in serial killing assay
CD62L+ and CD45RO+

| | % of CD4+ CAR+ | | | % of CD8+ CAR+ | | |
|---|---|---|---|---|---|---|
| Days | CD19CAR (non target gRNA) | CD19CAR BLIMP1KO | CD19CAR A20KO | CD19CAR (non target gRNA) | CD19CAR BLIMP1KO | CD19CAR A20KO |
| 0 | 92.3 | 91.8 | 93.6 | 85.8 | 84.9 | 89.1 |
| 3 | 69.7 | 70.6 | 68.3 | 54.6 | 57.5 | 51.7 |
| 6 | 76.1 | 87 | 82.3 | 69.6 | 77.6 | 75.4 |
| 9 | 66 | 82.2 | 82.8 | 59.4 | 69.2 | 72.8 |
| 12 | 70.6 | 81.8 | 82.3 | 79.1 | 84.7 | 86.8 |
| 16 | 63.6 | 58.3 | 74.7 | 67.4 | 76.8 | 73.4 |
| 19 | 58.6 | 48 | 65.5 | 51.1 | 70.9 | 62 |
| 21 | 47.1 | 41.5 | 63.3 | 40.3 | 71.2 | 64.7 |

TABLE 21b

Expression of CD127+

| | % of CD4+ CAR+ | | | % of CD8+ CAR+ | | |
|---|---|---|---|---|---|---|
| Days | CD19CAR (non target gRNA) | CD19CAR BLIMP1KO | CD19CAR A20KO | CD19CAR (non target gRNA) | CD19CAR BLIMP1KO | CD19CAR A20KO |
| 0 | 49.2 | 61.7 | 45.6 | 15.2 | 29 | 10.2 |
| 3 | 16.3 | 23.6 | 13.6 | 5.32 | 13.5 | 5.07 |
| 6 | 39.1 | 51.6 | 38.9 | 21.8 | 33 | 21.5 |
| 9 | 23 | 35.2 | 29.5 | 11.2 | 24.8 | 17.3 |
| 12 | 21.8 | 40.2 | 37.4 | 7.91 | 22.4 | 21.3 |
| 16 | 9.14 | 18.4 | 18.8 | 4.07 | 11.1 | 14 |
| 19 | 6.97 | 6.28 | 8.93 | 2.05 | 2.97 | 8.07 |
| 21 | 4.41 | 5.69 | 4.26 | 1.19 | 1.52 | 3.53 |

While a number of embodiments have been described, it is apparent that the disclosure and examples may provide other embodiments that utilize or are encompassed by the compositions and methods described herein. Therefore, it will be appreciated that the scope of is to be defined by that which may be understood from the disclosure and the appended claims rather than by the embodiments that have been represented by way of example.

What is claimed is:

1. A modified immune cell engineered to:
   a. inhibit the endogenous expression of one or more of Blimp-1 and A20; and/or
   b. express exogenous TCF7 and exogenous Bach2;
   wherein the cell expresses a chimeric antigen receptor (CAR), further wherein the exogenous Bach2 comprises an amino acid sequence at least 75% identical to the amino acid sequence set forth as SEQ ID NO: 8.

2. The cell of claim 1, comprising a deficient Blimp-1 gene and/or a deficient A20 gene.

3. The cell of claim 2, wherein the deficient Blimp-1 gene and/or the deficient A20 gene is created by knockout.

4. The cell of claim 2, wherein the deficient gene is edited using CRISPR/Cas9, a zinc finger nuclease (ZFN), a TALEN, a MegaTAL, a meganuclease, Cpf1, homologous recombination, or a single stranded oligodeoxynucleotide (ssODN).

5. The cell of claim 1, wherein the endogenous expression of Blimp-1 and/or A20 is inhibited by an exogenous miRNA or an exogenous siRNA.

6. The cell of claim 1, wherein the exogenous TCF7 comprises an amino acid sequence at least 75% identical to the amino acid sequence set forth as SEQ ID NO: 4.

7. The cell of claim 1, wherein the CAR binds to a tumor antigen comprising CD19, CD20, PSMA, PSCA, BCMA, TACI, CS1, CLL-1, or GPC3.

8. The cell of claim 1, wherein the cell is a T cell.

9. The cell of claim 1, wherein the cell is characterized by increased peak fold proliferation rate, increased CAR-mediated killing, increased cytokine production and/or increased cellular characteristics associated with naïve phenotype.

10. The cell of claim 9, wherein the cellular characteristics associated with naïve phenotype include the surface expression of one or more of, CD62L, CD127, CCR7, CD27, and CD45RA.

11. A method of treating cancer, comprising:
    administering to a subject in need thereof a therapeutically effective amount of the cell of claim 1.

12. A method of increasing the peak fold proliferation rate of an immune cell:
    a. introducing in the immune cell an exogenous nucleic acid construct encoding a CAR; and
    b. inhibiting in the immune cell an endogenous expression of one or more of Blimp-1 and A20; and/or introducing into the immune cell an exogenous construct encoding TCF7 and Bach2,
    further wherein the exogenous Bach2 comprises an amino acid sequence at least 75% identical to the amino acid sequence set forth as SEQ ID NO: 8.

13. The method of claim 12, wherein inhibiting the endogenous expression one or more of Blimp-1 and A20, comprises editing a gene locus to eliminate expression of endogenous Blimp-1 and/or editing a gene locus to eliminate expression of endogenous A20.

14. The method of claim 13, wherein editing a gene locus comprises using a CRISPR/Cas9, a zinc finger nuclease (ZFN), a TALEN, a MegaTAL, a meganuclease, Cpf1, homologous recombination, or a single stranded oligodeoxynucleotide (ssODN).

15. The method of claim 12, wherein inhibiting the endogenous expression of one or more of Blimp-1 and A20 comprises expression of an exogenous miRNA or an exogenous siRNA that specifically targets Blimp-1 and/or expression of an exogenous miRNA or an exogenous siRNA that specifically targets A20.

16. The method of claim 12, wherein the exogenous TCF7 comprises an amino acid sequence at least 75% identical to the amino acid sequence set forth as SEQ ID NO: 4.

17. The method of claim 12, wherein the cell is a T cell.

* * * * *